(12) United States Patent
Nettekoven et al.

(10) Patent No.: US 7,371,751 B2
(45) Date of Patent: May 13, 2008

(54) THIAZOLE DERIVATIVES

(75) Inventors: Matthias Heinrich Nettekoven, Grenzach-Wyhlen (DE); Stephan Roever, Inzlingen (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 550 days.

(21) Appl. No.: 11/004,676

(22) Filed: Dec. 3, 2004

(65) Prior Publication Data

US 2005/0153962 A1    Jul. 14, 2005

(30) Foreign Application Priority Data

Dec. 8, 2003  (EP)  ............................. 03104584

(51) Int. Cl.
*A61K 31/427* (2006.01)
*A61K 31/5377* (2006.01)
*C07D 417/02* (2006.01)

(52) U.S. Cl. .................. 514/235.2; 514/370; 548/190; 544/133

(58) Field of Classification Search ............. 514/235.2, 514/370; 548/190
See application file for complete search history.

(56) References Cited

U.S. PATENT DOCUMENTS

| | | |
|---|---|---|
| 3,940,418 A | 2/1976 | Hamilton |
| 5,462,960 A | 10/1995 | Barth et al. |
| 5,596,106 A | 1/1997 | Cullinan et al. |
| 5,624,941 A | 4/1997 | Barth et al. |

FOREIGN PATENT DOCUMENTS

| | | |
|---|---|---|
| EP | 576357 | 6/1993 |
| EP | 656 354 A1 | 11/1994 |
| EP | 656 354 B1 | 11/1994 |
| EP | 658 546 A1 | 12/1994 |
| EP | 658 546 B1 | 12/1994 |
| WO | WO 96/02248 | 2/1996 |
| WO | WO 97/19063 | 5/1997 |
| WO | WO 00/15609 | 3/2000 |
| WO | WO 00/46209 | 8/2000 |
| WO | WO 01/32663 | 5/2001 |
| WO | WO 01/64632 | 9/2001 |
| WO | WO 01/64633 | 9/2001 |
| WO | WO 01/64634 | 9/2001 |
| WO | WO 01/70700 | 9/2001 |
| WO | WO 02/28346 | 4/2002 |
| WO | WO 03/072577 | 9/2003 |
| WO | WO2004/014884 | 2/2004 |
| WO | WO 2004/014884 | 2/2004 |

OTHER PUBLICATIONS

F. Barth, et. al., "Cannabinoid antagonists: From research tools to potential new drugs." Abstracts of Papers, 222nd ASC National Meeting, Chicago, IL Aug. 26-30, 2001.
F.M. Casiano, et. al., NIDA Res. Monogr. 105 (1991) 295-6.
G. Colombo, et. al., Life Sci. 63 (8) (1998) L-113-PL117.
W.A. Devane, et. al., Science 258 (1992) 1946-9.
V. Di Marzo, et. al., Nature 410 (6830) 822-825.
V. Di Marzo, et. al, Trends in Neuroscience 21 (12) (1998) 521-8.
C. Felder, et. al., J. Pharmacol. Exp. Ther. 284 (1) (1998) 291-7.
C. Felder, et. al., Proc. Natl. Acad. Sci. USA 90 (16) (1993) 7656-60.
Y. Gaoni, et. al., J. Am. Chem. Soc., 86 (1964) 1646.
K. Hosohata, et. al., Life Sci. 61 (1997) 115-118.
M. Kanyonyo, et. al., Bioorg. Med. Chem. Lett. 9 (15) (1999) 2233-2236.
R. Mechoulam (Ed.) in "Cannabinoids as therapeutic Agents", (1986) p. 1-20, CRC Press.
S. Munro, et. al., Nature 365 (1993) 61-61.
F. Ooms, et. al., J. Med. Chem 45 (9) (2002) 1748-1756.
M. Pacheco, et. al., J. Pharmacol. Exp. Ther. 257 (1) (1991) 170-183.
R.G. Pertwee, Curr. Med. Chem., 6 (8) (1999) 635-664.
R.G. Pertwee, Life Sci. 56 (23-24) (1995) 1949-55.
R.G. Pertwee, Pharmaceut. Sci. 3 (11) (1997) 539-545.
C. Porter, et. al., Pharmacol. Ther., 90 (1) (2001) 45-60.
D. Shire, J. Biol. Chem. 270 (8) (1995) 3726-31.
C.M. Williams, et. al., Psychopharmacology 143 (3) (1999) 315-317.
E.M. Williamson, et. al., Drugs 60 (6) (2000) 1303-1314.
Shipps, Jr., et. al., Bioorganic & Medicinal Chemistry Letters, Oxford, GB, vol. 15, No. 1, Oct. 28, 2004, p. 115-119.
Pertwee, Pharmacol. Ther. vol. 74, No. 2, p. 129-180 (1997).

*Primary Examiner*—Kamal A. Saeed
(74) *Attorney, Agent, or Firm*—George W. Johnston; Dennis P. Tramaloni

(57) ABSTRACT

The present invention relates to compounds of formula (I)

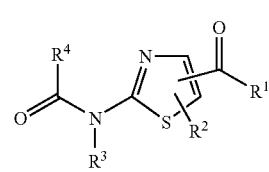

(I)

wherein $R^1$, $R^2$, $R^3$ and $R^4$ are as defined in the description and claims, and pharmaceutically acceptable salts thereof, for use as therapeutically active substances. The compounds are useful for the treatment and/or prophylaxis of diseases which are associated with the modulation of CB1 receptors, including obesity.

18 Claims, No Drawings

THIAZOLE DERIVATIVES

BACKGROUND OF THE INVENTION

Two different subtypes of cannabinoid receptors (CB1 and CB2) have been isolated and both belong to the G protein coupled receptor superfamily. An alternative spliced form of CB1, CB1A, has also been described, but it did not exhibit different properties in terms of ligand binding and receptor activation than CB1 (D. Shire, C. Carrillon, M. Kaghad, B. Calandra, M. Rinaldi-Carmona, G. Le Fur, D. Caput, P. Ferrara, J. Biol. Chem. 270 (8) (1995) 3726-31). The CB1 receptor is mainly located in the brain, whereas the CB2 receptor is predominately distributed in the periphery and primarily localized in spleen and cells of the immune system (S. Munro, K. L. Thomas, M. Abu-Shaar, Nature 365 (1993) 61-61). Therefore in order to avoid side effects a CB1-selective compound is desirable.

$\Delta^9$-tetrahydrocannabinol ($\Delta^9$-THC) is the principal psychoactive compound in the Indian hemp (Y. Gaoni, R. Mechoulam, J. Am. Chem. Soc., 86 (1964) 1646), *canabis savita* (marijuanan), which is used in medicine since ages (R. Mechoulam (Ed.) in "*Cannabinoids as therapeutic Agents*", 1986, pp. 1-20, CRC Press). $\Delta^9$-THC is a non-selective CB1/2 receptor agonist and is available in the USA as dronabinol (marinol®) for the alleviation of cancer chemotherapy-induced emesis (CIE) and the reversal of body weight loss experienced by AIDS patients through appetite stimulation. In the UK Nabolinone (LY-109514, Cesamet®), a synthetic analogue of $\Delta^9$-THC, is used for CIE (R. G. Pertwee, Pharmaceut. Sci. 3 (11) (1997) 539-545, E. M. Williamson, F. J. Evans, Drugs 60 (6) (2000) 1303-1314).

Anandamide (arachidonylethanolamide) was identified as the endogenous ligand (agonist) for the CB1 receptor (R. G. Pertwee, Curr. Med. Chem., 6 (8) (1999) 635-664; W. A. Devane, L. Hanus, A. Breuer, R. G. Pertwee, L. A. Stevenson, G. Griffin, D. Gibson, A. Mandelbaum, A. Etinger, R. Mechoulam, Science 258 (1992) 1946-9). Anandamide and 2-arachidonoylglycerol (2-AG) modulate at the presynaptic nerve teminal negatively adenylate cyclase and voltage-sensitive $Ca^{2+}$ channels and activates the inwardly rectifying $K^+$ channel (V. Di Marzo, D. Melck, T. Bisogno, L. De Petrocellis, Trends in Neuroscience 21 (12) (1998) 521-8), thereby affecting neurotransmitter release and/or action, which decreases the release of neurotransmitter (A. C. Porter, C. C. Felder, Pharmacol. Ther., 90 (1) (2001) 45-60).

Anandamide as $\Delta^9$-THC also increases feeding through CB1 receptor-mediated mechanism. CB1 receptor selective antagonists block the increase in feeding associated with administration of anandamide (C. M. Williams, T. C. Kirkham, Psychopharmacology 143 (3) (1999) 315-317; C. C. Felder, E. M. Briley, J. Axelrod, J. T. Simpson, K. Mackie, W. A. Devane, Proc. Natl. Acad. Sci. U.S.A. 90 (16) (1993) 7656-60) and caused appetite suppression and weight loss (G. Colombo, R. Agabio, G. Diaz, C. Lobina, R. Reali, G. L. Gessa, Life Sci. 63 (8) (1998) L113-PL117).

Leptin is the primary signal through which the hypothalamus senses nutritional state and modulates food intake and energy balance. Following temporary food restriction, CB1 receptor knockout mice eat less than their wild-type littermates, and the CB1 antagonist SR141716A reduces food intake in wild-type but not knockout mice. Furthermore, defective leptin signaling is associated with elevated hypothalamic, but not cerebellar, levels of endocannabinoids in obese db/db and ob/ob mice and Zucker rats. Acute leptin treatment of normal rats and ob/ob mice reduces anandamide and 2-arachidonoyl glycerol in the hypothalamus. These findings indicate that endocannabinoids in the hypothalamus may tonically activate CB1 receptors to maintain food intake and form part of the neural circuitry regulated by leptin (V. Di Marzo, S. K. Goparaju, L. Wang, J. Liu, S. Bitkai, Z. Jarai, F. Fezza, G. I. Miura, R. D. Palmiter, T. Sugiura, G. Kunos, Nature 410 (6830) 822-825). SR-141716A, a CB1 selective antagonist/inverse agonist is undergoing currently phase III clinical trials for the treatment of obesity. In a double blind placebo-controlled study, at the doses of 5, 10 and 20 mg daily, SR 141716 significantly reduced body weight when compared to placebo (F. Barth, M. Rinaldi-Carmona, M. Arnone, H. Heshmati, G. Le Fur, "*Cannabinoid antagonists: From research tools to potential new drugs.*" Abstracts of Papers, 222nd ACS National Meeting, Chicago, Ill., United States, Aug. 26-30, 2001).

Other compounds which have been proposed as CB1 receptor antagonists respectively inverse agonists are aminoalkylindois (AAI; M. Pacheco, S. R. Childers, R. Arnold, F. Casiano, S. J. Ward, J. Pharmacol. Exp. Ther. 257 (1) (1991) 170-183), like 6-bromo-(WIN54661; F. M. Casiano, R. Arnold, D. Haycock, J. Kuster, S. J. Ward, NIDA Res. Monogr. 105 (1991) 295-6) or 6-iodopravadoline (AM630, K. Hosohata, R. M. Quock, R. M; Hosohata, T. H. Burkey, A. Makriyannis, P. Consroe, W. R. Roeske, H. I. Yamamura, Life Sci. 61 (1997) 115-118; R. Pertwee, G. Griffin, S. Fernando, X. Li, A. Hill, A. Makriyannis, Life Sci. 56 (23-24) (1995) 1949-55). Arylbenzo[b]thiophene and benzo[b]furan (LY320135, C. C. Felder, K. E. Joyce, E. M. Briley, M. Glass, K. P. Mackie, K. J. Fahey, G. J. Cullinan, D. C. Hunden, D. W. Johnson, M. O. Chaney, G. A. Koppel, M. Brownstein, J. Pharmacol. Exp. Ther. 284 (1) (1998) 291-7) disclosed in WO9602248, US5596106, 3-alkyl-(5,5-diphenyl)imidazolidinediones (M. Kanyonyo, S. J. Govaerts, E. Hermans, J. H. Poupaert, D. M. Lambert, Bioorg. Med. Chem. Lett. 9 (15) (1999) 2233-2236.) as well as 3-alkyl-5-arylimidazolidinediones (F. Ooms, J. Wouters, O. Oscaro. T. Happaerts, G. Bouchard, P.-A. Carrupt, B. Testa, D. M. Lambert, J. Med. Chem. 45 (9) (2002) 1748-1756) are known to antagonize the CB1 receptor respectively act as an inverse agonist on the hCB1 receptor. WO0015609 (FR2783246-A1), WO0164634 (FR2805817-A1), WO0228346, WO0164632 (FR2805818-A1), WO0164633 (FR2805810-A1) disclosed substituted 1-bis(aryl)methyl-azetidines derivatives as antagonists of CB1. In W O170700 4,5-dihydro-1H-pyrazole derivatives are described as CB1 antagonists. In several patents bridged and non-bridged1,5-diphenyl-3-pyrazolecarboxamide derivatives are disclosed as CB1 antagonists/inverse agonists (WO0132663, WO0046209, WO9719063, EP658546, EP656354, U.S. Pat. No. 5,624,941, EP576357, U.S. Pat. No. 3,940,418).

SUMMARY OF THE INVENTION

The present invention is concerned with novel thiazole derivatives, their manufacture, pharmaceutical compositions containing them and their use as medicaments. The thiazole derivatives of the present invention are useful in treating obesity and other disorders.

In particular, the present invention relates to compounds of the general formula (I):

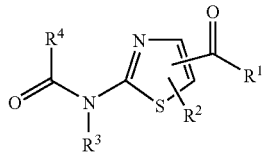

DETAILED DESCRIPTION OF THE INVENTION

The present invention provides selective, directly acting CB1 receptor antagonists and inverse agonists. Such antagonists/inverse agonists are useful in medical therapy, particularly in the treatment and/or prevention of diseases which are associated with the modulation of CB1 receptors. The present invention is concerned with novel thiazole derivatives, their manufacture, pharmaceutical compositions containing them and their use as medicaments. The thiazole derivatives of the present invention are useful in treating obesity and other disorders.

In particular, the present invention relates to compounds of formula (I):

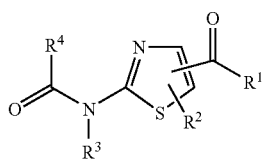

wherein $R^1$ is lower alkoxy, lower alkylamino-lower alkoxy, or —N($R^a$)$R^b$;

$R^a$ is hydrogen, lower alkyl, carbamoyl-lower alkyl, hydroxy-lower alkyl, di-hydroxy lower alkyl, lower alkinyl, lower alkoxy, lower alkoxy-lower alkyl, di-lower alkyl amino-lower alkyl, cycloalkyl; or $R^a$ is phenyl-lower alkyl residue, wherein the phenyl moiety may optionally be mono-, di- or tri-substituted, independently, by lower alkyl, lower alkoxy or halogen; or $R^a$ is a 5- or 6-membered heteroaromatic ring containing one or two nitrogen atoms in the ring, with the said heteroaromatic ring being attached to the remainder of the molecule by lower alkylene; or $R^a$ is a 5-, 6- or 7-membered saturated heterocyclic ring optionally containing one or two heteroatoms selected from nitrogen, oxygen and sulfur, said heterocyclic ring being optionally mono-, di-, or tri-substituted, independently, by lower alkyl;

$R^b$ is hydrogen, lower alkyl or lower alkoxy-lower alkyl; or $R^a$ and $R^b$ together with the nitrogen atom to which they are attached form a 4-, 5- or 6-membered saturated or unsaturated heterocyclic ring optionally containing a further heteroatom selected from nitrogen, oxygen and sulfur, said heterocyclic ring being optionally mono-, di-, or tri-substituted, independently, by lower alkyl, hydroxy, hydroxy-lower alkyl, lower alkoxy, lower alkoxy-lower alkyl, cyano, halogen, phenyl and/or benzyl;

$R^2$ is hydrogen or lower alkyl;

$R^3$ is phenyl mono-, di- or tri-substituted, independently, by lower alkoxy, halogen or perfluoro-lower alkoxy; and $R^4$ is a monocyclic aromatic ring optionally containing one or two nitrogen atoms in the ring, said ring being mono-, di- or tri-substituted, independently, by lower alkoxy, halogen or perfluoro-lower alkoxy;

or a pharmaceutically acceptable salt thereof.

Unless otherwise indicated, the following definitions are set forth to illustrate and define the meaning and scope of the various terms used to describe the invention herein. In this specification the term "lower" is used to mean a group consisting of one to eight, preferably of one to four carbon atom(s).

The term "halogen" refers to fluorine, chlorine, bromine and iodine, preferably to chlorine and fluorine.

The term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms.

The term "lower alkyl", alone or in combination with other groups, refers to a branched or straight-chain monovalent alkyl radical of one to eight carbon atoms, preferably one to four carbon atoms. This term is further exemplified by radicals such as methyl, ethyl, n-propyl, isopropyl, n-butyl, s-butyl, isobutyl, t-butyl, n-pentyl, 3-methylbutyl, n-hexyl, 2-ethylbutyl and the like.

The term "alkoxy" refers to the group R'—O—, wherein R' is alkyl. The term "lower alkoxy" refers to the group R'—O—, wherein R' is lower alkyl. Examples of lower alkoxy groups are e.g. methoxy, ethoxy, propoxy, isopropoxy, butoxy, isobutoxy and hexyloxy, with methoxy being especially preferred.

The term "lower alkylamino" refers to the group —NHR', wherein R' is a lower alkyl residue.

The term "di-lower alkylamino" refers to the group —N(R')R", wherein R' and R" are each independently a lower alkyl residue.

The term "cycloalkyl" refers to a monovalent carbocyclic radical of three to six, preferably five or six carbon atoms. This term is further exemplified by radicals such as cyclopropyl, cyclobutyl, cyclopentyl and cyclohexyl.

The term "lower alkinyl" refers to a lower alkyl group of two to four carbon atoms containing one or more tripple bond(s) in the alkylene chain.

The term "hydroxy-lower alkyl" refers to a lower alkyl group wherein one of the hydrogens of the lower alkyl group is replaced by hydroxy. Among the preferred hydroxy-lower alkyl groups are hydroxymethyl and 2-hydroxyethyl.

The term "di-hydroxy lower alkyl" refers to a lower alkyl group wherein two of the hydrogens of the lower alkyl group is replaced by hydroxy. Among the preferred di-hydroxy-lower alkyl groups is 2,3-dihydroxypropyl.

The term "phenyl-lower alkyl" refers to a lower alkyl group wherein one of the hydrogens of the lower alkyl group is replaced by phenyl. The phenyl moiety may optionally be mono-, di-, or tri-substituted, independently, by lower alkyl, lower alkoxy or halogen.

The term "perfluoro-lower alkoxy" refers to a lower alkoxy group wherein all of the hydrogens of the lower alkoxy group are replaced by fluoro. Among the preferred perfluoro-lower alkoxy groups is trifluoromethoxy.

The term "pharmaceutically acceptable salts" embraces salts of the compounds of formula (I) with inorganic or organic acids such as hydrochloric acid, hydrobromic acid, nitric acid, sulphuric acid, phosphoric acid, citric acid, formic acid, maleic acid, acetic acid, fumaric acid, succinic acid, tartaric acid, methanesulphonic acid, salicylic acid, p-toluenesulphonic acid and the like, which are non toxic to living organisms. Preferred salts with acids are formates, maleates, citrates, hydrochlorides, hydrobromides and methanesulfonic acid salts, with hydrochlorides being especially preferred.

In one embodiment, the present invention relates to a compound of formula (I) as defined above, wherein $R^1$ is lower alkoxy, lower alkylamino-lower alkoxy, or —N($R^a$)$R^b$. Preferable lower alkoxy residue $R^1$ is ethoxy. Preferable lower alkylamino-lower alkoxy residue $R^1$ is tert-butylamino-ethoxy. Preferable residues —N($R^a$)$R^b$ are pyrrolidinyl and piperidinyl, each of which may optionally mono- or di-substituted, independently, by lower alkyl, hydroxy, hydroxy-lower alkyl, lower alkoxy, lower alkoxy-lower alkyl, cyano, halogen, phenyl or benzyl.

Preferably, $R^1$ is —N($R^a$)$R^b$.

In another embodiment, the present invention relates to a compound of formula (I) as defined above, wherein $R^1$ is a residue —N($R^a$)$R^b$, and $R^a$ is hydrogen, lower alkyl, carbamoyl-lower alkyl, hydroxy-lower alkyl, di-hydroxy lower alkyl, lower alkinyl, lower alkoxy, lower alkoxy-lower alkyl, di-lower alkyl amino-lower alkyl or cycloalkyl. Preferable lower alkyl residues $R^a$ are methyl, ethyl, n-propyl, n-butyl and n-pentyl, with ethyl and n-propyl being especially preferred. Preferable carbamoyl lower alkyl residues $R^a$ are carbamoylmethyl and carbamoylethyl, with carbamoylmethyl being especially preferred Preferable hydroxy lower alkyl residues $R^a$ are 2-hydroxy-ethyl and 3-hydroxy-propyl, with 2-hydroxy-ethyl being especially preferred. Preferable di-hydroxy lower alkyl residue $R^a$ is 2,3-dihydroxypropyl.

Preferable lower alkinyl residues $R^a$ are propynyl, ethynyl and butynyl, with propynyl such as prop-2-ynyl being especially preferred. Preferable lower alkoxy residues $R^a$ are methoxy, ethoxy and propoxy, with methoxy being especially preferred. Preferable lower alkoxy-lower alkyl residues $R^a$ are methoxyethyl, ethoxyethyl, and methoxypropyl, with methoxyethyl being especially preferred. Preferable di-lower alkylamino residues $R^a$ are 2-dimethylamino-ethyl, 3-dimethylamino-propyl, 2-diethylamino-ethyl, 2-(ethyl-methyl-amino)-ethyl and 2-dimethylamino-1-methyl-ethyl, with 2-diethylamino-ethyl being especially preferred. Preferable cycloalkyl residues $R^a$ are cyclohepty, cyclohexyl, cyclopentyl, cyclobutyl and cyclopropyl, with cyclohexyl and cyclopentyl being especially preferred.

In another embodiment, the present invention relates to a compound of formula (I) as defined above, wherein $R^1$ is a residue —N($R^a$)$R^b$, and $R^a$ is a phenyl-lower alkyl residue, wherein the phenyl moiety may optionally be mono-, di- or tri-substituted, preferably mono-or di-substituted, independently, by lower alkyl such as methyl, lower alkoxy such as methoxy or halogen such as fluoro.

Preferable phenyl-lower alkyl residues $R^a$ are benzyl, 2-methyl-benzyl, 3-fluoro-benzyl, phenethyl, 1-methyl-3-phenyl-propyl and (3,4-dimethoxy-phenyl)-ethyl, with benzyl and phenethyl being especially preferred.

In another embodiment, the present invention relates to a compound of formula (I) as defined above, wherein $R^1$ is a residue —N($R^a$)$R^b$, and $R^a$ is a 5- or 6-membered heteroaromatic ring containing one or two nitrogen atoms in the ring, with the said heteroaromatic ring being attached to the remainder of the molecule by lower alkylene. Preferable heteroaromatic rings which are attached to the remainder of the molecule by lower alkylene in residue $R^a$ are 2-pyridin-2-yl-ethyl, 2-pyridin-2-yl-methyl, 3-pyridin-2-yl-ethyl, 3-pyridin-2-yl-methyl, 4-pyridin-2-yl-ethyl, 4-pyridin-2-yl-methyl and 2-(1H-imidazol-4-yl)-ethyl, with 2-pyridin-2-yl-ethyl being especially preferred.

In another embodiment, the present invention relates to a compound of formula (I) as defined above, wherein $R^1$ is a residue —N($R^a$)$R^b$, and $R^a$ is a 5-, 6- or 7-membered saturated heterocyclic ring optionally containing one or two heteroatoms selected from nitrogen, oxygen and sulfur, preferably nitrogen, said heterocyclic ring being optionally mono-, di-, or tri-substituted, preferably mono-substituted, independently, by lower alkyl such as methyl and ethyl.

Preferable heterocyclic rings $R^a$ are azepan-1-yl, 4-methyl-piperazin-1-yl, 1-ethyl-piperidin-3-yl, 1-methyl-piperidin-4-yl, 1-methyl-pyrrolidin-3-yl and piperidin-1-yl. In another embodiment, the present invention relates to a compound of formula (I) as defined above, wherein $R^1$ is a residue —N($R^a$)$R^b$, and $R^b$ is hydrogen, lower alkyl or lower alkoxy-lower alkyl. Preferable lower alkyl residues $R^b$ are methyl, ethyl, n-propyl, isopropyl, n-butyl, isobutyl, sec-butyl and tert-butyl, with ethyl and isopropyl being especially preferred. Preferable lower alkoxy-lower alkyl residue $R^b$ is 2-methoxy-ethyl.

In one embodiment, $R^b$ is hydrogen or lower alkyl such as methyl, ethyl, n-propyl, isopropyl, n-butyl, isobutyl, sec-butyl and tert-butyl. In another embodiment, $R^a$ and $R^b$ are independently lower alkoxy-lower alkyl such as 2-methoxy-ethyl.

Preferably, $R^b$ is ethyl or isopropyl.

In another embodiment, the present invention relates to a compound of formula (I) as defined above, wherein $R^1$ is a residue —N($R^a$)$R^b$, and $R^a$ and $R^b$ together with the nitrogen atom to which they are attached form a 4-, 5- or 6-membered saturated or unsaturated heterocyclic ring optionally containing a further heteroatom selected from nitrogen, oxygen and sulfur, preferably selected from nitrogen and sulfur, said heterocyclic ring being optionally mono-, di-, or tri-substituted, preferably mono- or di-substituted, independently, by lower alkyl, hydroxy, hydroxy-lower alkyl, lower alkoxy, lower alkoxy-lower alkyl, cyano, halogen, phenyl and/or benzyl.

Preferable heterocyclic rings formed by $R^a$ and $R^b$ together with the nitrogen atom to which they are attached are morpholino, thiomorpholino, azetidinyl, 2,5-dihydro-pyrrolyl, pyrrolidinyl, piperazinyl and piperidinyl, with pyrrolidinyl and piperidinyl being especially preferred. The heterocyclic rings formed by $R^a$ and $R^b$ together with the nitrogen atom to which they are attached may optionally be mono- or di-substituted, preferably mono-substituted, independently, by lower alkyl such as methyl, hydroxy, hydroxy-lower alkyl such as hydroxymethyl, lower alkoxy such as ethoxy, lower alkoxy-lower alkyl such as methoxymethyl, cyano, halogen such as fluoro, phenyl and/or benzyl.

More preferable heterocyclic rings formed by $R^a$ and $R^b$ together with the nitrogen atom to which they are attached are morpholino, thiomorpholino, pyrrolidinyl, pyrrolidinyl mono-substituted by lower alkyl such as methyl, pyrrolidinyl mono-substituted by hydroxy, pyrrolidinyl mono-substituted by hydroxy-lower alkyl such as hydroxymethyl, pyrrolidinyl mono-substituted by lower alkoxy-lower alkyl such as methoxymethyl, pyrrolidinyl mono-substituted by lower alkoxy such as ethoxy, pyrrolidinyl mono-substituted by cyano, azetidinyl, piperazinyl, piperazinyl mono-substituted by lower alkyl such as methyl, piperazinyl mono-substituted by phenyl, piperidinyl, piperidinyl mono-substituted by lower alkyl such as methyl, piperidinyl mono-substituted by benzyl, piperidinyl mono-substituted by hydroxy, piperidinyl di-substituted by halogen such as fluoro, and 2,5-dihydro-pyrrolyl.

In another embodiment, the present invention relates to a compound of formula (I)

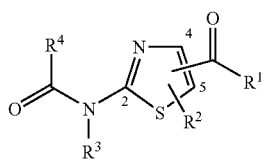

(I)

as defined above, wherein $R^2$ is hydrogen or lower alkyl. Preferable lower alkyl residue $R^2$ is methyl.

Substituent $R^2$ can be present at positions 4 or 5 of the central thiazole ring. Preferably, substituent $R^2$ is at the 5-position of the central thiazole ring.

In one preferable embodiment, $R^2$ is hydrogen when attached to the carbon atom at the 4-position of the central thiazole ring. In another preferable embodiment, $R^2$ is hydrogen or lower alkyl such as methyl when attached to the carbon atom at the 5-position of the central thiazole ring.

Most preferably, $R^2$ is hydrogen.

In another embodiment, the present invention relates to a compound of formula (I) as defined above, wherein $R^3$ is phenyl which is mono-, di- or tri-substituted, preferably mono- or di-substituted, independently, by lower alkoxy, halogen or perfluoro-lower alkoxy. Preferable lower alkoxy substitutent of a phenyl residue $R^3$ is methoxy. Preferable halogen substitutent of a phenyl residue $R^3$ is chloro. Preferable perfluoro-lower alkoxy substitutent of a phenyl residue $R^3$ is trifluoromethoxy.

In one preferable embodiment, the phenyl residue $R^3$ is mono-substituted, preferably in para-position, with halogen such as chloro or with perfluoro-lower alkoxy such as trifluoromethoxy. In another preferable embodiment, the phenyl residue $R^3$ is di-substituted, preferably in meta- and para-position, independently, with a substitutent selected from halogen such as chloro and lower alkoxy such as methoxy.

Preferable residues $R^3$ are 3,4-dimethoxy-phenyl, 4-chloro-phenyl, 4-trifluoromethoxy-phenyl and 4-chloro-3-methoxy-phenyl, with 3,4-dimethoxy-phenyl being especially preferred.

In another embodiment, the present invention relates to a compound of formula (I) as defined above, wherein $R^4$ is a monocyclic aromatic ring optionally containing one or two nitrogen atoms in the ring, said ring being mono-, di- or tri-substituted, independently, by lower alkoxy, halogen or perfluoro-lower alkoxy.

Preferable monocyclic aromatic rings $R^4$ containing one or two nitrogen atoms in the ring are pyridyl, pyrimidinyl, and pyrazyl, with pyridyl being especially preferred. Such monocyclic aromatic rings $R^4$ are mono-, di- or tri-substituted, preferably mono- or di-substituted, independently, by lower alkoxy such as methoxy, halogen such as chloro and fluoro or by perfluoro-lower alkoxy such as trifluoromethoxy.

In a preferable embodiment, $R^4$ is phenyl which is mono-, di- or tri-substituted, preferably mono- or di-substituted, independently, by lower alkoxy, halogen or perfluoro-lower alkoxy, with halogen being especially preferred. Preferable lower alkoxy substitutent of a phenyl residue $R^4$ is methoxy. Preferable halogen substitutents of a phenyl residue $R^4$ are chloro and fluoro, with chloro being especially preferred. Preferable perfluoro-lower alkoxy substitutent of a phenyl residue $R^4$ is trifluoromethoxy.

Mono-substituted phenyl residues $R^4$ are preferably substituted in ortho-position. di-substituted phenyl residues $R^4$ are preferably substituted in ortho-position and para-position.

Preferable residues $R^4$ are 2,4-dichloro-phenyl, 2-chloro-phenyl, and 2-chloro-4-fluoro-phenyl, with 2,4-dichloro-phenyl being especially preferred.

Preferred compounds of formula (I) are the compounds selected from the group consisting of:
2-[(2,4-dichloro-benzoyl)-(3,4-dimethoxy-phenyl)-amino]-thiazole-4-carboxylic acid ethyl ester,
2-[(2-chloro-benzoyl)-(3,4-dimethoxy-phenyl)-amino]-thiazole-4-carboxylic acid ethyl ester,
2,4-dichloro-N-(4-chloro-phenyl)-N-[4-(morpholine-4-carbonyl)-thiazol-2-yl]-benzamide, 2-[(4-chloro-phenyl)-(2,4-dichloro-benzoyl)-amino]-thiazole-4-carboxylic acid diethylamide,
2,4-dichloro-N-(4-chloro-phenyl)-N-[4-(pyrrolidine-1-carbonyl)-thiazol-2-yl]-benzamide,
2-[(4-chloro-phenyl)-(2,4-dichloro-benzoyl)-amino]-thiazole-4-carboxylic acid (2-dimethylamino-ethyl)-methyl-amide,
2-[(2-chloro-benzoyl)-(4-chloro-phenyl)-amino]-thiazole-4-carboxylic acid (2-dimethylamino-ethyl)-methyl-amide,
2,4-dichloro-N-(3,4-dimethoxy-phenyl)-N-[4-(morpholine-4-carbonyl)-thiazol-2-yl]-benzamide,
2-[(2,4-dichloro-benzoyl)-(3,4-dimethoxy-phenyl)-amino]-thiazole-4-carboxylic acid diethylamide,
2-[(2,4-dichloro-benzoyl)-(3,4-dimethoxy-phenyl)-amino]-thiazole-4-carboxylic acid benzylamide.

Further preferred compounds of formula (I) are:
2,4-dichloro-N-(3,4-dimethoxy-phenyl)-N-[4-(pyrrolidine-1-carbonyl)-thiazol-2-yl]-benzamide,
2-[(2,4-dichloro-benzoyl)-(3,4-dimethoxy-phenyl)-amino]-thiazole-4-carboxylic acid cyclohexylamide,
2-[(2,4-dichloro-benzoyl)-(3,4-dimethoxy-phenyl)-amino]-thiazole-4-carboxylic acid (2-dimethylamino-ethyl)-methyl-amide,
2-[(2,4-dichloro-benzoyl)-(3,4-dimethoxy-phenyl)-amino]-thiazole-4-carboxylic acid 2-methyl-benzylamide,
2-[(2-chloro-benzoyl)-(3,4-dimethoxy-phenyl)-amino]-thiazole-4-carboxylic acid benzylamide,
2-chloro-N-(3,4-dimethoxy-phenyl)-N-[4-(pyrrolidine-1-carbonyl)-thiazol-2-yl]-benzamide,
2-[(2-chloro-benzoyl)-(3,4-dimethoxy-phenyl)-amino]-thiazole-4-carboxylic acid cyclohexylamide,
2-[(2-chloro-benzoyl)-(3,4-dimethoxy-phenyl)-amino]-thiazole-4-carboxylic acid 3-fluoro-benzylamide,
2-[(4-chloro-phenyl)-(2,4-dichloro-benzoyl)-amino]-thiazole-4-carboxylic acid ethyl-methyl-amide,
2-[(4-chloro-phenyl)-(2,4-dichloro-benzoyl)-amino]-thiazole-4-carboxylic acid methyl-phenethyl-amide,
Further preferred compounds of formula (I) are:
2-[(4-chloro-phenyl)-(2,4-dichloro-benzoyl)-amino]-thiazole-4-carboxylic acid methyl-propyl-amide,
2-[(4-chloro-phenyl)-(2,4-dichloro-benzoyl)-amino]-thiazole-4-carboxylic acid ethyl-propyl-amide,
2,4-dichloro-N-(4-chloro-phenyl)-N-[4-(2-methyl-pyrrolidine-1-carbonyl)-thiazol-2-yl]-benzamide,
2,4-dichloro-N-(4-chloro-phenyl)-N-[4-(3-hydroxy-pyrrolidine-1-carbonyl)-thiazol-2-yl]-benzamide,
2-[(4-chloro-phenyl)-(2,4-dichloro-benzoyl)-amino]-thiazole-4-carboxylic acid azepan-1-ylamide, 2-[(4-chloro-phenyl)-(2,4-dichloro-benzoyl)-amino]-thiazole-4-carboxylic acid methyl-pentyl-amide,
2-[(4-chloro-phenyl)-(2,4-dichloro-benzoyl)-amino]-thiazole-4-carboxylic acid butyl-methyl-amide,
N-[4-(azetidine-1-carbonyl)-thiazol-2-yl]-2,4-dichloro-N-(4-chloro-phenyl)-benzamide,
2-[(4-chloro-phenyl)-(2,4-dichloro-benzoyl)-amino]-thiazole-4-carboxylic acid dimethylamide,
2-[(4-chloro-phenyl)-(2,4-dichloro-benzoyl)-amino]-thiazole-4-carboxylic acid (2-diethylamino-ethyl)-ethyl-amide,
Further preferred compounds of formula (I) are:
2,4-dichloro-N-(4-chloro-phenyl)-N-[4-(2-hydroxymethyl-pyrrolidine-1-carbonyl)-thiazol-2-yl]-benzamide,
2-[(4-chloro-phenyl)-(2,4-dichloro-benzoyl)-amino]-thiazole-4-carboxylic acid bis-(2-methoxy-ethyl)-amide,
2,4-dichloro-N-(4-chloro-phenyl)-N-[4-(2-(S)-methoxymethyl-pyrrolidine-1-carbonyl)-thiazol-2-yl]-benzamide,
2-[(4-chloro-phenyl)-(2,4-dichloro-benzoyl)-amino]-thiazole-4-carboxylic acid (1-methyl-3-phenyl-propyl)-amide,
2-[(4-chloro-phenyl)-(2,4-dichloro-benzoyl)-amino]-thiazole-4-carboxylic acid [2-(3,4-dimethoxy-phenyl)-ethyl]-methyl-amide,
2,4-dichloro-N-(4-chloro-phenyl)-N-[4-(4-methyl-piperazine-1-carbonyl)-thiazol-2-yl]-benzamide,
2,4-dichloro-N-(4-chloro-phenyl)-N-[4-(2-methyl-piperidine-1-carbonyl)-thiazol-2-yl]-benzamide,
2-[(4-chloro-phenyl)-(2,4-dichloro-benzoyl)-amino]-thiazole-4-carboxylic acid methyl-(2-pyridin-2-yl-ethyl)-amide,
2-[(4-chloro-phenyl)-(2,4-dichloro-benzoyl)-amino]-thiazole-4-carboxylic acid ethyl-(2-pyridin-2-yl-ethyl)-amide,
2,4-dichloro-N-(4-chloro-phenyl)-N-[4-(4-phenyl-piperazine-1-carbonyl)-thiazol-2-yl]-benzamide,
Further preferred compounds of formula (I) are:
2-[(4-chloro-phenyl)-(2,4-dichloro-benzoyl)-amino]-thiazole-4-carboxylic acid amide,
2-[(4-chloro-phenyl)-(2,4-dichloro-benzoyl)-amino]-thiazole-4-carboxylic acid [2-(1H-imidazol-4-yl)-ethyl]-amide,
2-[(4-chloro-phenyl)-(2,4-dichloro-benzoyl)-amino]-thiazole-4-carboxylic acid (2,3-dihydroxy-propyl)-methyl-amide,
2,4-dichloro-N-(4-chloro-phenyl)-N-[4-(2,5-dihydro-pyrrole-1-carbonyl)-thiazol-2-yl]-benzamide,
2-[(4-chloro-phenyl)-(2,4-dichloro-benzoyl)-amino]-thiazole-4-carboxylic acid (4-methyl-piperazin-1-yl)-amide,
2-[(4-chloro-phenyl)-(2,4-dichloro-benzoyl)-amino]-thiazole-4-carboxylic acid (2-dimethylamino-ethyl)-ethyl-amide,
2-[(4-chloro-phenyl)-(2,4-dichloro-benzoyl)-amino]-thiazole-4-carboxylic acid (3-dimethylamino-propyl)-amide,
2-[(4-chloro-phenyl)-(2,4-dichloro-benzoyl)-amino]-thiazole-4-carboxylic acid methyl-prop-2-ynyl-amide,
N-[4-(4-benzyl-piperidine-1-carbonyl)-thiazol-2-yl]-2,4-dichloro-N-(4-chloro-phenyl)-benzamide,
2,4-dichloro-N-(4-chloro-phenyl)-N-[4-(thiomorpholine-4-carbonyl)-thiazol-2-yl]-benzamide,
Further preferred compounds of formula (I) are:
2-[(4-chloro-phenyl)-(2,4-dichloro-benzoyl)-amino]-thiazole-4-carboxylic acid (1-ethyl-piperidin-3-yl)-amide,
2-[(4-chloro-phenyl)-(2,4-dichloro-benzoyl)-amino]-thiazole-4-carboxylic acid carbamoylmethyl-amide,
2-[(4-chloro-phenyl)-(2,4-dichloro-benzoyl)-amino]-thiazole-4-carboxylic acid methoxy-methyl-amide,
2,4-dichloro-N-(4-chloro-phenyl)-N-[4-(3-(S)-hydroxy-pyrrolidine-1-carbonyl)-thiazol-2-yl]-benzamide,
2,4-dichloro-N-(4-chloro-phenyl)-N-[4-(3-(R)-hydroxy-pyrrolidine-1-carbonyl)-thiazol-2-yl]-benzamide,
2-chloro-N-(3,4-dimethoxy-phenyl)-N-[4-(2-methyl-pyrrolidine-1-carbonyl)-thiazol-2-yl]-benzamide,
2-[(2-chloro-benzoyl)-(3,4-dimethoxy-phenyl)-amino]-thiazole-4-carboxylic acid methoxy-methyl-amide,
2-[(2-chloro-benzoyl)-(4-chloro-phenyl)-amino]-thiazole-4-carboxylic acid (2-diethylamino-ethyl)-ethyl-amide,
2-[(2-chloro-benzoyl)-(4-chloro-phenyl)-amino]-thiazole-4-carboxylic acid (2-dimethylamino-ethyl)-ethyl-amide,
2-chloro-N-(4-chloro-phenyl)-N-[4-(2-(S)-methoxymethyl-pyrrolidine-1-carbonyl)-thiazol-2-yl]-benzamide,
Further preferred compounds of formula (I) are:
2-chloro-N-(4-chloro-phenyl)-N-[4-(3-hydroxy-pyrrolidine-1-carbonyl)-thiazol-2-yl]-benzamide,
2-chloro-N-(4-chloro-phenyl)-N-[4-(thiomorpholine-4-carbonyl)-thiazol-2-yl]-benzamide,
2-[(2-chloro-benzoyl)-(4-chloro-phenyl)-amino]-thiazole-4-carboxylic acid ethyl-propyl-amide,
2-chloro-N-(4-chloro-phenyl)-N-[4-(2-methyl-pyrrolidine-1-carbonyl)-thiazol-2-yl]-benzamide,
2-[(2-chloro-benzoyl)-(4-chloro-phenyl)-amino]-thiazole-4-carboxylic acid ethyl-methyl-amide,
2-[(2-chloro-benzoyl)-(4-chloro-phenyl)-amino]-thiazole-4-carboxylic acid methoxy-methyl-amide,
2-chloro-N-(4-chloro-phenyl)-N-[4-(4-methyl-piperazine-1-carbonyl)-thiazol-2-yl]-benzamide,
2-[(2-chloro-benzoyl)-(4-chloro-phenyl)-amino]-thiazole-4-carboxylic acid methyl-propyl-amide,
2-[(2-chloro-benzoyl)-(4-chloro-phenyl)-amino]-thiazole-4-carboxylic acid carbamoylmethyl-amide,
2-[(2-chloro-benzoyl)-(4-chloro-phenyl)-amino]-thiazole-4-carboxylic acid amide,
Further preferred compounds of formula (I) are:
2-[(2,4-dichloro-benzoyl)-(3,4-dimethoxy-phenyl)-amino]-thiazole-4-carboxylic acid (2-diethylamino-ethyl)-ethyl-amide,
2-[(2,4-dichloro-benzoyl)-(3,4-dimethoxy-phenyl)-amino]-thiazole-4-carboxylic acid (2-dimethylamino-ethyl)-ethyl-amide,
2,4-dichloro-N-(3,4-dimethoxy-phenyl)-N-[4-(2-(S)-methoxymethyl-pyrrolidine-1-carbonyl)-thiazol-2-yl]-benzamide,
2,4-dichloro-N-(3,4-dimethoxy-phenyl)-N-[4-(3-hydroxy-pyrrolidine-1-carbonyl)-thiazol-2-yl]-benzamide,
2,4-dichloro-N-(3,4-dimethoxy-phenyl)-N-[4-(thiomorpholine-4-carbonyl)-thiazol-2-yl]-benzamide,
2-[(2,4-dichloro-benzoyl)-(3,4-dimethoxy-phenyl)-amino]-thiazole-4-carboxylic acid ethyl-propyl-amide,
2-[(2,4-dichloro-benzoyl)-(3,4-dimethoxy-phenyl)-amino]-thiazole-4-carboxylic acid bis-(2-methoxy-ethyl)-amide,
2,4-dichloro-N-(3,4-dimethoxy-phenyl)-N-[4-(2-methyl-pyrrolidine-1-carbonyl)-thiazol-2-yl]-benzamide,
2-[ (2,4-dichloro-benzoyl)-(3,4-dimethoxy-phenyl)-amino]-thiazole-4-carboxylic acid ethyl-methyl-amide,
2-[(2,4-dichloro-benzoyl)-(3,4-dimethoxy-phenyl)-amino]-thiazole-4-carboxylic acid methoxy-methyl-amide,
Further preferred compounds of formula (I) are:
2,4-dichloro-N-(3,4-dimethoxy-phenyl)-N-[4-(4-methyl-piperazine-1-carbonyl)-thiazol-2-yl]-benzamide
2-[(2,4-dichloro-benzoyl)-(3,4-dimethoxy-phenyl)-amino]-thiazole-4-carboxylic acid methyl-propyl-amide,
2,4-dichloro-N-(3,4-dimethoxy-phenyl)-N-[4-(3-methyl-piperidine-1-carbonyl)-thiazol-2-yl]-benzamide
2,4-dichloro-N-(3,4-dimethoxy-phenyl)-N-[4-(3-hydroxy-piperidine-1-carbonyl)-thiazol-2-yl]-benzamide, 2,4-dichloro-N-(3,4-dimethoxy-phenyl)-N-[4-(4-hydroxy-piperidine-1-carbonyl)-thiazol-2-yl]-benzamide,
2-[(2,4-dichloro-benzoyl)-(3,4-dimethoxy-phenyl)-amino]-thiazole-4-carboxylic acid carbamoylmethyl-amide,
2-[(2,4-dichloro-benzoyl)-(3,4-dimethoxy-phenyl)-amino]-thiazole-4-carboxylic acid amide,
2-[(4-chloro-phenyl)-(2,4-dichloro-benzoyl)-amino]-thiazole-4-carboxylic acid (1-methyl-piperidin-4-yl)-amide,
2-[(4-chloro-phenyl)-(2,4-dichloro-benzoyl)-amino]-thiazole-4-carboxylic acid methyl-(1-methyl-pyrrolidin-3-yl)-amide,
2-[(4-chloro-phenyl)-(2,4-dichloro-benzoyl)-amino]-thiazole-4-carboxylic acid ethyl-[2-(ethyl-methyl-amino)-ethyl]-amide,
Further preferred compounds of formula (I) are:
2-[(4-chloro-phenyl)-(2,4-dichloro-benzoyl)-amino]-thiazole-4-carboxylic acid (2-dimethylamino-1-methyl-ethyl)-amide,
2-[(4-chloro-phenyl)-(2,4-dichloro-benzoyl)-amino]-thiazole-4-carboxylic acid (2-hydroxy-ethyl)-isopropyl-amide,
2,4-dichloro-N-(4-chloro-phenyl)-N-[4-(4,4-difluoro-piperidine-1-carbonyl)-thiazol-2-yl]-benzamide,
2-[(4-chloro-phenyl)-(2,4-dichloro-benzoyl)-amino]-thiazole-4-carboxylic acid tert-butyl-(2-hydroxy-ethyl)-amide,
2,4-dichloro-N-(3,4-dimethoxy-phenyl)-N-[5-methyl-4-(pyrrolidine-1-carbonyl)-thiazol-2-yl]-benzamide,
2-[(2,4-dichloro-benzoyl)-(3,4-dimethoxy-phenyl)-amino]-5-methyl-thiazole-4-carboxylic acid (2-diethylamino-ethyl)-ethyl-amide,
2,4-dichloro-N-(3,4-dimethoxy-phenyl)-N-[4-(3-hydroxy-pyrrolidine-1-carbonyl)-5-methyl-thiazol-2-yl]-benzamide,
2,4-dichloro-N-(3,4-dimethoxy-phenyl)-N-[5-methyl-4-(thiomorpholine-4-carbonyl)-thiazol-2-yl]-benzamide,
2,4-dichloro-N-(3,4-dimethoxy-phenyl)-N-[5-methyl-4-(2-methyl-pyrrolidine-1-carbonyl)-thiazol-2-yl]-benzamide,
2-[(2,4-dichloro-benzoyl)-(3,4-dimethoxy-phenyl)-amino]-5-methyl-thiazole-4-carboxylic acid ethyl-methyl-amide,
Further preferred compounds of formula (I) are:
2-[(2,4-dichloro-benzoyl)-(3,4-dimethoxy-phenyl)-amino]-5-methyl-thiazole-4-carboxylic acid methoxy-methyl-amide,
2-[(2,4-dichloro-benzoyl)-(3,4-dimethoxy-phenyl)-amino]-5-methyl-thiazole-4-carboxylic acid methyl-propyl-amide,
2,4-dichloro-N-(3,4-dimethoxy-phenyl)-N-[5-methyl-4-(3-methyl-piperidine-1-carbonyl)-thiazol-2-yl]-benzamide,
2,4-dichloro-N-(3,4-dimethoxy-phenyl)-N-[5-methyl-4-(morpholine-4-carbonyl)-thiazol-2-yl]-benzamide,
2-[(2,4-dichloro-benzoyl)-(3,4-dimethoxy-phenyl)-amino]-5-methyl-thiazole-4-carboxylic acid (2-hydroxy-ethyl)-methyl-amide,
2,4-dichloro-N-(3,4-dimethoxy-phenyl)-N-[4-(3-(S)-ethoxy-pyrrolidine-1-carbonyl)-5-methyl-thiazol-2-yl]-benzamide,
2-[(2,4-dichloro-benzoyl)-(3,4-dimethoxy-phenyl)-amino]-5-methyl-thiazole-4-carboxylic acid tert-butyl-(2-hydroxy-ethyl)-amide,
2,4-dichloro-N-[4-(2-(R)-cyano-pyrrolidine-1-carbonyl)-5-methyl-thiazol-2-yl] —N-(3,4-dimethoxy-phenyl)-benzamide,
2-[(4-chloro-phenyl)-(2,4-dichloro-benzoyl)-amino]-5-methyl-thiazole-4-carboxylic acid diethylamide,
2,4-dichloro-N-(4-chloro-phenyl)-N-[5-methyl-4-(pyrrolidine-1-carbonyl)-thiazol-2-yl]-benzamide,
Further preferred compounds of formula (I) are:
2-[(4-chloro-phenyl)-(2,4-dichloro-benzoyl)-amino]-5-methyl-thiazole-4-carboxylic acid (2-diethylamino-ethyl)-ethyl-amide,
2-[(4-chloro-phenyl)-(2,4-dichloro-benzoyl)-amino]-5-methyl-thiazole-4-carboxylic acid (2-dimethylamino-ethyl)-ethyl-amide,
2,4-dichloro-N-(4-chloro-phenyl)-N-[4-(3-hydroxy-pyrrolidine-1-carbonyl)-5-methyl-thiazol-2-yl]-benzamide,
2-[(4-chloro-phenyl)-(2,4-dichloro-benzoyl)-amino]-5-methyl-thiazole-4-carboxylic acid (2,3-dihydroxy-propyl)-methyl-amide,
2-[(4-chloro-phenyl)-(2,4-dichloro-benzoyl)-amino]-5-methyl-thiazole-4-carboxylic acid ethyl-propyl-amide,
2-[(4-chloro-phenyl)-(2,4-dichloro-benzoyl)-amino]-5-methyl-thiazole-4-carboxylic acid ethyl-methyl-amide,
2-[(4-chloro-phenyl)-(2,4-dichloro-benzoyl)-amino]-5-methyl-thiazole-4-carboxylic acid methoxy-methyl-amide,
2-[(4-chloro-phenyl)-(2,4-dichloro-benzoyl)-amino]-5-methyl-thiazole-4-carboxylic acid methyl-propyl-amide,
2,4-dichloro-N-(4-chloro-phenyl)-N-[5-methyl-4-(morpholine-4-carbonyl)-thiazol-2-yl]-benzamide,
2-[(4-chloro-phenyl)-(2,4-dichloro-benzoyl)-amino]-5-methyl-thiazole-4-carboxylic acid (2-hydroxy-ethyl)-methyl-amide,
Further preferred compounds of formula (I) are:
2,4-dichloro-N-(4-chloro-phenyl)-N-[4-(3-(R)-ethoxy-pyrrolidine-1-carbonyl)-5-methyl-thiazol-2-yl]-benzamide,
2-[(4-chloro-phenyl)-(2,4-dichloro-benzoyl)-amino]-5-methyl-thiazole-4-carboxylic acid tert-butyl-(2-hydroxy-ethyl)-amide,
2,4-dichloro-N-(4-chloro-phenyl)-N-[4-(2-(R)-cyano-pyrrolidine-1-carbonyl)-5-methyl-thiazol-2-yl]-benzamide,
2-[(2,4-dichloro-benzoyl)-(3,4-dimethoxy-phenyl)-amino]-thiazole-5-carboxylic acid diethylamide,
2,4-dichloro-N-(3,4-dimethoxy-phenyl)-N-[5-(pyrrolidine-1-carbonyl)-thiazol-2-yl]-benzamide,
2-[(2,4-dichloro-benzoyl)-(3,4-dimethoxy-phenyl)-amino]-thiazole-5-carboxylic acid (2-diethylamino-ethyl)-ethyl-amide,
2,4-dichloro-N-(3,4-dimethoxy-phenyl)-N-[5-(2-methyl-pyrrolidine-1-carbonyl)-thiazol-2-yl]-benzamide,
2-[(2,4-dichloro-benzoyl)-(3,4-dimethoxy-phenyl)-amino]-thiazole-5-carboxylic acid ethyl-methyl-amide,
2-[(2,4-dichloro-benzoyl)-(3,4-dimethoxy-phenyl)-amino]-thiazole-5-carboxylic acid methyl-propyl-amide,
2,4-dichloro-N-(3,4-dimethoxy-phenyl)-N-[5-(3-hydroxy-piperidine-1-carbonyl)-thiazol-2-yl]-benzamide,
Further preferred compounds of formula (I) are:
2,4-dichloro-N-(3,4-dimethoxy-phenyl)-N-[5-(morpholine-4-carbonyl)-thiazol-2-yl]-benzamide,
2,4-dichloro-N-(3,4-dimethoxy-phenyl)-N-[5-(3-(R)-ethoxy-pyrrolidine-1-carbonyl)-thiazol-2-yl]-benzamide,
2-[(2,4-dichloro-benzoyl)-(3,4-dimethoxy-phenyl)-amino]-thiazole-5-carboxylic acid tert-butyl-(2-hydroxy-ethyl)-amide,
2,4-dichloro-N-[5-(2-(R)-cyano-pyrrolidine-1-carbonyl)-thiazol-2-yl] —N-(3,4-dimethoxy-phenyl)-benzamide,
2,4-dichloro-N-(4-chloro-phenyl)-N-[5-(pyrrolidine-1-carbonyl)-thiazol-2-yl]-benzamide,
2-[(4-chloro-phenyl)-(2,4-dichloro-benzoyl)-amino]-thiazole-5-carboxylic acid piperidin-1-ylamide,
2,4-dichloro-N-(4-chloro-phenyl)-N-[5-(thiomorpholine-4-carbonyl)-thiazol-2-yl]-benzamide,
2-[(4-chloro-phenyl)-(2,4-dichloro-benzoyl)-amino]-thiazole-5-carboxylic acid ethyl-propyl-amide,
2-[(4-chloro-phenyl)-(2,4-dichloro-benzoyl)-amino]-thiazole-5-carboxylic acid bis-(2-methoxy-ethyl)-amide, 2,4-dichloro-N-(4-chloro-phenyl)-N-[5-(2-methyl-pyrrolidine-1-carbonyl)-thiazol-2-yl]-benzamide,
2-[(4-chloro-phenyl)-(2,4-dichloro-benzoyl)-amino]-thiazole-5-carboxylic acid ethyl-methyl-amide,
2-[(4-chloro-phenyl)-(2,4-dichloro-benzoyl)-amino]-thiazole-5-carboxylic acid methoxy-methyl-amide,
Further preferred compounds of formula (I) are:
2,4-dichloro-N-(4-chloro-phenyl)-N-[5-(4-methyl-piperazine-1-carbonyl)-thiazol-2-yl]-benzamide,
2-[(4-chloro-phenyl)-(2,4-dichloro-benzoyl)-amino]-thiazole-5-carboxylic acid methyl-propyl-amide,
2,4-dichloro-N-(4-chloro-phenyl)-N-[5-(3-(R)-ethoxy-pyrrolidine-1-carbonyl)-thiazol-2-yl]-benzamide,
2,4-dichloro-N-[4-(pyrrolidine-1-carbonyl)-thiazol-2-yl]—N-(4-trifluoromethoxy-phenyl)-benzamide,
2-chloro-N-[4-(pyrrolidine-1-carbonyl)-thiazol-2-yl]—N-(4-trifluoromethoxy-phenyl)-benzamide,
2-[(2-chloro-benzoyl)-(4-trifluoromethoxy-phenyl)-amino]-thiazole-4-carboxylic acid ethyl-methyl-amide,
2-[(2,4-dichloro-benzoyl)-(4-trifluoromethoxy-phenyl)-amino]-thiazole-4-carboxylic acid ethyl-methyl-amide,
rac-2,4-dichloro-N-[4-(2-methyl-pyrrolidine-1-carbonyl)-thiazol-2-yl]—N-(4-trifluoromethoxy-phenyl)-benzamide,
rac-2-chloro-4-fluoro-N-[4-(2-methyl-pyrrolidine-1-carbonyl)-thiazol-2-yl]—N-(4-trifluoromethoxy-phenyl)-benzamide,
rac-2-chloro-N-[4-(2-methyl-pyrrolidine-1-carbonyl)-thiazol-2-yl]—N-(4-trifluoromethoxy-phenyl)-benzamide,
2,4-dichloro-N-[4-(3(R)-hydroxy-pyrrolidine-1-carbonyl)-thiazol-2-yl]—N-(4-trifluoromethoxy-phenyl)-benzamide,
Further preferred compounds of formula (I) are:
2-chloro-N-[4-(3 (R)-hydroxy-pyrrolidine-1-carbonyl)-thiazol-2-yl]—N-(4-trifluoromethoxy-phenyl)-benzamide,
rac-2,4-dichloro-N-(4-chloro-3-methoxy-phenyl)-N-[4-(2-methyl-pyrrolidine-1-carbonyl)-thiazol-2-yl]-benzamide,
2-chloro-4-fluoro-N-[4-((R)-3-hydroxy-pyrrolidine-1-carbonyl)-thiazol-2-yl]-N-(4-trifluoromethoxy-phenyl)-benzamide,
2,4-dichloro-N-(4-chloro-3-methoxy-phenyl)-N-[4-(pyrrolidine-1-carbonyl)-thiazol-2-yl]-benzamide,
2-[(4-chloro-3-methoxy-phenyl)-(2,4-dichloro-benzoyl)-amino]-thiazole-4-carboxylic acid ethyl-methyl-amide,
2,4-dichloro-N-(4-chloro-3-methoxy-phenyl)-N-[4-((R)-3-hydroxy-pyrrolidine-1-carbonyl)-thiazol-2-yl]-benzamide,
2,4-dichloro-N-(4-chloro-3-methoxy-phenyl)-N-[5-methyl-4-(pyrrolidine-1-carbonyl)-thiazol-2-yl]-benzamide,
2,4-dichloro-N-(4-chloro-3-methoxy-phenyl)-N-[5-methyl-4-(morpholine-4-carbonyl)-thiazol-2-yl]-benzamide,
2,4-dichloro-N-(4-chloro-3-methoxy-phenyl)-N-[4-((R)-3-hydroxy-pyrrolidine-1-carbonyl)-5-methyl-thiazol-2-yl]-benzamide,
2-[(4-chloro-3-methoxy-phenyl)-(2,4-dichloro-benzoyl)-amino]-5-methyl-thiazole-4-carboxylic acid 2-tert-butylamino-ethyl ester, and
rac-2,4-dichloro-N-(4-chloro-3-methoxy-phenyl)-N-[5-methyl-4-(2-methyl-pyrrolidine-1-carbonyl)-thiazol-2-yl]-benzamide.

The pharmaceutically acceptable salts of the foregoing preferred compounds are accordingly also preferred.

Most preferred compounds of general formula (I) are the compounds selected from the group consisting of:
2-[(4-chloro-phenyl)-(2,4-dichloro-benzoyl)-amino]-thiazole-4-carboxylic acid (2-dimethylamino-ethyl)-ethyl-amide,
2,4-dichloro-N-(3,4-dimethoxy-phenyl)-N-[4-(2-methyl-pyrrolidine-1-carbonyl)-thiazol-2-yl]-benzamide,
2-[(2,4-dichloro-benzoyl)-(3,4-dimethoxy-phenyl)-amino]-thiazole-4-carboxylic acid methyl-propyl-amide,
2-[(4-chloro-phenyl)-(2,4-dichloro-benzoyl)-amino]-thiazole-4-carboxylic acid methyl-(1-methyl-pyrrolidin-3-yl)-amide,
2,4-dichloro-N-(3,4-dimethoxy-phenyl)-N-[5-methyl-4-(pyrrolidine-1-carbonyl)-thiazol-2-yl]-benzamide,
2-[(2,4-dichloro-benzoyl)-(3,4-dimethoxy-phenyl)-amino]-5-methyl-thiazole-4-carboxylic acid methoxy-methyl-amide,
2-[(2,4-dichloro-benzoyl)-(3,4-dimethoxy-phenyl)-amino]-5-methyl-thiazole-4-carboxylic acid methyl-propyl-amide,
2,4-dichloro-N-[4-(2-(R)-cyano-pyrrolidine-1-carbonyl)-5-methyl-thiazol-2-yl]-N-(3,4-dimethoxy-phenyl)-benzamide,
2-[(4-chloro-phenyl)-(2,4-dichloro-benzoyl)-amino]-5-methyl-thiazole-4-carboxylic acid (2-dimethylamino-ethyl)-ethyl-amide,
2-[(4-chloro-phenyl)-(2,4-dichloro-benzoyl)-amino]-5-methyl-thiazole-4-carboxylic acid tert-butyl-(2-hydroxy-ethyl)-amide,
2-[(2,4-dichloro-benzoyl)-(3,4-dimethoxy-phenyl)-amino]-thiazole-5-carboxylic acid methyl-propyl-amide,
2-[(2,4-dichloro-benzoyl)-(3,4-dimethoxy-phenyl)-amino]-thiazole-5-carboxylic acid tert-butyl-(2-hydroxy-ethyl)-amide,
2,4-dichloro-N-(4-chloro-phenyl)-N-[5-(4-methyl-piperazine-1-carbonyl)-thiazol-2-yl]-benzamide,
2-[(4-chloro-phenyl)-(2,4-dichloro-benzoyl)-amino]-thiazole-5-carboxylic acid methyl-propyl-amide,
2,4-dichloro-N-(4-chloro-3-methoxy-phenyl)-N-[4-(pyrrolidine-1-carbonyl)thiazole-2-yl]-benzamide,
2-[(4-chloro-3-methoxy-phenyl)-(2,4-dichloro-benzoyl)-amino]-5-methyl-thiazole-4-carboxylic acid 2-tert-butylamino-ethyl ester,
rac-2,4-dichloro-N-(4-chloro-3-methoxy-phenyl)-N-[5-methyl-4-(2-methyl-pyrrolidine-1-carbonyl)-thiazol-2-yl]-benzamide,
and pharmaceutically acceptable salts thereof.

Processes for the manufacture of compounds of formula I are also an object of the invention.

Preferably, the invention relates to a process for the manufacture of compounds of formula (I) as defined herein before, which process comprises:

coupling a compound of formula ID

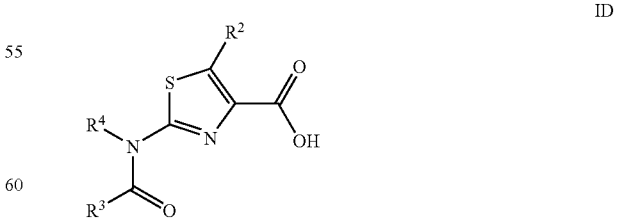

wherein $R^2$, $R^3$ and $R^4$ are as defined in claim 1;
with an alcohol of formula
$R^1$—OH
wherein $R^1$ is as defined in claim 1; or coupling a compound of formula ID

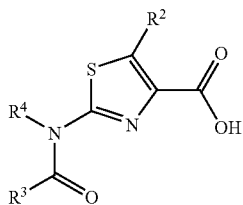

wherein $R^2$, $R^3$ and $R^4$ are as defined in claim 1;
with an amine of formula
$R^1$—$NH_2$ or a salt thereof
wherein $R^1$ is as defined in claim 1; or coupling a compound of formula ID

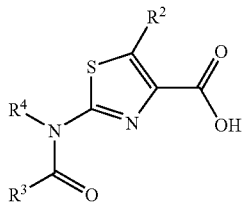

wherein $R^2$, $R^3$ and $R^4$ are as defined in claim 1;
with a hydroxylamine of formula
$R^1$—NHOH or a salt thereof
wherein $R^1$ is as defined in claim 1; or reacting a compound of formula IIB

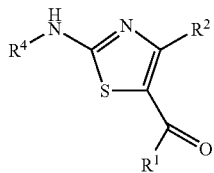

wherein $R^2$ and $R^4$ are as defined in claim 1 and $R^1$ is lower alkoxy;
with an acid chloride of formula
$R^3$—C(O)OCl
wherein $R^3$ is as defined in claim 1; or reacting a compound of formula IIC

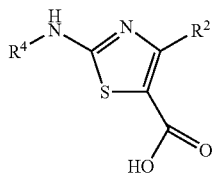

wherein $R^2$ and $R^4$ are as defined in claim 1;
with an acid chloride of formula
$R^3$—C(O)OCl
wherein $R^3$ is as defined in claim 1, followed by coupling the the intermediately built benzoyl-amino-thiazol derivatives with an amine of formula
$R^1$—$NH_2$ or a salt thereof
wherein $R^1$ is as defined in claim 1; or with a hydroxylamine of formula
$R^1$—NHOH or a salt thereof
wherein $R^1$ is as defined in claim 1.

The preparation of compounds of formula I of the present invention may be carried out in sequential or convergent synthetic routes. Syntheses of the invention are shown in the following Schemes 1 and 2. The skills required for carrying out the reaction and purification of the resulting products are known to those in the art. The substituents and indices used in the following description of the processes have the significance given above unless indicated to the contrary.

Compounds of general formula I can be prepared according to Scheme 1 as follows:

a) Thioureas IA (which are either commercially available, described previously in the literature or synthetically easily accessible via various routes decribed in literature) can be converted to amino-thiazols IB by various procedures described in the art. However, we find it convenient to react IA with α-bromo pyruvates (which are either commercially available, described previously in the literature or synthetically easily accessible via various routes decribed in literature) in the presence or absence of a solvent and in the presence or absence of a base. There is no particular restriction on the nature of the solvent to be employed, provided that it has no adverse effect on the reaction or the reagents involved and that it can dissolve the reagents, at least to some extent. Examples for suitable solvents include: Ethanol, methanol, dioxane and the like. There is no particular restriction on the nature of the base used in this stage, and any base commonly used in this type of reaction may equally be employed here. Examples of such bases include triethylamine and diisopropylethylamine, and the like. The reaction can take place over a wide range of temperatures, and the precise reaction temperature is not critical to the invention. We find it convenient to carry out the reaction with heating from ambient temperature to reflux. The time required for the reaction may also vary widely, depending on many factors, notably the reaction temperature and the nature of the reagents. However, a period of from 0.5 h to several days will usually suffice to yield the amino-thiazols derivatives IB or the respective salts thereof. For reaction conditions described in literature affecting such a reaction see for example: Biotechnology and Bioengineering 2000, 71, 9-18.

b) Amino-thiazols derivatives IB can undergo consecutive reactions like acylation/benzoylation of the amino moiety in IB under various reaction conditions. However, we find it convenient to react amino-thiazols derivatives IB with benzoyl chlorides (which are either commercially available, described previously in the literature or synthetically easily accessible via various routes decribed in literature) in order to access amino-thiazols derivatives IC in the presence or absence of a solvent and in the presence or absence of a base. There is no particular restriction on the nature of the solvent to be employed, provided that it has no adverse effect on the reaction or the reagents involved and that it can dissolve the reagents, at least to some extent. Examples for suitable solvents include: DCM, chloroform, dioxane and the like. There is no particular restriction on the nature of the base used in this stage, and any base commonly used in this type of reaction may equally be employed here. Examples of such bases include triethylamine and diisopropylethylamine, and the like. The reaction can take place over a wide range of temperatures, and the precise reaction temperature is not critical to the invention. We find it convenient to carry out the reaction with heating from ambient temperature to reflux. The time required for the reaction may also vary widely, depending on many factors, notably the reaction temperature and the nature of the reagents. However, a period of from 0.5 h to several days will usually suffice to yield the amino-thiazols derivatives IC. For reaction conditions described in literature affecting such a reaction see for example: Synlett 1999, 12, 1957-1959.

c) Amino-thiazols derivatives IC can undergo consecutive reactions like cleavage of the ester moiety of in IC under various reaction conditions in order to access acid derivatives ID. However, we find it convenient to react aminothiazol derivatives IC under acidic or basic conditions in the presence or absence of a solvent. There is no particular restriction on the nature of bases or acids to be employed, provided that they affect the desired reaction. Examples for suitable acids include acetic acid, HCl and the like; suitable bases include KOH aq., NaOH aq. And the like. There is no particular restriction on the nature of the solvent to be employed, provided that it has no adverse effect on the reaction or the reagents involved and that it can dissolve the reagents, at least to some extent. Examples for suitable solvents or mixtures thereof include: water, THF, dioxane and the like. The reaction can take place over a wide range of temperatures, and the precise reaction temperature is not critical to the invention. We find it convenient to carry out the reaction with heating from ambient temperature to reflux. The time required for the reaction may also vary widely, depending on many factors, notably the reaction temperature and the nature of the reagents. However, a period of from 0.5 h to several days will usually suffice to yield the acid derivatives ID. For reaction conditions described in literature affecting such reaction see for example: Comprehensive Organic Transformations: A Guide to Functional Group Preparations, $2^{nd}$ Edition, Richard C. Larock. John Wiley & Sons, New York, N.Y. 1999.

d) Acid derivatives ID can be converted to the respective amides or esters by various methods described in the literature to access the final compounds with general formula I. However, we find it convenient to react acid derivatives ID with alcohols, amines (or their respective salts) or hydroylamines (or their respective salts), under various conditions with a coupling reagent suitable for such a transformation in the presence or absence of a solvent in the presence or absence of an acid or an base depending on the desired transformation. Any coupling reagent commonly used in such a transformation can equally be employed, provided that they affect the reaction and show no adverse effect on the reaction or the reagents involved. Typical coupling reagents for amines and hydroxylamines include: N,N'-carbonyldiimidazole (CDI), O-(7-azabenzotriazol-1-yl)-N,N,N',N'-tetramethyluronium hexafluorophosphate (HATU), 1-(3-dimethylaminopropyl)-3-ethylcarbodiimide hydrochloride (EDCI) or O-benzotriazol-1-yl-N,N,N',N'-tetramethyluronium tetrafluoroborate (TBTU) and the like. For reaction conditions described in literature affecting such reaction see for example: Comprehensive Organic Transformations: A Guide to Functional Group Preparations, 2nd Edition, Richard C. Larock. John Wiley & Sons, New York, N.Y. 1999. There is no particular restriction on the nature of the solvent to be employed, provided that it has no adverse effect on the reaction or the reagents involved and that it can dissolve the reagents, at least to some extent. Examples for suitable solvents or mixtures thereof include: dichloromethane (DCM), dimethylformamide (DMF), tetrahydrofuran (THF), dioxane and the like. The reaction can take place over a wide range of temperatures, and the precise reaction temperature is not critical to the invention. We find it convenient to carry out the reaction with heating from ambient temperature to reflux. The time required for the reaction may also vary widely, depending on many factors, notably the reaction temperature and the nature of the reagents. However, a period of from 0.5 h to several days will usually suffice to yield the thiazole derivatives I.

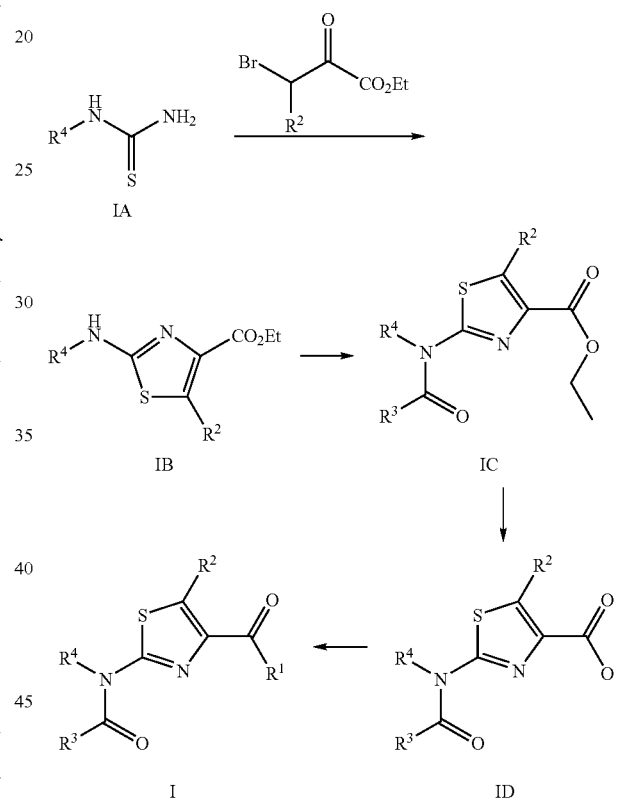

Compounds of general formula I can be prepared according to Scheme 2 as follows:

a) Amino-methylidene-thiourea derivatives IIA (those compounds are either commercially available, described previously in the literature or synthetically easily accessible via various routes decribed, like for instance the reaction of an isothiocyanate with an amidine derivative. For reaction conditions described in literature affecting such a reaction see for example: Tetrahedron 2001, 57, 153) can be converted to amino-thiazols IIB by various procedures described in the art. However, we find it convenient to react IIA with α-bromo acetic esters (which are either commercially available, described previously in the literature or synthetically easily accessable via various routes decribed in literature) in the presence or absence of a solvent and in the presence or absence of a base. There is no particular restriction on the nature of the solvent to be employed, provided that it has no adverse effect on the reaction or the reagents involved and that it can dissolve the reagents, at least to some extent. Examples for suitable solvents include: THF, DCM, dioxane and the like. There is no particular restriction on the nature of the base used in this stage, and any base commonly used in this type of reaction may equally be employed here. Examples of such bases include triethylamine and diisopropylethylamine, and the like. The reaction can take place over a wide range of temperatures, and the precise reaction temperature is not critical to the invention. We find it convenient to carry out the reaction with heating from ambient temperature to reflux. The time required for the reaction may also vary widely, depending on many factors, notably the reaction temperature and the nature of the reagents. However, a period of from 0.5 h to several days will usually suffice to yield the amino-thiazols derivatives IIB. For reaction conditions described in literature affecting such a reaction see for example: J. Org. Chem. 2000, 65, 7244.

b) The ester functionality in amino-thiazols derivatives IIB can be cleaved under various reaction conditions described in literature in order to access acid derivatives IIC. However, we find it convenient to react amino-thiazol derivatives IIB under basic conditions in the presence or absence of a solvent. There is no particular restriction on the nature of bases to be employed, provided that they affect the desired reaction. Examples for suitable bases include KOH aq., NaOH aq. and the like. There is no particular restriction on the nature of the solvent to be employed, provided that it has no adverse effect on the reaction or the reagents involved and that it can dissolve the reagents, at least to some extent. Examples for suitable solvents or mixtures thereof include: water, THF, dioxane and the like. The reaction can take place over a wide range of temperatures, and the precise reaction temperature is not critical to the invention. We find it convenient to carry out the reaction with heating from ambient temperature to reflux. The time required for the reaction may also vary widely, depending on many factors, notably the reaction temperature and the nature of the reagents. However, a period of from 0.5 h to several days will usually suffice to yield the acid derivatives IIC. For reaction conditions described in literature affecting such reaction see for example: Comprehensive Organic Transformations: A Guide to Functional Group Preparations, 2nd Edition, Richard C. Larock. John Wiley & Sons, New York, N.Y. 1999. In order to access compounds of the general formula I ($R^1$=lower alkoxy) various methods are available. However, we find it convenient to react amino-methylidene-thiourea derivatives IIA with bromoacetic acid ester derivatives ($R^1$=lower alkoxy) and access through the previously herein described general method the amino-thiazole derivatives IIB ($R^1$=lower alkoxy). Consecutively, we find it convenient to convert IIB ($R^1$=lower alkoxy) to the amino-thiazole derivatives I ($R^1$=lower alkoxy) by reaction of IIB with a suitable acid chloride in the presence or absence of a solvent and the presence or absence of a base. There is no particular restriction on the nature of the solvent to be employed, provided that it has no adverse effect on the reaction or the reagents involved and that it can dissolve the reagents, at least to some extent. Examples for suitable solvents include: THF, DCM, dioxane and the like. There is no particular restriction on the nature of the base used in this stage, and any base commonly used in this type of reaction may equally be employed here. Examples of such bases include triethylamine and diisopropylethylamine, and the like. The reaction can take place over a wide range of temperatures, and the precise reaction temperature is not critical to the invention. We find it convenient to carry out the reaction with heating from ambient temperature to reflux. The time required for the reaction may also vary widely, depending on many factors, notably the reaction temperature and the nature of the reagents. However, a period of from 0.5 h to several days will usually suffice to yield the amino-thiazols derivatives I ($R^1$=lower alkoxy). For reaction conditions described in literature affecting such a reaction see for example: Comprehensive Organic Transformations: A Guide to Functional Group Preparations, 2nd Edition, Richard C. Larock. John Wiley & Sons, New York, N.Y. 1999.

c) Acid derivative IIC can be converted under various reaction conditions to the desired amino thiazole derivatives I ($R^1$=lower alkylamino-lower alkoxy, or —N($R^a$)$R^b$). However, we find it convenient to react IIC with a suitable acid chloride in the presence or absence of a solvent and the presence or absence of a base. There is no particular restriction on the nature of the solvent to be employed, provided that it has no adverse effect on the reaction or the reagents involved and that it can dissolve the reagents, at least to some extent. Examples for suitable solvents include: THF, DCM, dioxane and the like. There is no particular restriction on the nature of the base used in this stage, and any base commonly used in this type of reaction may equally be employed here. Examples of such bases include triethylamine and diisopropylethylamine, and the like. The reaction can take place over a wide range of temperatures, and the precise reaction temperature is not critical to the invention. We find it convenient to carry out the reaction with heating from ambient temperature to reflux. The time required for the reaction may also vary widely, depending on many factors, notably the reaction temperature and the nature of the reagents. However, a period of from 0.5 h to several days will usually suffice to yield the intermediately formed benzoyl-amino-thiazol derivatives (for reaction conditions described in literature affecting such a reaction see for example: Comprehensive Organic Transformations: A Guide to Functional Group Preparations, 2nd Edition, Richard C. Larock. John Wiley & Sons, New York, N.Y. 1999), which can be converted conveniently converted in a one-pot reaction to the desired aminothiazoles I. We find it convenient to react the intermediately built benzoyl-amino-thiazol derivatives with amines (or their respective salts) or hydroylamines (or their respective salts), under various conditions with a coupling reagent suitable for such a transformation in the presence or absence of a solvent in the presence or absence of a base. Any coupling reagent commonly used in such a transformation can equally be employed, provided that they affect the reaction and show no adverse effect on the reaction or the reagents involved. Typical coupling reagents for amines and hydroxylamines include: CDI, HATU, EDCI or TBTU and the like. There is no particular restriction on the nature of the solvent to be employed, provided that it has no adverse effect on the reaction or the reagents involved and that it can dissolve the reagents, at least to some extent. Examples for suitable solvents or mixtures thereof include: DCM, DMF, THF, dioxane and the like. The reaction can take place over a wide range of temperatures, and the precise reaction temperature is not critical to the invention. We find it convenient to carry out the reaction with heating from ambient temperature to reflux. The time required for the reaction may also vary widely, depending on many factors, notably the reaction temperature and the nature of the reagents. However, a period of from 0.5 h to several days will usually suffice to yield the thiazole derivatives I. For reaction conditions described in literature affecting such reaction see for example: Comprehensive Organic Transformations: A Guide to Functional Group Preparations, 2nd Edition, Richard C. Larock. John Wiley & Sons, New York, N.Y. 1999.

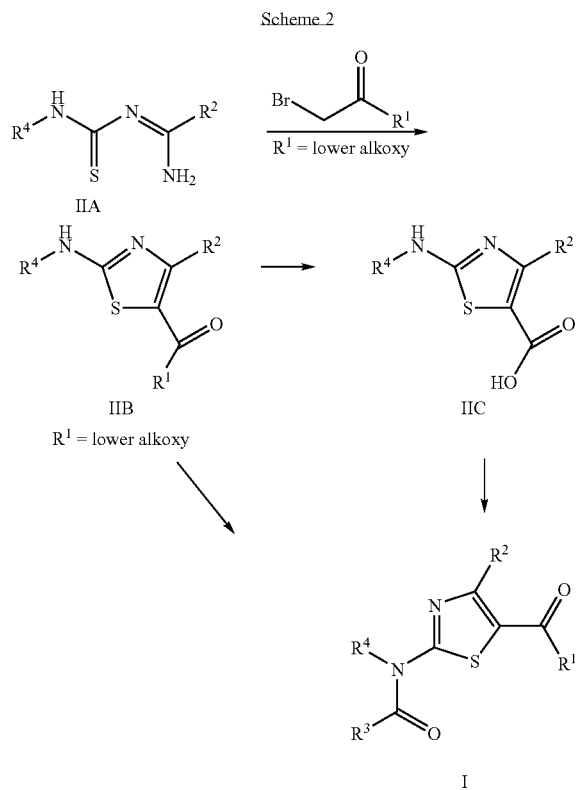

Some compounds of formula (I) may possess asymmetric centres and are therefore capable of existing in more than one stereoisomeric form. The invention thus also relates to compounds in substantially pure isomeric form at one or more asymmetric centres as well as mixtures, including racemic mixtures, thereof. Such isomers may be prepared by asymmetric synthesis, for example using chiral intermediate, or mixtures may be resolved by conventional mehtods, eg., chromatography (chromatography with a chiral adsorbens or eluent), or use of a solving agent.

It will be appreciated, that the compounds of general formula (I) in this invention may be derivatised at functional groups to provide derivatives which are capable of conversion back to the parent compound in vivo.

As described above, the compounds of formula (I) or pharmaceutically acceptable salts thereof can be used as therapeutically active substances, especially as therapeutically active substances for the treatment and/or prophylaxis of diseases which are associated with the modulation of the CB1 receptors. In one embodiment, the invention therefore relates to compounds as defined above for use as therapeutic active substances, particularly as therapeutic active substances for the treatment and/or prophylaxis of diseases which are associated with the modulation of CB1 receptors.

The invention also relates to pharmaceutical compositions comprising a compound as defined above and a pharmaceutically acceptable carrier and/or adjuvant.

In another embodiment, the invention relates to a method for the treatment and/or prophylaxis of diseases which are associated with the modulation of CB1 receptors, which method comprises administering a compound as defined above to a human being or animal.

The invention further relates to the use of compounds as defined above for the treatment and/or prophylaxis of diseases which are associated with the modulation of CB1 receptors.

In addition, the invention relates to the use of compounds as defined above for the preparation of medicaments for the treatment and/or prophylaxis of diseases which are associated with the modulation of CB1 receptors. Such medicaments comprise a compound as defined above.

In this context, the expression 'diseases associated with modulation of CB1 receptors' means diseases which can be treated and/or prevented by modulation of CB1 receptors. Such diseases encompass, but are not limited to, psychic disorders, especially anxiety and anxiety disorders, psychosis, schizophrenia, depression, substance abuse disorders including abuse of psychotropes, for example for the abuse and/or dependence of substances, including alcohol dependency and nicotine dependency, neuropathies, migraine, stress, epilepsy, dyskinesias, Parkinson's disease, amnesia, memory and cognitive disorders, senile dementia, Alzheimer's disease, eating disorders, obesity, diabetes type II or non insulin dependent diabetes (NIDD), gastrointestinal diseases, vomiting, diarrhea, urinary disorders, cardiovascular disorders, infertility disorders, inflammations, infections, cancer, demyelinisation related disorders, neuroinflammation, in particular in atherosclerosis, or the Guillain-Barre syndrome, viral encephalitis, cerebral vascular incidents and cranial trauma.

In a preferable aspect, the expression 'diseases associated with modulation of CB1 receptors' relates to eating disorders, obesity, diabetes type II or non insulin dependent diabetes (NIDD), neuroinflammation, diarrhea, abuse and/or dependence of a substances, including alcohol dependency and nicotine dependency. In a more preferable aspect, the said term related to eating disorders, obesity, diabetes type II or non insulin dependent diabetes (NIDD), abuse and/or dependence of a substances, including alcohol dependency and nicotine dependency, with obesity being especially preferred.

It is a further preferred object to provide a method of treatment or prevention of Type II diabetes (non-insulin dependent diabetes mellitus (NIDDM) in a human which comprises administration of a therapeutically effective amount of a compound according to formula (I) in combination or association with a therapeutically effective amount of a lipase inhibitor, particularly, wherein the lipase inhibitor is orlistat. Also an object of the invention is the method as described above for the simultaneous, separate or sequential administration of a compound according to formula (I) and a lipase inhibitor, particularly tetrahydrolipstatin.

It is a further preferred object to provide a method for the treatment or prevention of obesity and obesity related disorders which comprises administration of a therapeutically effective amount of a compound according to formula (I) in combination or association with a therapeutically effective amount of other drugs for the treatment of obesity or eating disorders so that together they give effective relief. Suitable other drugs include but are not limited to anorectic agents, lipase inhibitors and selective serotonin reuptake inhibitors (SSRI). Combinations or associations of the above agents may be encompassing separate, sequential or simultaneous administration.

Preferable lipase inhibitor is tetrahydrolipstatin.

Suitable anorectic agents of use in combination with a compound of the present invention include, but are not limited to, aminorex, amphechloral, amphetamine, benzphetamine, chlorphentermine, clobenzorex, cloforex, clominorex, clortermine, cyclexedrine, dexfenfluramine, dextroamphetamine, diethylpropion, diphemethoxidine, N-ethylamphetallline, fenbutrazate, fenfluramine, fenisorex, fenproporex, fludorex, fluminorex, furfurylmethylamphetamine, levamfetamine, levophacetoperane, mazindol, mefenorex, metamfepramone, methamphetamine, norpseudoephedrine, pentorex, phendimetrazine, phenmetrazine, phentermine, phenylpropanolamine, picilorex and sibutramine, and pharmaceutically acceptable salts thereof.

Most preferable anorectic agents are sibutramine and phentermine.

Suitable selective serotonin reuptake inhibitors of use in combination with a compound of the present invention include: fluoxetine, fluvoxamine, paroxetine and sertraline, and pharmaceutically acceptable salts thereof.

Demonstration of additional biological activities of the compounds of the present invention may be accomplished through in vitro, ex vivo, and in vivo assays that are well known in the art. For example, to demonstrate the efficacy of a pharmaceutical agent for the treatment of obesity-related disorders such as diabetes, Syndrome X, or atherosclerotic disease and related disorders such as hypertriglyceridemia and hypercholesteremia, the following assays may be used.

Method for Measuring Blood Glucose Levels db/db mice (obtained from Jackson Laboratories, Bar Harbor, Me.) are bled (by either eye or tail vein) and grouped according to equivalent mean blood glucose levels. They are dosed orally (by gavage in a pharmaceutically acceptable vehicle) with the test compound once daily for 7 to 14 days. At this point, the animals are bled again by eye or tail vein and blood glucose levels are determined.

Method for Measuring Triglyceride Levels hApoAl mice (obtained from Jackson Laboratories, Bar Harbor, Me.) are bled (by either eye or tail vein) and grouped according to equivalent mean serum triglyceride levels. They are dosed orally (by gavage in a pharmaceutically acceptable vehicle) with the test compound once daily for 7 to 14 days. The animals are then bled again by eye or tail vein, and serum triglyceride levels are determined.

Method for Measuring HDL-Cholesterol Levels

To determine plasma HDL-cholesterol levels, hApoAl mice are bled and grouped with equivalent mean plasma HDL-cholesterol levels. The mice are orally dosed once daily with vehicle or test compound for 7 to 14 days, and then bled on the following day. Plasma is analyzed for HDL-cholesterol.

In addition, to demonstrate CNS activities of the compounds of the present invention, the following in vivo assays may be used.

Method for Testing Task Learning and Spatial Memory

The Morris Water Maze is routinely used to assess task learning and spatial memory (Jaspers et al., Neurosci. Lett. 117:149-153, 1990; Morris, J. Neurosci. Methods 11:47-60, 1984). In this assay, animals are placed in a water pool which is divided into quadrants. One platform is hidden in one of the quadrants. The animal is placed in the water pool and is expected to locate the hidden platform within a predetermined time. During a number of training trials, the animal learns the location of the platform and escape from the pool. The animal receives multiple trials in this task. Total distance traveled, number of trials to locate platform, latency to find platform, and the swimming path is recorded for each animal. The animal's learning ability is measured by the length of time or number of trials required to find the hidden platform. Memory deficit or improvement is determined by the number of trials or the latency to find the platform at predetermined delay time after acquisition. Leaning and memory may be measured by the number of times that the animal crosses the quadrant where the platform was located during the acquisition phase.

Method for Testing Drug Dependence

Self-administration in animals is a predictor of a compound's abuse potential in humans. Modifications to this procedure may also be used to identify compounds that prevent or block the reinforcing properties of drugs that have abuse potential. A compound that extinguishes the self-administration of a drug may prevent tnat drug's abuse or its dependence. (Ranaldi et al., Psychopharmacol. 161:442-448, 2002; Campbell et al., Exp. Clin. Psychopharmacol. 8:312-25, 2000). In a self-administration test, animals are placed in the operant chambers containing both an active and inactive lever. Each response on the active lever produces an infusion of either the test compound or a drug known to be self-administered. Presses on the inactive lever have no effect, but are also recorded. Animals are then trained to self-administer compound/drug over a set period of time by having drug access during each daily session. Illumination of the chamber house light signals the beginning of the session and the availability of the compound/drug. When the session ends, the house light is turned off. Initially, a drug infusion occurs with every press of the active lever. Once lever-pressing behavior has been established, the number of presses to produce a drug infusion is increased. After stable compound/drug self-administration is obtained, the effect of a second compound on the drug-reinforced behavior may be evaluated. Administration of this second compound prior to the session can either potentiate, extinguish, or produce no change to the self-administrating behavior.

The following tests were carried out in order to determine the activity of the compounds of formula (I).

The affinity of the compounds of the invention for cannabinoid CB1 receptors was determined using membrane preparations of human embryonic kidney (HEK) cells in which the human cannabis CB1 receptor is transiently transfected using the Semliki Forest Virus system in conjunction with [3H]-CP-55,940 as radioligand. After incubation of a freshly prepared cell membrane preparation with the [3H]-ligand, with or without addition of compounds of the invention, separation of bound and free ligand was performed by filtration over glassfiber filters. Radioactivity on the filter was measured by liquid scintillation counting.

The affinity of the compounds of the invention for cannabinoid CB2 receptors was determined using membrane preparations of human embryonic kidney (HEK) cells in which the human cannabis CB2 receptor is transiently transfected using the Semliki Forest virus system in conjunction with [3H]-CP-55,940 as radioligand. After incubation of a freshly prepared cell membrane preparation with the [3H]-ligand, with or without addition of compounds of the invention, separation of bound of bound and free ligand was performed by filtration over glassfiber filters. Radioactivity on the filter was measured by liquid scintilation counting.

The cannabinoid CB1 antagonistic activity of compounds of the invention was determined by functional studies using CHO cells in which human cannabinoid CB1 receptors are stably expressed (see M. Rinaldi-Carmona et. al., J. Pharmacol. Exp. Ther. 278 (1996) 871). The stable expression of the human cannabinoid receptor in cell systems was first described in Nature, 1990, 346, 561-564 (CB1) and Nature 1993, 365, 61-65 (CB2) respectively. Adenylyl cyclase was stimulated using forskolin and measured by quantifying the amount of accumulated cyclic AMP. Concomitant activation of CB1 receptors by CB1 receptor agonists (e.g. CP-55,940 or (R)-WIN-55212-2) can attenuate the forskolin-induced accumulation of cAMP in a concentration dependent manner. This CB1 receptor mediated response can be antagonised by CB1 receptor antagonists such as the compounds of the invention.

The compounds of formula (I) show an excellent affinity for the CB1 receptor, determined with the experimental conditions described in Devane et.al. Mol. Pharmacol. 34 (1988) 605-613. The compounds of the present invention or the pharmaceutically acceptable salts or solvates are antagonists and selective for the CB1 receptor with affinities below $IC_{50}=5$ μM, preferable below $IC_{50}=2$ μM. They exhibit at least a 10 fold selectivity against the CB2 receptor.

| Compound of Example | $IC_{50}$ [μM] |
|---|---|
| 2 | 0.51 |
| 6 | 0.61 |
| 11 | 0.81 |
| 18 | 0.85 |
| 27 | 0.52 |
| 33 | 0.55 |
| 43 | 0.81 |
| 95 | 0.26 |
| 138 | 0.43 |
| 147 | 0.49 |

Effect of CB1 Receptor Antagonist/Inverse Agonist on CP 55,940-Induced Hypothermia in NMRI Mice Animals Male NMRI mice were used in this study and were obtained from Research Consulting Company Ltd (RCC) of Fillinsdorf (Switzerland). Mice, weighing 30-31 g were used in this study. Ambient temperature is approximately 20-21° C. and relative humidity 55-65%. A 12 hours light-dark cycle is maintained in the rooms with all tests being performed during the light phase. Access to tap water and food are ad libitum.

Method

All measurements were made between 12:00 am and 5:00 pm. Mice were brought in this environment and habituated for at least two hours before the start of the experiment. They had always free access to food and water. For each dose, 8 mice were used. Rectal body temperature measurements were recorded by mean of a rectal probe (RET2 of Physitemp) and digital thermometer (Digi-sense no 8528-20 of Cole Parmer, Chicago USA). The probe was inserted about 3.5 cm in each mouse.

The body temperature was taken 15 min before administration of either Vehicle or CB1 receptor antagonist/inverse agonist. 30 or 90 min after i.p. or p.o. administration of this compound, respectively, rectal body temperature was recorded in order to evaluate any influence of the compound itself. The CB receptor agonist CP 55,940 (0.3 mg/kg) was immediately administered intravenously, then 20 min after i.v. administration of CP 55940, body temperature was again measured.

The in vivo activity of compounds of formula (1) was assessed for their ability to regulate feeding behaviour by recording food consumption in food deprived animals.

Rats were trained to have access to food for 2 h per day and were food deprived for 22 h. When they were trained under this schedule, the amount of food taken every day during these 2 h food intake session was consistent day after day.

To test the ability of compounds of formula (1) to decrease food intake, 8 animals were used in a cross-over study. Rats were individually housed in Plexiglas boxes with a grid on the floor and a paper was placed below the cage floor to collect any spillage. A food dispenser (becher) filled with a pre-weighed amount of food was presented to them for 2 h. At the end of the food intake session, rats returned to their home cage. Each rat was weighed before the start of the experiment and the amount of food consumed during this 2 h food intake session was recorded. Either various doses of test compound or vehicle was administered orally 60 min before the 2 h food intake session. A positive control Rimonabant (SR141716) was included in the experiment. An Anova analysis with repeated measures was used followed by a posthoc test Student Neumann-Keuls. *$P<0.05$ compared to Saline-treated rats.

Furthermore the utility of compounds of formula (1) in diseases or disorders may be demonstrated in animal disease models that have been reported in the literature. The following are examples of such animal disease models: a) reduction of sweet food intake in marmosets (Behavioural Pharm, 1998, 9,179-181); b) reduction of sucrose and ethanol intake in mice (Psychopharm. 1997, 132, 104-106); c) increased motor activity and place conditioning in rats (Psychopharm. 1998, 135, 324-332; Psychopharmacol 2000, 151: 25-30); d) spontaneous locomotor activity in mice (J. Pharm. Exp. Ther. 1996, 277, 586-594); e) reduction in opiate self-administration in mice (Sci. 1999, 283, 401-404);

The compounds of formula (I) and/or their pharmaceutically acceptable salts can be used as medicaments, e.g. in the form of pharmaceutical preparations for enteral, parenteral or topical administration. They can be administered, for example, perorally, e.g. in the form of tablets, coated tablets, dragees, hard and soft gelatine capsules, solutions, emulsions or suspensions, rectally, e.g. in the form of suppositories, parenterally, e.g. in the form of injection solutions or infusion solutions, or topically, e.g. in the form of ointments, creams or oils. Oral administration is preferred.

The production of the pharmaceutical preparations can be effected in a manner which will be familiar to any person skilled in the art by bringing the described compounds of formula (I) and/or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragees and hard gelatine capsules. Suitable carrier materials for soft gelatine capsules are, for example, vegetable oils, waxes, fats and semi-solid and liquid polyols (depending on the nature of the active ingredient no carriers might, however, be required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavour-improving agents, salts for varying the osmotic pressure, buffer substances, solubilizers, colorants and masking agents and antioxidants come into consideration as pharmaceutical adjuvants.

The dosage of the compounds of formula (I) can vary within wide limits depending on the disease to be controlled, the age and the individual condition of the patient and the mode of administration, and will, of course, be fitted to the individual requirements in each particular case. For adult patients a daily dosage of about 1 to 1000 mg, especially about 1 to 100 mg, comes into consideration. Depending on severity of the disease and the precise pharmacokinetic profile the compound could be administered with one or several daily dosage units, e.g. in 1 to 3 dosage units.

The pharmaceutical preparations conveniently contain about 1-500 mg, preferably 1-100 mg, of a compound of formula (I).

The following Examples serve to illustrate the present invention in more detail. They are, however, not intended to limit its scope in any manner.

EXAMPLES

MS=mass spectrometry; aq=aqueous, THF=tetrahydrofuran, DMF=dimethylformamide, DCM=dichloromethane.

Example 1

Starting Materials

Example A 2-(3,4-Dimethoxy-phenylamino)-thiazole-4-carboxylic acid ethyl ester; hydrobromide A mixture of 10 g (47.1 mmol) (3,4-Dimethoxy-phenyl)-thiourea and 5.93 ml (47.1 mmol) ethyl bromopyruvate in 50 ml ethanol was heated to 60° C. for 16 h. The precipitate was filtered off and washed with small portions of cold ethanol to yield after drying 15.7 g (85.6%) of the title compound as crystalline solid. MS (m/e): 308.6 (MH$^+$, 100%)

Example B 2-(4-Chloro-phenylamino)-thiazole-4-carboxylic acid ethyl ester; hydrobromide A mixture of 10 g (53.5 mmol) 4-Chloro-phenyl-thiourea and 6.74 ml (53.5 mmol) ethyl bromopyruvate in 50 ml ethanol was heated to 60° C. for 16 h. The precipitate was filtered off and washed with small portions of cold ethanol to yield after drying 11.5 g (59.2%) of the title compound as crystalline solid. MS (m/e): 282.6 (MH$^+$)

Example C

2-[(2-Chloro-benzoyl)-(4-chloro-phenyl)-amino]-thiazole-4-carboxylic acid ethyl ester A mixture of 2.58 g (7.1 mmol) 2-(4-Chloro-phenylamino)-thiazole-4-carboxylic acid ethyl ester; hydrobromide, 1.87 g (10.7 mmol) 2-Chlorobenzoyl chloride and 2.96 ml (21.4 mmol) NEt$_3$ in 30 ml DCM was stirred at room temperature for 24 h. After evaporation of the volatiles the residue was taken up in MeOH and purified with flash column chromatography on silica eluting with a gradient of heptane/ethyl acetate and to yield after evaporation of the product fractions 2.21 g (74%) of the title compound. MS (m/e): 421.0 (MH$^+$, 100%)

Example D

2-[(4-Chloro-phenyl)-(2,4-dichloro-benzoyl)-amino]-thiazole-4-carboxylic acid ethyl ester A mixture of 2.58 g (7.1 mmol) 2-(4-Chloro-phenylamino)-thiazole-4-carboxylic acid ethyl ester; hydrobromide, 2.24 g (10.7 mmol) 2,4-Dichlorobenzoyl chloride and 2.96 ml (21.4 mmol) NEt$_3$ in 30 ml DCM was stirred at room temperature for 24 h. After evaporation of the volatiles the residue was taken up in MeOH and purified with flash column chromatography on silica eluting with a gradient of heptane/ethyl acetate to yield after evaporation of the product fractions 2.81 g (87%) of the title compound. MS (m/e): 457.1 (MH$^+$, 100%)

Example E

2-[(2,4-Dichloro-benzoyl)-(3,4-dimethoxy-phenyl)-amino]-thiazole-4-carboxylic acid A mixture of 2.25 g (4.68 mmol) 2-[(2,4-Dichloro-benzoyl)-(3,4-dimethoxy-phenyl)-amino]-thiazole-4-carboxylic acid ethyl ester, 2.5 ml acetic acid and 7.5 ml HCl conc. in 10 ml dioxane was heated to 60° C. for 2 h. The precipitate was filtered off and washed with dioxane to yield after drying 0.566 g (22%) of the title compound. MS (m/e): 453.0 (MH$^+$, 100%)

Example F

2-[(2-Chloro-benzoyl)-(3,4-dimethoxy-phenyl)-amino]-thiazole-4-carboxylic acid

A mixture of 2.09 g (4.68 mmol) 2-[(2-Chloro-benzoyl)-(3,4-dimethoxy-phenyl)-amino]-thiazole-4-carboxylic acid ethyl ester, 2.5 ml acetic acid and 7.5 ml HCl conc. in 10 ml dioxane was heated to 60° C. for 2 h. The mixture was subjected to reversed phase HPLC purification eluting with an acetonitrile/water gradient to yield after evaporation of the product fractions 1.1 g (56%) of the title compound. MS (m/e): 419.2 (MH$^+$, 100%)

Example G

2-[(4-Chloro-phenyl)-(2,4-dichloro-benzoyl)-amino]-thiazole-4-carboxylic acid A mixture of 2.13 g (4.68 mmol) 2-[(2,4-Dichloro-benzoyl)-(4-chloro-phenyl)-amino]-thiazole-4-carboxylic acid ethyl ester, 2.5 ml acetic acid and 7.5 ml HCl conc. in 10 ml dioxane was heated to 60° C. for 2 h. The mixture was subjected to reversed phase HPLC purification eluting with an acetonitrile/water gradient to yield after evaporation of the product fractions 0.955 g (48%) of the title compound. MS (m/e): 429.1 (MH$^+$, 100%)

Example H

2-[(2-Chloro-benzoyl)-(4-chloro-phenyl)-amino]-thiazole-4-carboxylic acid

A mixture of 1.97 g (4.68 mmol) 2-[(2-Chloro-benzoyl)-(4-chloro-phenyl)-amino]-thiazole-4-carboxylic acid ethyl ester, 2.5 ml acetic acid and 7.5 ml HCl conc. in 10 ml dioxane was heated to 60° C. for 2 h. The mixture was subjected to reversed phase HPLC purification eluting with an acetonitrile/water gradient to yield after evaporation of the product fractions 1.02 g (56%) of the title compound. MS (m/e): 393.1 (MH$^+$, 100%)

Example I

2-(4-Chloro-phenylamino)-5-methyl-thiazole-4-carboxylic acid ethyl ester

A mixture of 5.32 g (28.5 mmol) 4-Chloro-phenyl-thiourea and 5.35 g (32.5 mmol) α-Methylchloropyruvate (*J. Chem Soc. Perkin* 1, 1982, 2,159) in 50 ml MeOH was heated under reflux for 4 h and cooled to room temperature and 25% aq. NH$_4$OH was added. The mixture was extracted 3× with 50 ml DCM and the combined organic layers were washed 2× with 30 ml water, dried with MgSO$_4$ and evaporated under reduced pressure. The residue was recrystallised from EtOH to yield 5.30 g (66%) of the title compound as white crystals.
MS (m/e): 282.7 (MH$^+$, 100%)

Example J

2-(3,4-Dimethoxy-phenylamino)-5-methyl-thiazole-4-carboxylic acid ethyl ester A mixture of 5.97 g (28.1 mmol) (3,4-Dimethoxy-phenyl)-thiourea and 5.26 g (0.32 mmol) a-Methylchloropyruvate (*J. Chem Soc. Perkin* 1, 1982, 2, 159) in 50 ml MeOH was heated under reflux for 4 h and cooled to room temperature and 25% aq. NH4OH was added. The mixture was extracted 3× with 50 ml DCM and the combined organic layers were washed 2× with 30 ml water, dried with MgSO$_4$ and evaporated under reduced pressure. The residue was recrystallised from EtOH to yield 4.23 g (49%) of the title compound as white crystals. MS (m/e): 309.5 (MH$^+$, 100%)

Example K

2-(4-Chloro-phenylamino)-5-methyl-thiazole-4-carboxylic acid

A mixture of 5.1 g (18 mmol) 2-(4-Chloro-phenylamino)-5-methyl-thiazole-4-carboxylic acid ethyl ester and 10.8 ml 5M aq. KOH in 50 ml THF was heated to 50° C. for 16 h. After evaporation of the volatiles 100 ml water and 6 ml HOAc was added and the mixture was extracted 3× with 500 ml ethyl acetate. The combined organic layers were washed 3× with 200 ml water and concentrated at 40° C. under reduced pressure until precipitation started. After cooling to room temperature the crystals were filtered off, washed 3× with 10 ml ethyl acetate and dried to yield 2.16 g (44.5%) of the title compound. MS (m/e): 453.0 (MH$^+$, 100%)

Example L

2-(3,4-Dimethoxy-phenylamino)-5-methyl-thiazole-4-carboxylic acid

A mixture of 4.1 g (12.7 mmol) 2-(3,4-Dimethoxy-phenylamino)-5-methyl-thiazole-4-carboxylic acid ethyl ester and 7.6 ml 5M aq. KOH in 50 ml THF was heated to 50° C. for 16 h. After evaporation of the volatiles 100 ml water and 6 ml HOAc was added and the mixture was extracted 3× with 500 ml ethyl acetate. The combined organic layers were washed 3× with 200 ml water and concentrated at 40° C. under reduced pressure until precipitation started. After cooling to room temperature the crystals were filtered off, washed 3× with 10 ml ethyl acetate and dried to yield 2.16 g (44.5%) of the title compound. MS (m/e): 295.3 (MH$^+$, 100%)

Example M

2-[(4-Chloro-phenyl)-(2,4-dichloro-benzoyl)-amino]-5-methyl-thiazole-4-carboxylic acid A mixture of 2.0 g (7.4 mmol) 2-(4-Chloro-phenylamino)-5-methyl-thiazole-4-carboxylic acid, 1.56 ml (11.1 mmol) 2,4-Dichlorobenzoyl chloride and 3.09 ml (22.3 mmol) NEt$_3$ in 30 ml DCM was stirred at room temperature for 2 h. After removal of all volatiles the resulting yellow foam was used without further purification in the consecutive step. MS (m/e): 441.0 (MH$^+$, 100%)

Example N

2-[(2,4-Dichloro-benzoyl)-(3,4-dimethoxy-phenyl)-amino]-5-methyl-thiazole-4-carboxylic acid A mixture of 2.74 g (9.3 mmol) 2-(3,4-Dimethoxy-phenylamino)-5-methyl-thiazole-4-carboxylic acid, 1.95 ml (14 mmol) 2,4-Dichlorobenzoyl chloride and 3.88 ml (27.9 mmol) NEt$_3$ in 30 ml DCM was stirred at room temperature for 5 min and 50 ml water was added and the mixture was stirred at room temperature for 16 h. After removal of all volatiles the residue was extracted with DCM and evaporated under reduced pressure to yield 4.18 g of amorphous light brown solid which was used without further purification in the consecutive step. MS (m/e): 467.2 (MH$^+$, 100%)

Example O

2-(3,4-Dimethoxy-phenylamino)-thiazole-5-carboxylic acid ethyl ester

A mixture of 10 g (51.2 mmol) 4-isothiocyanato-1,2-dimethoxybenzene in 51 ml THF at 0° C. was treated with 5.1 g (63.3 mmol) formamidine hydrochloride and 63.3 ml 1N NaOH and allowed to stir for 3 h after which the mixture was concentrated. 500 ml ethyl acetate and 100 ml water was added and the precipitate was filtered off and dried to yield the intermediate 1-[1-Amino-methylidene]-3-(3,4-dimethoxy-phenyl)-thiourea (MH$^+$ 240.2) which was used without further purification. The thiourea was taken up in 50 ml THF and treated with 8.55 g (51.2 mmol) ethyl bromoacetate and 14.2 ml NEt$_3$ and stirred at room temperature for 16 h and at 50° C. for 8 h. The mixture was concentrated and extracted with CHCl$_3$. The organic layer was washed with aqueous Na$_2$CO$_3$ (1M) and saturated NaCl solution, dried with MgSO4 and evaporated. The residue was purified with reversed phase preparative HPLC to yield 4.04 g (26%) of the title compound.

MS (m/e): 309.2 (MH$^+$, 100%)

Example P

2-(4-Chloro-phenylamino)-thiazole-5-carboxylic acid ethyl ester

A mixture of 10 g (51.2 mmol) 4-isothiocyanato-4-chloro benzene in 51 ml THF at 0° C. was treated with 5.15 g (64.02 mmol) formamidine hydrochloride and 64 ml 1N NaOH and allowed to stirr for 5 h after which the mixture was concentrated. 500 ml ethyl acetate and 100 ml water was added and the precipitate was filtered off, washed with water and dried to yield the intermediate 1-[1-Amino-methylidene]-3-(4-chloro-phenyl)-thiourea (MH$^+$ 213.5) which was used without further purification. The thiourea was taken up in 50 ml THF and treated with 8.55 g (51.2 mmol) ethyl bromoacetate and 15.3 ml NEt$_3$ and stirred at 50° C. for 18 h. The mixture was concentrated and extracted with CHCl$_3$. The organic layer was washed with aqueous Na$_2$CO$_3$ (1M) and saturated NaCl solution, dried with MgSO4 and evaporated. The residue was purified with column chromatography on silica to yield 3.48 g (22%) of the title compound.

MS (m/e): 282.8 (MH$^+$, 100%)

Example Q

2-(3,4-Dimethoxy-phenylamino)-thiazole-5-carboxylic acid

A mixture of 3.9 g (12.78 mmol) 2-(3,4-Dimethoxy-phenylamino)-thiazole-5-carboxylic acid ethyl ester and 12.78 ml 5M KOH in 23.5 ml THF was heated to 55° C. for 22 h. After acidification with HCl aq. The mixture was extracted with ethyl acetate and the combined organic layers washed with water, dried with MgSO4 and evaporated to dryness. Additionally precipitaed material from the aqueous phase was filtered off and dried. 2.39 g (67%) of the title compound was obtained as beige crystals. MS (m/e): 279.0 (M–H, 100%)

Example R

2-(4-Chloro-phenylamino)-thiazole-5-carboxylic acid

A mixture of 3.0 g (11.1 mmol) 2-(4-Chloro-phenylamino)-thiazole-5-carboxylic acid ethyl ester and 6.7 ml 5M KOH in 50 ml THF and 10 ml MeOH was heated to 50° C. for 4 h and subsequently concentrated. The residue was taken up in water, acidified with acetic acid and extracted with ethyl acetat. The combined organic layers were washed with water, dried with MgSO4 and evaporated. The residue was recrystallised from ethyl acetate to obrain 2.0 g (70%) of the title compound as white crystals. (m/e): 254.9 (M+H$^+$, 100%)

Example S

2-(4-(Trifluoromethoxy)phenylamino)-thiazole-4-carboxylic acid

A mixture of 12.9 g (54.6 mmol) [4-(trifluoromethoxy)phenyl]-thiourea, and 9.3 g (55.7 mmol) bromopyruvic acid in 70 ml ethanol was heated to 60° C. for 1 h. The precipitate was filtered off and washed with small portions of cold ethanol to yield after drying 8.9 g (53%) of the title compound as crystalline solid.

MS (m/e): 303.1 (M–H)

Example T

2-[(2-Chloro-benzoyl)-(4-trifluoromethoxyphenyl)-amino]-thiazole-4-carboxylic acid A mixture of 2.0 g (6.6 mmol) 2-(4-(trifluoromethoxy)phenylamino)-thiazole-4-carboxylic acid, 2.87 g (16.4 mmol) 2-chlorobenzoyl chloride and 0.92 g (6.6 mmol) potassium carbonate in 50 mL THF was stirred at 50° C. for 48 h. After evaporation of the volatiles the residue was partitioned between water and ethyl acetate. Organic phases were pooled, dried with MgSO$_4$ and the solvent was removed in vacuo. Crystallisation from n-heptane yielded 2.1 g (72%) of the title compound.

MS (m/e): 441.0, 443.0 (M–H)

Example U

2-[(2-Chloro-4-fluoro-benzoyl)-(4-trifluoromethoxyphenyl)-amino]-thiazole-4-carboxylic acid A mixture of 2.0 g (6.6 mmol) 2-(4-(trifluoromethoxy)phenylamino)-thiazole-4-carboxylic acid, 3.17 g (16.4 mmol) 2-chloro-4-fluorobenzoyl chloride and 0.92 g (6.6 mmol) potassium carbonate in 50 mL THF was stirred at 50° C. for 48 h. After evaporation of the volatiles the residue was partitioned between water and ethyl acetate. Organic phases were pooled, dried with MgSO$_4$ and the solvent was removed in vacuo. Crystallisation from n-heptane/ethyl acetate yielded 3.4 g of the title compound which was used without further purification.

MS (m/e): 459.0, 461.0 (M–H)

Example V

2-[(2,4-Dichloro-benzoyl)-(4-trifluoromethoxyphenyl)-amino]-thiazole-4-carboxylic acid A mixture of 2.0 g (6.6 mmol) 2-(4-(trifluoromethoxy)phenylamino)-thiazole-4-carboxylic acid, 3.44 g (16.4 mmol) 2,4-dichloro-benzoyl chloride and 0.92 g (6.6 mmol) potassium carbonate in 50 mL THF was stirred at 50° C. for 48 h. After evaporation of the volatiles the residue was partitioned between water and ethyl acetate. Organic phases were pooled, dried with MgSO$_4$ and the solvent was removed in vacuo. Crystallisation from n-heptane/ethyl acetate yielded 2.5 g (79%) of the title compound.

MS (m/e): 474.8, 476.8 (M–H)

Example W

1-(4-Chloro-3-methoxyphenyl)-thiourea

Benzoyl isothiocyanate (8.8 mL, 64 mmol) was added dropwise to a solution of 4-chloro-3-methoxy-benzenamine (10 g, 63 mmol) in 160 mL THF. The mixture was stirred at room temperature for 40 minutes, volatiles were removed and the residue was dissolved in 400 mL methanol. A solution of potassium carbonate (26.3 g, 190 mmol) in 200 mL water was added and the mixture was stirred at room temperature for 90 minutes. The tide product (13.5 g, 98%) precipitated after removal of 450 mL of the solvents.

MS (m/e): 216.0, 218.0 (M$^+$)

Example X

2-(4-Chloro-3-methoxy-phenylamino)-thiazole-4-carboxylic acid

A mixture of 7.8 g (36 mmol) 1-(4-chloro-3-methoxyphenyl)-thiourea, and 6.2 g (36 mmol) bromopyruvic acid in 80 ml ethanol was heated to 60° C. for 1 h. The precipitate was filtered off and washed with small portions of cold ethanol to yield after drying 10.0 g (98%) of the title compound as crystalline solid.
MS (m/e): 283.1 (M−H)

Example Y

2-[(2,4-Dichloro-benzoyl)-(4-chloro-3-methoxy-phenyl)-amino]-thiazole-4-carboxylic acid A mixture of 5.0 g (17 mmol) 2-(4-chloro-3-methoxy-phenylamino)-thiazole-4-carboxylic acid, 9.2 g (44 mmol) 2,4-dichloro-benzoyl chloride and 2.45 g (17.7 mmol) potassium carbonate in 250 mL THF was stirred at 50° C. for 18 h. After evaporation of the volatiles the residue was partitioned between water and ethyl acetate. Organic phases were pooled, dried with MgSO4 and the solvent was removed in vacuo. Crystallisation from n-heptane/ethyl acetate yielded 5.8 g (72%) of the title compound.
MS (m/e): 455.1, 457.1 (M−H)

Example Z

2-(4-Chloro-3-methoxy-phenylamino)-5-methyl-thiazole-4-carboxylic acid methyl ester A mixture of 8.7 g (40.1 mmol) 1-(4-chloro-3-methoxyphenyl)-thiourea and 7.5 g (0.44 mmol) α-methylchloropyruvate (J. Chem Soc. Perkin 1, 1982, 2, 159) in 140 ml methanol was heated under reflux for 5 h, cooled to room temperature and volatiles were removed. The residue was dissolved in dichloromethane and washed successively with 25% aq. ammonia and water. Water phases were extracted thrice with dichloromethane, the organic phases were pooled, dried with MgSO4 and the solvent removed in vacuo. The residue was purified by chromatography on silica gel with heptane/ethyl acetate (1:2) to give 6.2 g (50%) of the title compound as colorless solid.
MS (m/e): 313.1, 315.1 (MH+)

Example AA

2-(4-Chloro-3-methoxy-phenylamino)-5-methyl-thiazole-4-carboxylic acid

A mixture of 6.0 g (19 mmol) 2-(4-chloro-3-methoxy-phenylamino)-5-methyl-thiazole-4-carboxylic acid methyl ester and 11.5 mL 5M aq. KOH in 60 mL THF was heated to 50° C. for 3 h. Upon cooling to room temperature the potassium salt of the product precipitated and was filtered off. This solid was dissolved in a mixture of water (250 mL) and acetic acid (12 mL) and the solution was extracted thrice with ethyl acetate. Organic phases were pooled washed with water and the solvent was removed. The residue was stirred with dichloromethane/n-heptane (1:1; 30 mL) and the solid was isolated by filtration. Residual solvent was removed in vacuo to yield 4.4 g (77%) of the title compound.
MS (m/e): 297.1, 299.1 (M−H)

Example AB

2-[(2,4-Dichloro-benzoyl)-(4-chloro-3-methoxy-phenyl)-amino]-5-methyl-thiazole-4-carboxylic acid A mixture of 4.3 g (14 mmol) 2-(4-chloro-3-methoxy-phenylamino)-5-methyl-thiazole-4-carboxylic acid, 7.5 g (35 mmol) 2,4-dichloro-benzoyl chloride and 2.01 g (14.5 mmol) potassium carbonate in 200 mL THF was stirred at 50° C. for 18 h. After evaporation of the volatiles the residue was partitioned between water and ethyl acetate. Organic phases were pooled, dried with MgSO4 and the solvent was removed in vacuo. Crystallisation from n-heptane/ethyl acetate yielded 6.6 g (97%) of the title compound.
MS (m/e): 469.0, 471.0 (M−H)

Example 2

2-[(2,4-Dichloro-benzoyl)-(3,4-dimethoxy-phenyl)-amino]-thiazole-4-carboxylic acid ethyl ester

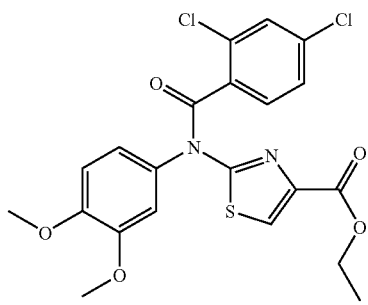

A mixture of 2.18 g (7.1 mmol) 2-(3,4-Dimethoxy-phenylamino)-thiazole-4-carboxylic acid ethyl ester; hydrobromide, 2.24 g (10.7 mmol) 2,4-Dichlorobenzoyl chloride and 2.96 ml (21.4 mmol) NEt3 in 30 ml DCM was stirred at room temperature for 24 h. After evaporation of the volatiles the residue was taken up in MeOH and purified with flash column chromatography on silica eluting with a gradient of heptane/ethyl acetate to yield after evaporation of the product fractions 0.75 g (22%) of the title compound. MS (m/e): 481.1 (MH+, 100%)

Example 3

2-[(2-Chloro-benzoyl)-(3,4-dimethoxy-phenyl)-amino]-thiazole-4-carboxylic acid ethyl ester

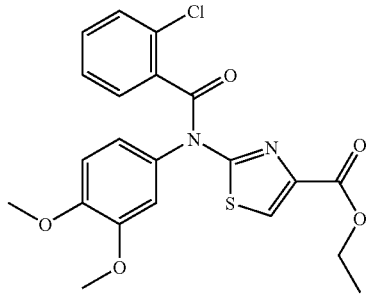

A mixture of 2.18 g (7.1 mmol) 2-(3,4-Dimethoxy-phenylamino)-thiazole-4-carboxylic acid ethyl ester; hydrobromide, 1.87 g (10.7 mmol) 2-Chlorobenzoyl chloride and 2.96 ml (21.4 mmol) NEt3 in 30 ml DCM was stirred at room temperature for 24 h. After evaporation of the volatiles the residue was taken up in MeOH and purified with flash column chromatography on silica eluting with a gradient of heptane/ethyl acetate to yield after evaporation of the product fractions 1.58 g (50%) of the title compound. MS (m/e): 446.9 (MH+, 100%)

Example 4

2,4-Dichloro-N-(4-chloro-phenyl)-N-[4-(morpholine-4-carbonyl)-thiazol-2-yl]-benzamide

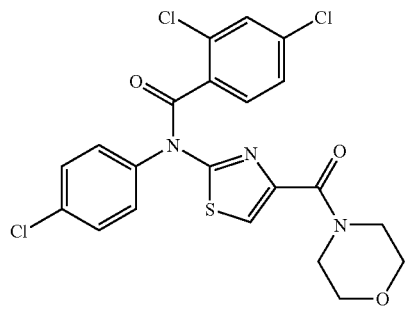

A mixture of 30 mg (0.7 mmol) 2-[(4-Chloro-phenyl)-(2,4-dichloro-benzoyl)-amino]-thiazole-4-carboxylic acid 15.2 mg (0.175 mmol) morpholine and 14.8 mg (0.91 mmol) 1,1'-Carbonyldimidazole in 1 ml DMF was stirred for 16 h at room temperature. The mixture was subjected to reversed phase HPLC purification eluting with an acetonitrile/water gradient to yield after evaporation of the product fractions 15.4 mg (44%) of the title compound. MS (m/e): 496.1 (MH+, 100%)

According to the procedure described for the synthesis of Example 4 further derivatives have been synthesised from 2-[(2,4-Dichloro-benzoyl)-(3,4-dimethoxy-phenyl)-amino]-thiazole-4-carboxylic acid, 2-[(2-Chloro-benzoyl)-(3,4-dimethoxy-phenyl)-amino]-thiazole-4-carboxylic acid, 2-[(4-Chloro-phenyl)-(2,4-dichloro-benzoyl)-amino]-thiazole-4-carboxylic acid or 2-[(2-Chloro-benzoyl)-(4-chloro-phenyl)-amino]-thiazole-4-carboxylic acid and various commercially available amines and comprise Examples 5-Example 95 below.

Examples 5-95

The following compounds have been prepared in analogy to the process described in Example 4:

| Expl. No. | Structure | Systematic Name | Synthesised from: | MW found |
|---|---|---|---|---|
| 5 | 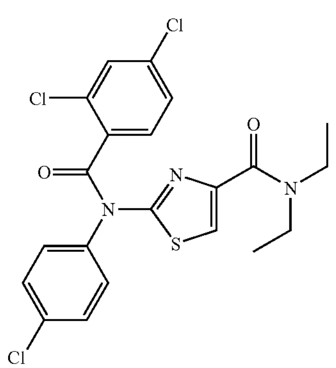 | 2-[(4-Chloro-phenyl)-(2,4-dichloro-benzoyl)-amino]-thiazole-4-carboxylic acid diethylamide | 2-[(4-Chloro-phenyl)-(2,4-dichloro-benzoyl)-amino]-thiazole-4-carboxylic acid and diethylamine | 482.3 |
| 6 | 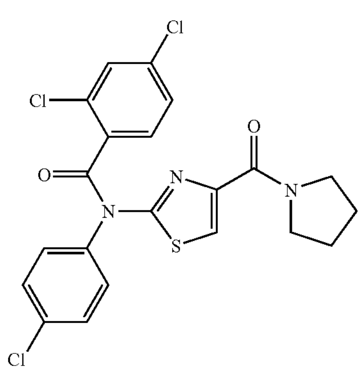 | 2,4-Dichloro-N-(4-chloro-phenyl)-N-[4-(pyrrolidine-1-carbonyl)-thiazol-2-yl]-benzamide | 2-[(4-Chloro-phenyl)-(2,4-dichloro-benzoyl)-amino]-thiazole-4-carboxylic acid and pyrrolidine | 482.2 |

| Expl. No. | Structure | Systematic Name | Synthesised from: | MW found |
|---|---|---|---|---|
| 7 | 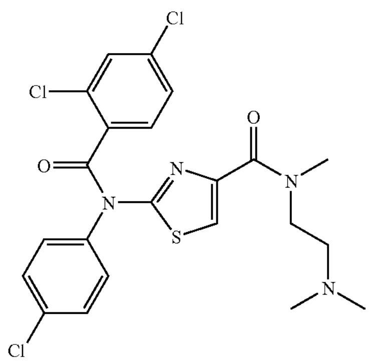 | 2-[(4-Chloro-phenyl)-(2,4-dichloro-benzoyl)-amino]-thiazole-4-carboxylic acid (2-dimethylamino-ethyl)-methyl-amide | 2-[(4-Chloro-phenyl)-(2,4-dichloro-benzoyl)-amino]-thiazole-4-carboxylic acid and trimethyl-ethane-1,2-diamine | 511.2 |
| 8 | 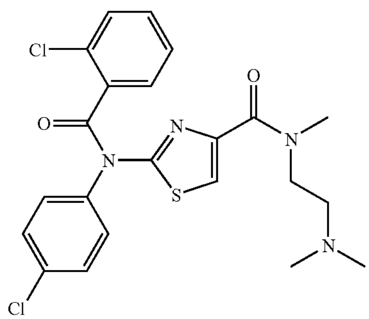 | 2-[(2-Chloro-benzoyl)-(4-chloro-phenyl)-amino]-thiazole-4-carboxylic acid (2-dimethylamino-ethyl)-methyl-amide | 2-[(2-Chloro-benzoyl)-(4-chloro-phenyl)-amino]-thiazole-4-carboxylic acid and trimethyl-ethane-1,2-diamine | 477.1 |
| 9 | 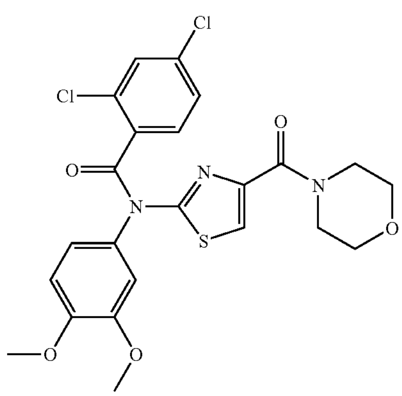 | 2,4-Dichloro-N-(3,4-dimethoxy-phenyl)-N-[4-(morpholine-4-carbonyl)-thiazol-2-yl]-benzamide | 2-[(3,4-Methoxy-phenyl)-(2,4-dichloro-benzoyl)-amino]-thiazole-4-carboxylic acid and morpholine | 522.2 |
| 10 | 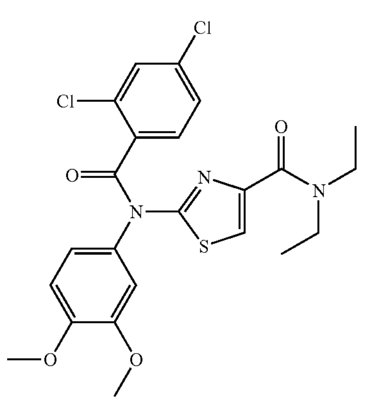 | 2-[(2,4-Dichloro-benzoyl)-(3,4-dimethoxy-phenyl)-amino]-thiazole-4-carboxylic acid diethylamide | 2-[(3,4-Methoxy-phenyl)-(2,4-dichloro-benzoyl)-amino]-thiazole-4-carboxylic acid and diethylamine | 508.3 |

-continued

| Expl. No. | Structure | Systematic Name | Synthesised from: | MW found |
|---|---|---|---|---|
| 11 | 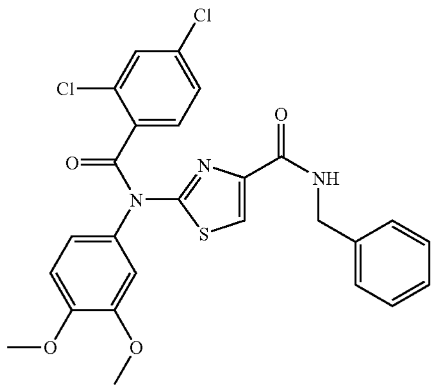 | 2-[(2,4-Dichloro-benzoyl)-(3,4-dimethoxy-phenyl)-amino]-thiazole-4-carboxylic acid benzylamide | 2-[(3,4-Methoxy-phenyl)-(2,4-dichloro-benzoyl)-amino]-thiazole-4-carboxylic acid and benzylamine | 542.2 |
| 12 | 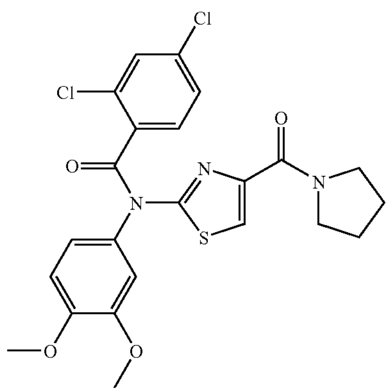 | 2,4-Dichloro-N-(3,4-dimethoxy-phenyl)-N-[4-(pyrrolidine-1-carbonyl)-thiazol-2-yl]-benzamide | 2-[(3,4-Methoxy-phenyl)-(2,4-dichloro-benzoyl)-amino]-thiazole-4-carboxylic acid and pyrrolidine | 506.3 |
| 13 | 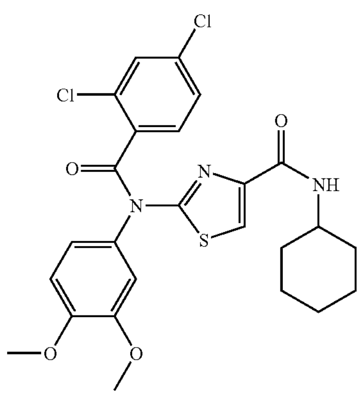 | 2-[(2,4-Dichloro-benzoyl)-(3,4-dimethoxy-phenyl)-amino]-thiazole-4-carboxylic acid cyclohexylamide | 2-[(3,4-Methoxy-phenyl)-(2,4-dichloro-benzoyl)-amino]-thiazole-4-carboxylic acid and cyclohexylamine | 534.2 |
| 14 | 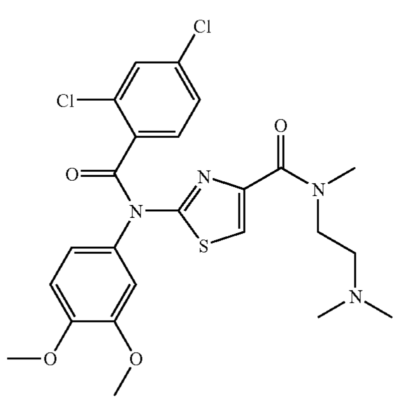 | 2-[(2,4-Dichloro-benzoyl)-(3,4-dimethoxy-phenyl)-amino]-thiazole-4-carboxylic acid (2-dimethylamino-ethyl)-methyl-amide | 2-[(3,4-Methoxy-phenyl)-(2,4-dichloro-benzoyl)-amino]-thiazole-4-carboxylic acid and trimethyl-ethane-1,2-diamine | 537.2 |

| Expl. No. | Structure | Systematic Name | Synthesised from: | MW found |
|---|---|---|---|---|
| 15 | 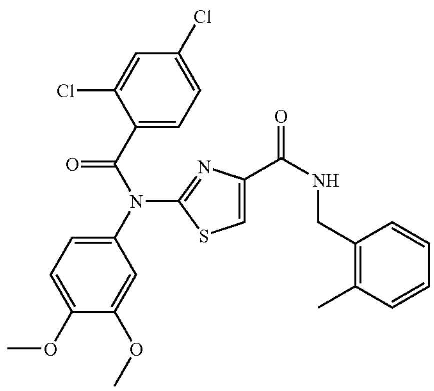 | 2-[(2,4-Dichloro-benzoyl)-(3,4-dimethoxy-phenyl)-amino]-thiazole-4-carboxylic acid 2-methyl-benzylamide | 2-[(3,4-Methoxy-phenyl)-(2,4-dichloro-benzoyl)-amino]-thiazole-4-carboxylic acid and 2-methyl-benzylamine | 556.2 |
| 16 | 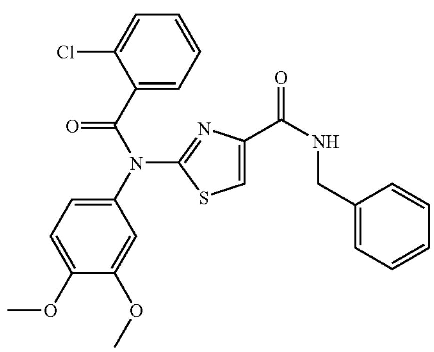 | 2-[(2-Chloro-benzoyl)-(3,4-dimethoxy-phenyl)-amino]-thiazole-4-carboxylic acid benzylamide | 2-[(3,4-Methoxy-phenyl)-(2-Chloro-benzoyl)-amino]-thiazole-4-carboxylic acid and benzylamine | 508.4 |
| 17 | 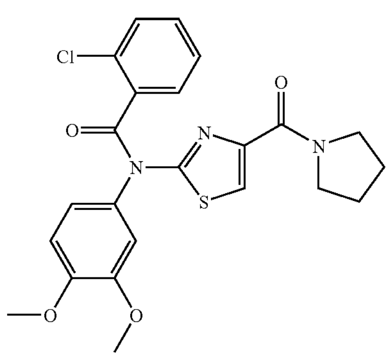 | 2-Chloro-N-(3,4-dimethoxy-phenyl)-N-[4-(pyrrolidine-1-carbonyl)-thiazol-2-yl]-benzamide | 2-[(3,4-Methoxy-phenyl)-(2-Chloro-benzoyl)-amino]-thiazole-4-carboxylic acid and pyrrolidine | 472.2 |
| 18 | 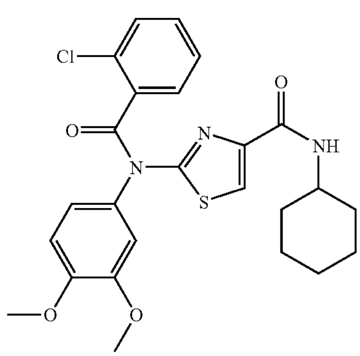 | 2-[(2-Chloro-benzoyl)-(3,4-dimethoxy-phenyl)-amino]-thiazole-4-carboxylic acid cyclohexylamide | 2-[(3,4-Methoxy-phenyl)-(2-Chloro-benzoyl)-amino]-thiazole-4-carboxylic acid and cyclohexylamine | 500.3 |

-continued

| Expl. No. | Structure | Systematic Name | Synthesised from: | MW found |
|---|---|---|---|---|
| 19 | 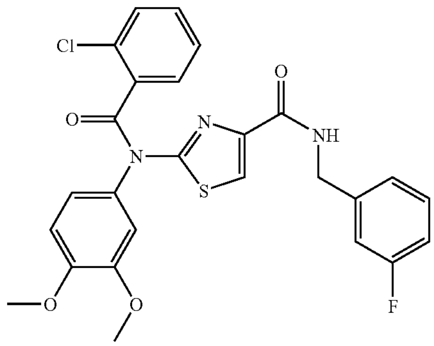 | 2-[(2-Chloro-benzoyl)-(3,4-dimethoxy-phenyl)-amino]-thiazole-4-carboxylic acid 3-fluoro-benzylamide | 2-[(3,4-Methoxy-phenyl)-(2-Chloro-benzoyl)-amino]-thiazole-4-carboxylic acid and 3-fluoro-benzylamine | 526.3 |
| 20 | 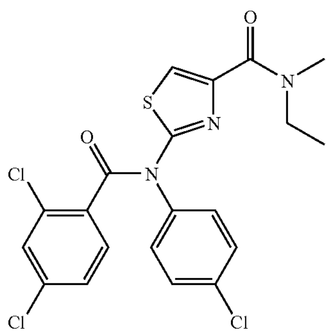 | 2-[(4-Chloro-phenyl)-(2,4-dichloro-benzoyl)-amino]-thiazole-4-carboxylic acid ethyl-methyl-amide | 2-[(4-Chloro-phenyl)-(2,4-dichloro-benzoyl)-amino]-thiazole-4-carboxylic acid and methylethylamine | 470.1 |
| 21 | 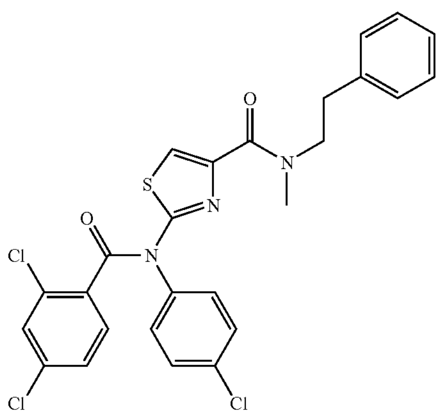 | 2-[(4-Chloro-phenyl)-(2,4-dichloro-benzoyl)-amino]-thiazole-4-carboxylic acid methyl-phenethyl-amide | 2-[(4-Chloro-phenyl)-(2,4-dichloro-benzoyl)-amino]-thiazole-4-carboxylic acid and methyl-phenethyl-amine | 546.1 |
| 22 | 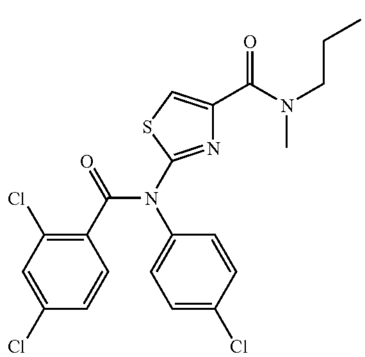 | 2-[(4-Chloro-phenyl)-(2,4-dichloro-benzoyl)-amino]-thiazole-4-carboxylic acid methyl-propyl-amide | 2-[(4-Chloro-phenyl)-(2,4-dichloro-benzoyl)-amino]-thiazole-4-carboxylic acid and methylpropylamine | 484.1 |

| Expl. No. | Structure | Systematic Name | Synthesised from: | MW found |
|---|---|---|---|---|
| 23 | 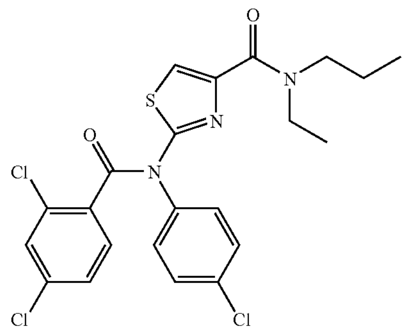 | 2-[(4-Chloro-phenyl)-(2,4-dichloro-benzoyl)-amino]-thiazole-4-carboxylic acid ethyl-propyl-amide | 2-[(4-Chloro-phenyl)-(2,4-dichloro-benzoyl)-amino]-thiazole-4-carboxylic acid and ethylpropylamine | 498.2 |
| 24 | 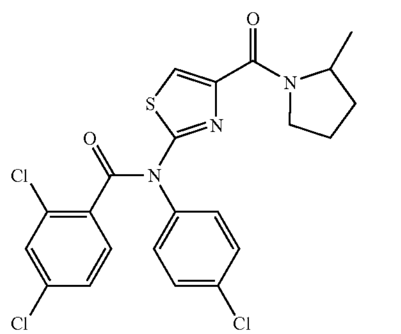 | 2,4-Dichloro-N-(4-chloro-phenyl)-N-[4-(2-methyl-pyrrolidine-1-carbonyl)-thiazol-2-yl]-benzamide | 2-[(4-Chloro-phenyl)-(2,4-dichloro-benzoyl)-amino]-thiazole-4-carboxylic acid and 2-methylpyrrolidine | 496.1 |
| 25 | 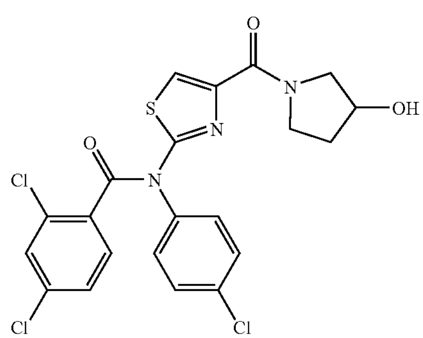 | 2,4-Dichloro-N-(4-chloro-phenyl)-N-[4-(3-hydroxy-pyrrolidine-1-carbonyl)-thiazol-2-yl]-benzamide | 2-[(4-Chloro-phenyl)-(2,4-dichloro-benzoyl)-amino]-thiazole-4-carboxylic acid and 3-hydroxy-pyrrolidine | 498.1 |
| 26 | 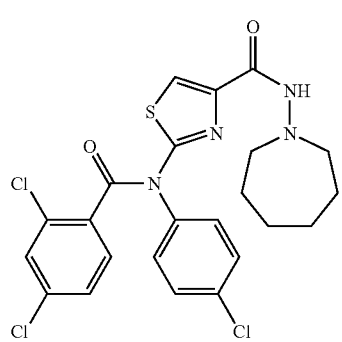 | 2-[(4-Chloro-phenyl)-(2,4-dichloro-benzoyl)-amino]-thiazole-4-carboxylic acid azepan-1-ylamide | 2-[(4-Chloro-phenyl)-(2,4-dichloro-benzoyl)-amino]-thiazole-4-carboxylic acid and azepan-1-ylamine | 525.2 |

-continued

| Expl. No. | Structure | Systematic Name | Synthesised from: | MW found |
|---|---|---|---|---|
| 27 | 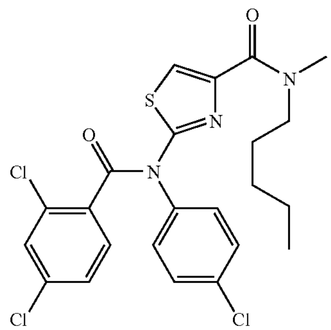 | 2-[(4-Chloro-phenyl)-(2,4-dichloro-benzoyl)-amino]-thiazole-4-carboxylic acid methyl-pentyl-amide | 2-[(4-Chloro-phenyl)-(2,4-dichloro-benzoyl)-amino]-thizazole-4-carboxylic acid and n-pentylmethylamine | 512.2 |
| 28 | 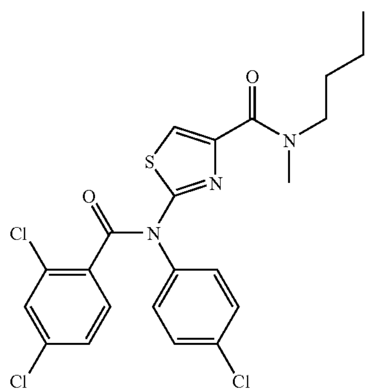 | 2-[(4-Chloro-phenyl)-(2,4-dichloro-benzoyl)-amino]-thiazole-4-carboxylic acid butyl-methyl-amide | 2-[(4-Chloro-phenyl)-(2,4-dichloro-benzoyl)-amino]-thiazole-4-carboxylic acid and n-butylmethylamine | 498.2 |
| 29 | 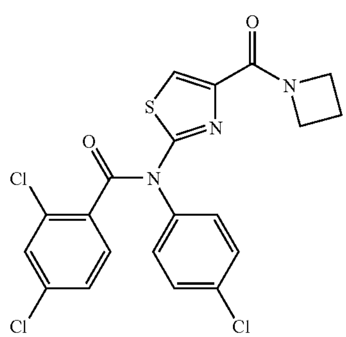 | N-[4-(Azetidine-1-carbonyl)-thiazol-2-yl]-2,4-dichloro-N-(4-chloro-phenyl)-benzamide | 2-[(4-Chloro-phenyl)-(2,4-dichloro-benzoyl)-aminpo]-thiazole-4-carboxylic acid and azetidine | 466.1 |
| 30 | 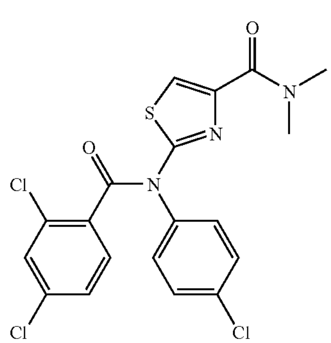 | 2-[(4-Chloro-phenyl)-(2,4-dichloro-benzoyl)-amino]-thiazole-4-carboxylic acid dimethylamide | 2-[(4-Chloro-phenyl)-(2,4-dichloro-benzoyl)-amino]-thiazole-4-carboxylic acid and dimethylamine | 456.1 |

| Expl. No. | Structure | Systematic Name | Synthesised from: | MW found |
|---|---|---|---|---|
| 31 | 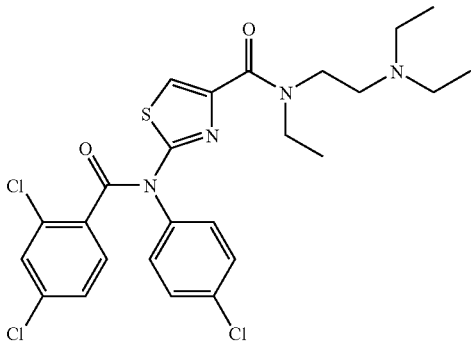 | 2-[(4-Chloro-phenyl)-(2,4-dichloro-benzoyl)-amino]-thiazole-4-carboxylic acid (2-diethylamino-ethyl)-ethyl-amide | 2-[(4-Chloro-phenyl)-(2,4-Dichloro-benzoyl)-amino]-thiazole-4-carboxylic acid and N,N,N'-Triethyl-ethane-1,2-diamine | 553.2 |
| 32 | 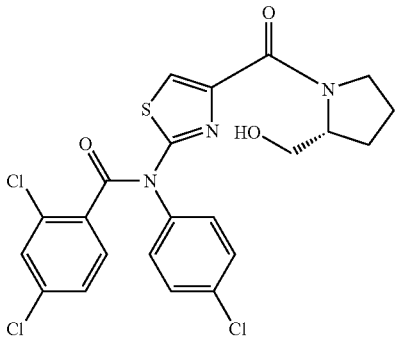 | 2,4-Dichloro-N-(4-chloro-phenyl)-N-[4-(2-hydroxymethyl-pyrrolidine-1-carbonyl)-thiazol-2-yl]-benzamide | 2-[(4-Chloro-phhenyl)-(2,4-dichloro-benzoyl)-amino]-thiazole-4-carboxylic acid and pyrrolidine | 512.2 |
| 33 | 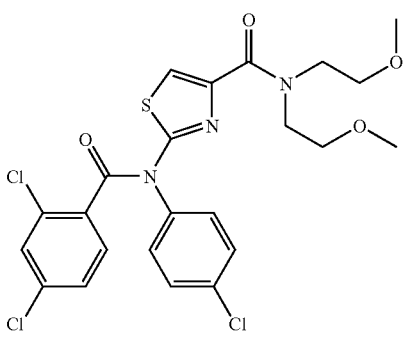 | 2-[(4-Chloro-phenyl)-(2,4-dichloro-benzoyl)-amino]-thiazole-4-carboxylic acid bis-(2-methoxy-ethyl)-amide | 2-[(4-Chloro-phenyl)-(2,4-dichloro-benzoyl)-amino]-thiazole-4-carboxylic acid and Bis-(2-methoxy-ethyl)-amine | 544.2 |
| 34 | 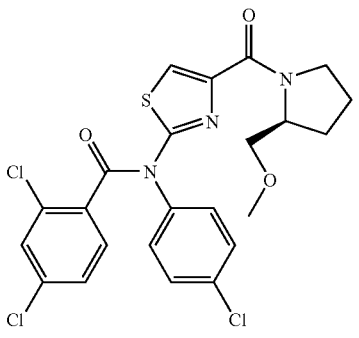 | 2,4-Dichloro-N-(4-chloro-phenyl)-N-[4-(2-(S)-methoxymethyl-pyrrolidine-1-carbonyl)-thiazol-2-yl]-benzamide | 2-[(4-Chloro-phenyl)-(2,4-dichloro-benzoyl)-amino]-thiazole-4-carboxylic acid and 2-(S)-methoxymethyl-pyrrolidine | 526.2 |

-continued

| Expl. No. | Structure | Systematic Name | Synthesised from: | MW found |
|---|---|---|---|---|
| 35 | 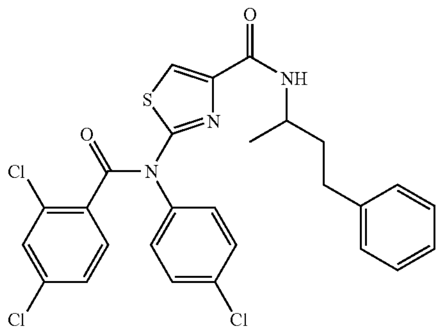 | 2-[(4-Chloro-phenyl)-(2,4-dichloro-benzoyl)-amino]-thiazole-4-carboxylic acid (1-methyl-3-phenyl-propyl)-amide | 2-[(4-Chloro-phenyl)-(2,4-dichloro-benzoyl)-amino]-thiazole-4-carboxylic acid and 1-methyl-3-phenyl-propylamine | 560.2 |
| 36 | 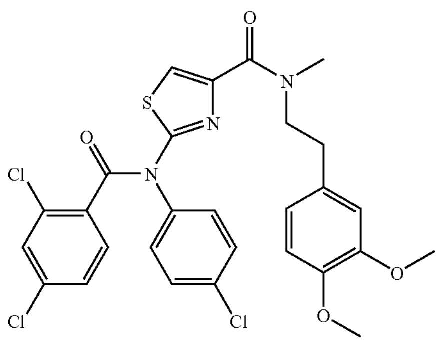 | 2-[(4-Chlorro-phenyl)-(2,4-dichloro-benzoyl)-amino]-thiazole-4-carboxylic acid [2-(3,4-dimethoxy-phenyl)-ethyl]-methyl-amide | 2-[(4-Chloro-phenyl)-(2,4-dichloro-benzoyl)-amino]-thiazole-4-carboxylic acid and [2-(3,4-dimethoxy-phenyl)-ethyl]-methyl-amine | 606.2 |
| 37 | 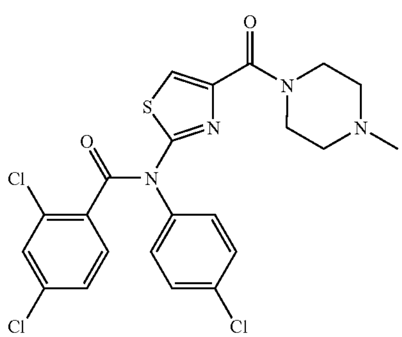 | 2,4-Dichloro-N-(4-chloro-phenyl)-N-[4-(4-methyl-piperazine-1-carbonyl)-thiazol-2-yl]-benzamide | 2-[(4-Chloro-phenyl)-(2,4-dichloro-benzoyl)-amino]-thiazole-4-carboxylic acid and N-methylpiperazine | 511.2 |
| 38 | 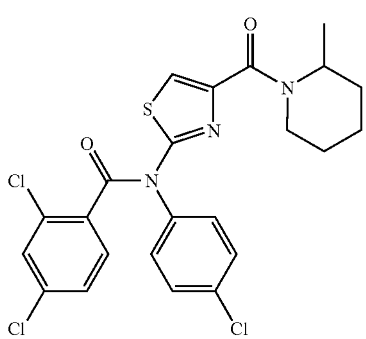 | 2,4-Dichloro-N-(4-chloro-phenyl)-N-[4-(2-methyl-piperidine-1-carbonyl)-thiazol-2-yl]-benzamide | 2-[(4-Chloro-phenyl)-(2,4-dichloro-benzoyl)-amino]-thiazole-4-carboxylic acid and 2-methylpiperidine | 510.2 |

-continued

| Expl. No. | Structure | Systematic Name | Synthesised from: | MW found |
|---|---|---|---|---|
| 39 | 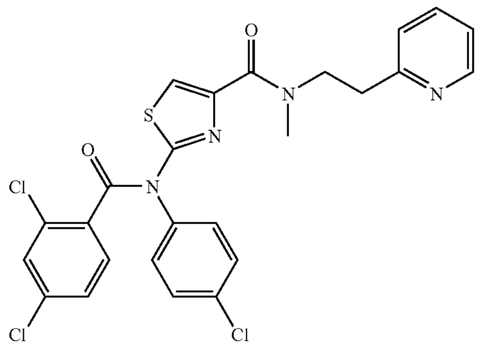 | 2-[(4-Chloro-phenyl)-(2,4-dichloro-benzoyl)-amino]-thiazole-4-carboxylic acid methyl-(2-pyridin-2-yl-ethyl)-amide | 2-[(4-Chloro-phenyl)-(2,4-dichloro-benzoyl)-amino]-thiazole-4-carboxylic acid and methyl-(2-pyridin-2-yl-ethyl)-amine | 547.1 |
| 40 | 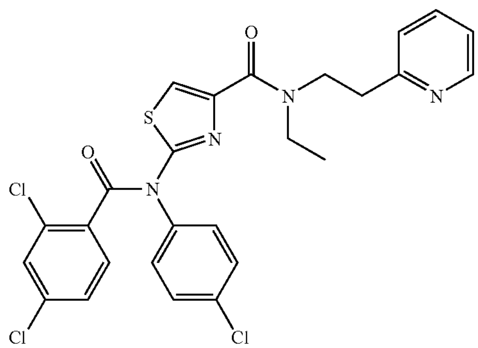 | 2-[(4-Chloro-phenyl)-(2,4-dichloro-benzoyl)-amino]-thiazole-4-carboxylic acid ethyl-(2-pyridin-2-yl-ethyl)-amide | 2-[(4-Chloro-phenyl)-(2,4-dichloro-benzoyl)-amino]-thiazole-4-carboxylic acid and ethyl-(2-pyridin-2-yl-ethyl)-amine | 559.1 |
| 41 | 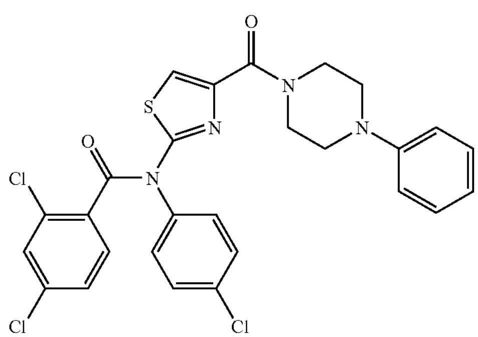 | 2,4-Dichloro-N-(4-chloro-phenyl)-N-[4-(4-phenyl-piperazine-1-carbonyl)-thiazol-2-yl]-benzamide | 2-[(4-Chloro-phenyl)-(2,4-dichloro-benzoyl)-amino]-thiazole-4-carboxylic acid and N-phenylpiperazine | 573.1 |
| 42 | 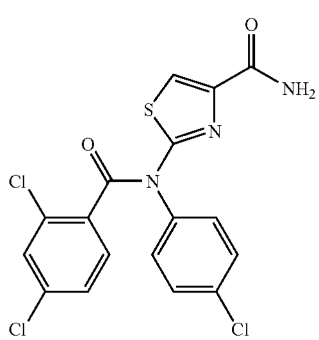 | 2-[(4-Chloro-phenyl)-(2,4-dichloro-benzoyl)-amino]-thiazole-4-carboxylic acid amide | 2-[(4-Chloro-phenyl)-(2,4-dichloro-benzoyl)-amino]-thiazole-4-carboxylic acid and ammonia | 425.9 |

-continued

| Expl. No. | Structure | Systematic Name | Synthesised from: | MW found |
|---|---|---|---|---|
| 43 | 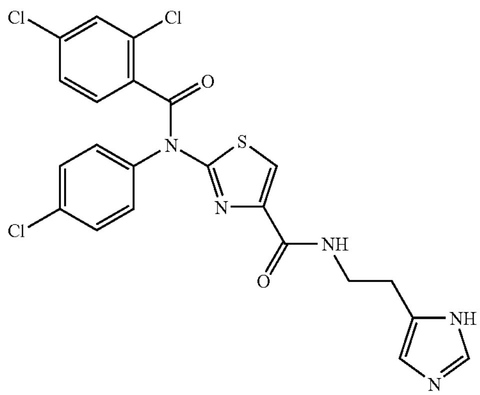 | 2-[(4-Chloro-phenyl)-2,4-dichloro-benzoyl)-amino]-thiazole-4-carboxylic acid [2-(1H-imidazol-4-yl)-ethyl]-amide | 2-[(4-Chloro-phenyl)-(2,4-dichloro-benzoyl)-amino]-thiazole-4-carboxylic acid and [2-(1H-imidazol-4-yl)-ethyl]-amine | 520.1 |
| 44 | 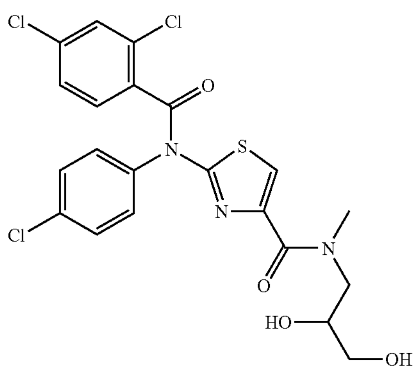 | 2-[(4-Chloro-phenyl)-(2,4-dichloro-benzoyl)-amino]-thiazole-4-carboxylic acid (2,3-dihydroxy-propyl)-methyl-amide | 2-[(4-Chloro-phenyl)-(2,4-dichloro-benzoyl)-amino]-thiazole-4-carboxylic acid and 3-methylamino-propane-1,2-diol | 516.1 |
| 45 | 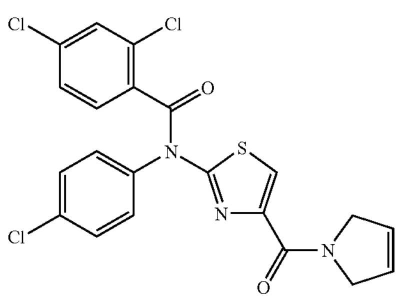 | 2,4-Dichloro-N-(4-chloro-phenyl)-N-[4-(2,5-dihydro-pyrrole-1-carbonyl)-thiazol-2-yl]-benzamide | 2-[(4-Chloro-phenyl)-(2,4-dichloro-benzoyl)-amino]-thiazole-4-carboxylic acid and 2,5-dihydro-1H-pyrrole | 482.1 |
| 46 | 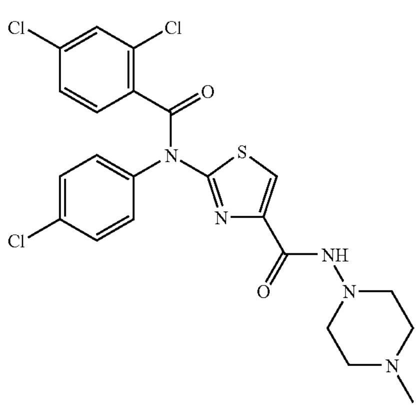 | 2-[(4-Chloro-phenyl)-(2,4-dichloro-benzoyl)-amino]-thiazole-4-carboxylic acid (4-methyl-piperazin-1-yl)-amide | 2-[(4-Chloro-phenyl)-(2,4-dichloro-benzoyl)-amino]-thiazole-4-carboxylic acid and N-methylpiperazine | 511.2 |

-continued

| Expl. No. | Structure | Systematic Name | Synthesised from: | MW found |
|---|---|---|---|---|
| 47 | 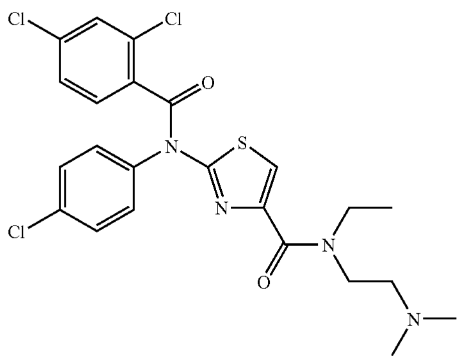 | 2-[(4-Chloro-phenyl)-(2,4-dichloro-benzoyl)-amino]-thiazole-4-carboxylic acid (2-dimethylamino-ethyl)-ethyl-amide | 2-[(4-Chloro-phenyl)-(2,4-dichloro-benzoyl)-amino]-thiazole-4-carboxylic acid and N'-Ethyl-N,N-dimethyl-ethane-1,2-diamine | 525.2 |
| 48 | 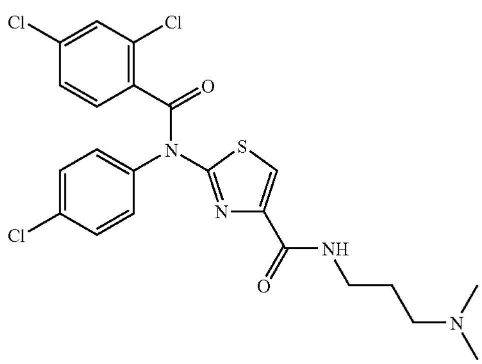 | 2-[(4-Chloro-phenyl)-(2,4-dichloro-benzoyl)-amino]-thiazole-4-carboxylic acid (3-dimethylamino-propyl)-amide | 2-[(4-Chloro-phenyl)-(2,4-dichloro-benzoyl)-amino]-thiazole-4-carboxylic acid and N,N-dimethyl-propane-1,3-diamine | 513.2 |
| 49 | 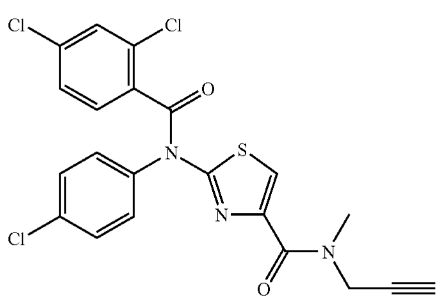 | 2-[(4-Chloro-phenyl)-(2,4-dichloro-benzoyl)-amino]-thiazole-4-carboxylic acid methyl-prop-2-ynyl-amide | 2-[(4-Chloro-phenyl)-(2,4-dichloro-benzoyl)-amino]-thiazole-4-carboxylic acid and methyl-prop-2-ynyl-amine | 478.0 |
| 50 | 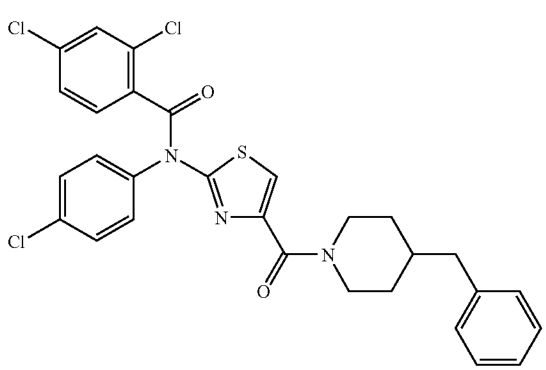 | N-[4-(4-Benzyl-piperidine-1-carbonyl)-thiazol-2-yl]-2,4-dichloro-N-(4-chloro-phenyl)-benzamide | 2-[(4-Chloro-phenyl)-(2,4-dichloro-benzoyl)-amino]-thiazole-4-carboxylic acid and 4-benzyl-piperidine | 586.2 |

-continued

| Expl. No. | Structure | Systematic Name | Synthesised from: | MW found |
|---|---|---|---|---|
| 51 | 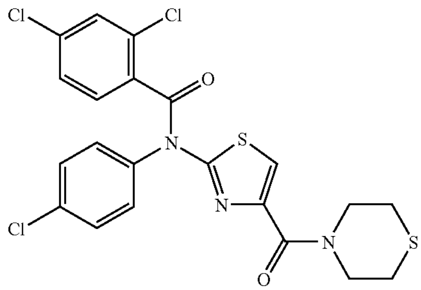 | 2,4-Dichloro-N-(4-chloro-phenyl)-N-[4-(thiomorpholine-4-carbonyl)-thiazol-2-yl]-benzamide | 2-[(4-Chloro-phenyl)-(2,4-dichloro-benzoyl)-amino]-thiazole-4-carboxylic acid and thiomorpholine | 512.2 |
| 52 | 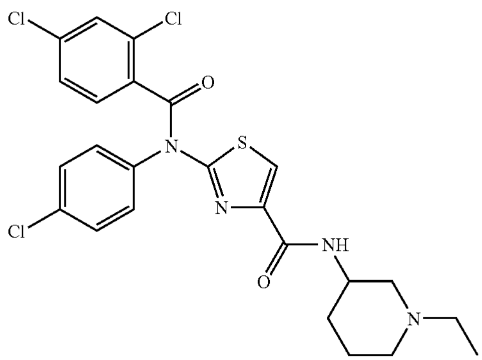 | 2-[(4-Chloro-phenyl)-(2,4-dichloro-benzoyl)-amino]-thiazole-4-carboxylic acid (1-ethyl-piperidin-3-yl)-amide | 2-[(4-Chloro-phenyl)-(2,4-dichloro-benzoyl)-amino]-thiazole-4-carboxylic acid and 1-ethyl-piperidin-3-ylamine | 539.2 |
| 53 | 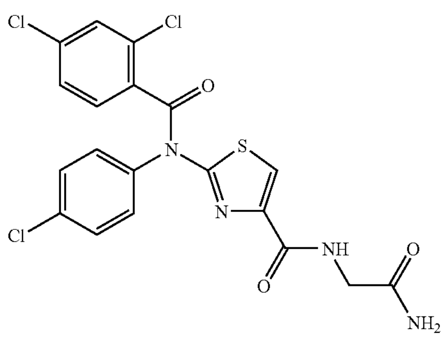 | 2-[(4-Chloro-phenyl)-(2,4-dichloro-benzoyl)-amino]-thiazole-4-carboxylic acid carbamoylmethyl-amide | 2-[(4-Chloro-phenyl)-(2,4-dichloro-benzoyl)-amino]-thiazole-4-carboxylic acid and 2-amino-acetamide | 483.1 |
| 54 | 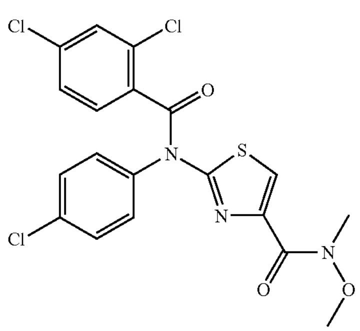 | 2-[(4-Chloro-phenyl)-(2,4-dichloro-benzoyl)-amino]-thiazole-4-carboxylic acid methoxy-methyl-amide | 2-[(4-Chloro-phenyl)-(2,4-dichloro-benzoyl)-amino]-thiazole-4-carboxylic acid and O,N-dimethyl-hydroxylamine | 472.1 |

-continued

| Expl. No. | Structure | Systematic Name | Synthesised from: | MW found |
|---|---|---|---|---|
| 55 | 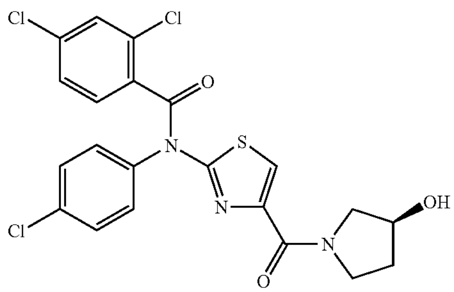 | 2,4-Dichloro-N-(4-chloro-phenyl)-N-[4-(3-(S)-hydroxy-pyrrolidine-1-carbonyl)-thiazol-2-yl]-benzamide | 2-[(4-Chloro-phenyl)-(2,4-dichloro-benzoyl)-amino]-thiazole-4-carboxylic acid and 3-(S)-hydroxypyrrolidine | 496.8 |
| 56 | 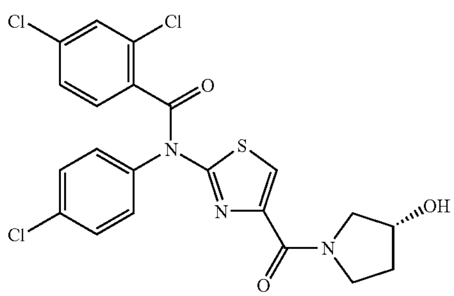 | 2,4-Dichloro-N-(4-chloro-phenyl)-N-[4-(3-(R)-hydroxy-pyrrolidine-1-carbonyl)-thiazol-2-yl]-benzamide | 2-[(4-Chloro-phenyl)-(2,4-dichloro-benzoyl)-amino]-thiazole-4-carboxylic acid and 3-(R)-hydroxypyrrolidine | 496.8 |
| 57 | 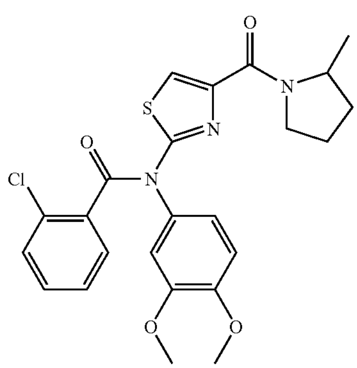 | 2-Chloro-N-(3,4-dimethoxy-phenyl)-N-[4-(2-methyl-pyrrolidine-1-carbonyl)-thiazol-2-yl]-benzamide | 2-[(3,4-Methoxy-phenyl)-(2-Chloro-benzoyl)-amino]-thiazole-4-carboxylic acid and 2-methylpyrrolidine | 486.2 |
| 58 | 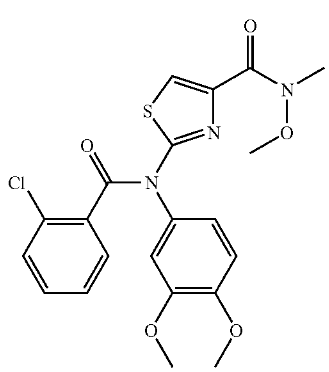 | 2-[(2-Chloro-benzoyl)-(3,4-dimethoxy-phenyl)-amino]-thiazole-4-carboxylic acid methoxy-methyl-amide | 2-[(3,4-Methoxy-phenyl)-(2-Chloro-benzoyl)-amino]-thiazole-4-carboxylic acid and O,N-dimethyl-hydroxylamine | 462.1 |

-continued

| Expl. No. | Structure | Systematic Name | Synthesised from: | MW found |
|---|---|---|---|---|
| 59 | 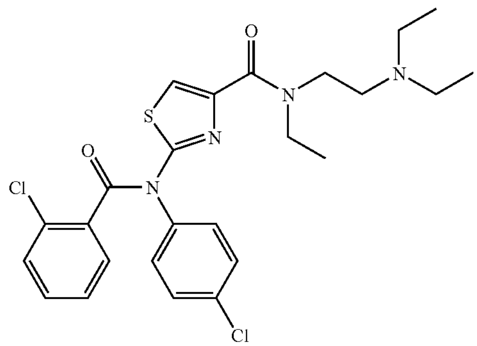 | 2-[(2-Chloro-benzoyl)-(4-chloro-phenyl)-amino]-thiazole-4-carboxylic acid (2-diethylamino-ethyl)-ethyl-amide | 2-[(2-Chloro-benzoyl)-(4-chloro-phenyl)-amino]-thiazole-4-carboxylic acid and N,N,N'-Triethyl-ethane-1,2-diamine | 419.2 |
| 60 | 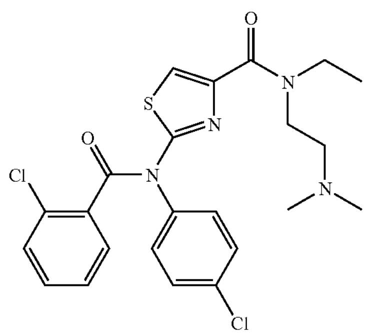 | 2-[(2-Chloro-benzoyl)-(4-chloro-phenyl)-amino]-thiazole-4-carboxylic acid (2-dimethylamino-ethyl)-ethyl-amide | 2-[(2-Chloro-benzoyl)-(4-chloro-phenyl)-amino]-thiazole-4-carboxylic acid and N'-Ethyl-N,N-dimethyl-ethane-1,2-diamine | 491.1 |
| 61 | 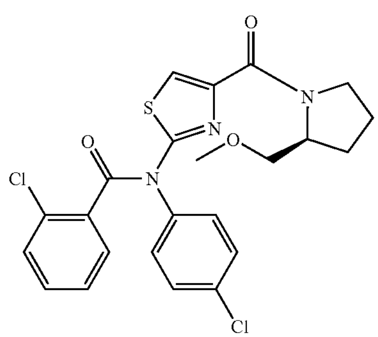 | 2-Chloro-N-(4-chloro-phenyl)-N-[4-(2-(S)-methoxymethyl-pyrrolidine-1-carbonyl)-thiazol-2-yl]-benzamide | 2-[(2-Chloro-benzoyl)-(4-chloro-phenyl)-amino]-thiazole-4-carboxylic acid and 2-(S)-methoxymethyl-pyrrolidine | 490.1 |
| 62 | 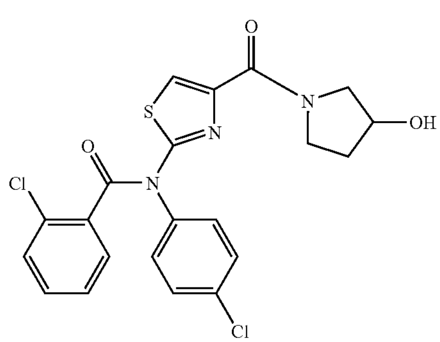 | 2-Chloro-N-(4-chloro-phenyl)-N-[4-(3-hydroxy-pyrrolidine-1-carbonyl)-thiazol-2-yl]-benzamide | 2-[(2-Chloro-benzoyl)-(4-chloro-phenyl)-amino]-thiazole-4-carboxylic acid and 3-hydroxypyrrolidine | 462.0 |

| Expl. No. | Structure | Systematic Name | Synthesised from: | MW found |
|---|---|---|---|---|
| 63 | 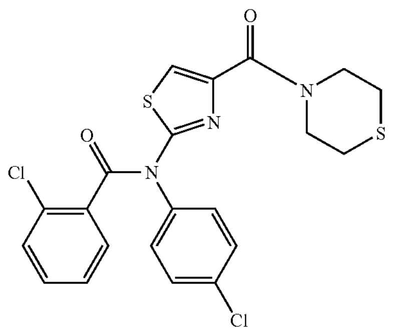 | 2-Chloro-N-(4-chloro-phenyl)-N-[4-(thiomorpholine-4-carbonyl)-thiazol-2-yl]-benzamide | 2-[(2-Chloro-benzoyl)-(4-chloro-phenyl)-amino]-thiazole-4-carboxylic acid and thiomorpholine | 478.0 |
| 64 | 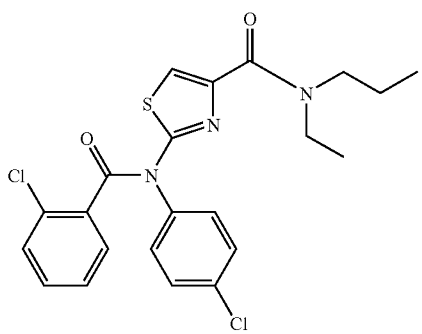 | 2-[(2-Chloro-benzoyl)-(4-chloro-phenyl)-amino]-thiazole-4-carboxylic acid ethyl-propyl-amide | 2-[(2-Chloro-benzoyl)-(4-chloro-phenyl)-amino]-thiazole-4-carboxylic acid and n-propylethylamine | 462.1 |
| 65 | 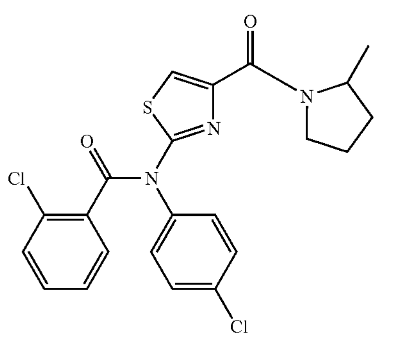 | 2-Chloro-N-(4-chloro-phenyl)-N-[4-(2-methyl-pyrrolidine-1-carbonyl)-thiazol-2-yl]-benzamide | 2-[(2-Chloro-benzoyl)-(4-chloro-phenyl)-amino]-thiazole-4-carboxylic acid and 2-methylpyrrolidine | 460.1 |
| 66 | 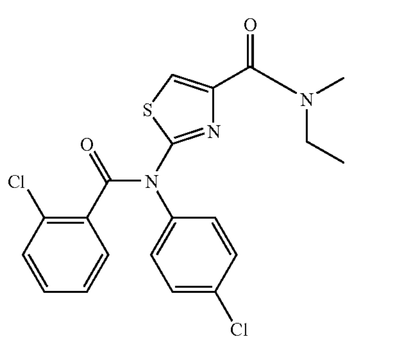 | 2-[(2-Chloro-benzoyl)-(4-chloro-phenyl)-amino]-thiazole-4-carboxylic acid ethyl-methyl-amide | 2-[(2-Chloro-benzoyl)-(4-chloro-phenyl)-amino]-thiazole-4-carboxylic acid ethylmethylamine | 434.1 |

-continued

| Expl. No. | Structure | Systematic Name | Synthesised from: | MW found |
|---|---|---|---|---|
| 67 | 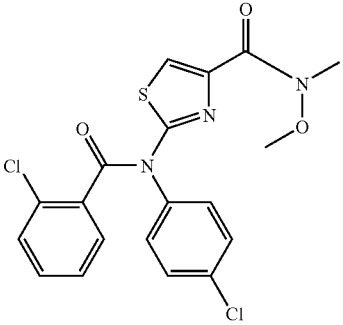 | 2-[(2-Chloro-benzoyl)-(4-chloro-phenyl)-amino]-thiazole-4-carboxylic acid methoxy-methyl-amide | 2-[(2-Chloro-benzoyl)-(4-chloro-phenyl)-amino]-thiazole-4-carboxylic acid and O,N-dimethyl-hydroxylamine | 436.0 |
| 68 | 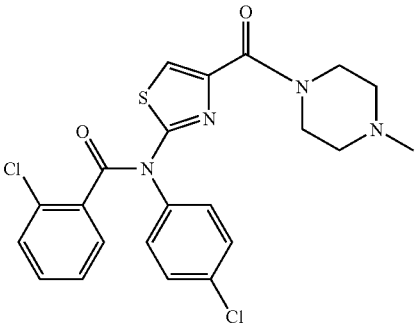 | 2-Chloro-N-(4-chloro-phenyl)-N-[4-(4-methyl-piperazine-1-carbonyl)-thiazol-2-yl]-benzamide | 2-[(2-Chloro-benzoyl)-(4-chloro-phenyl)-amino]-thiazole-4-carboxylic acid and N-methylpiperazine | 475.0 |
| 69 | 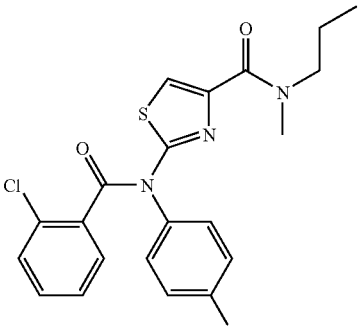 | 2-[(2-Chloro-benzoyl)-(4-chloro-phenyl)-amino]-thiazole-4-carboxylic acid methyl-propyl-amide | 2-[(2-Chloro-benzoyl)-(4-chloro-phenyl)-amino]-thiazole-4-carboxylic acid and n-propylmethylamine | 448.0 |
| 70 | 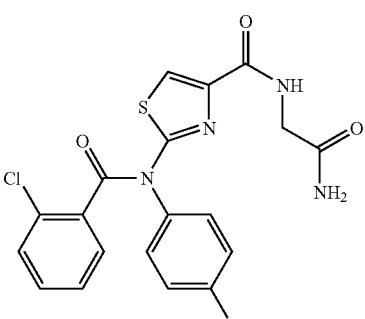 | 2-[(2-Chloro-benzoyl)-(4-chloro-phenyl)-amino]-thiazole-4-carboxylic acid carbamoylmethyl-amide | 2-[(2-Chloro-benzoyl)-(4-chloro-phenyl)-amino]-thiazole-4-carboxylic acid and 2-amino-acetamide | 449.0 |

| Expl. No. | Structure | Systematic Name | Synthesised from: | MW found |
|---|---|---|---|---|
| 71 | 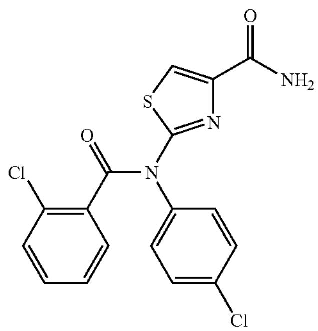 | 2-[(2-Chloro-benzoyl)-(4-chloro-phenyl)-amino]-thiazole-04-carboxylic acid amide | 2-[(2-Chloro-benzoyl)-(4-chloro-phenyl)-amino]-thiazole-4-carboxylic acid and ammonia | 392.0 |
| 72 | 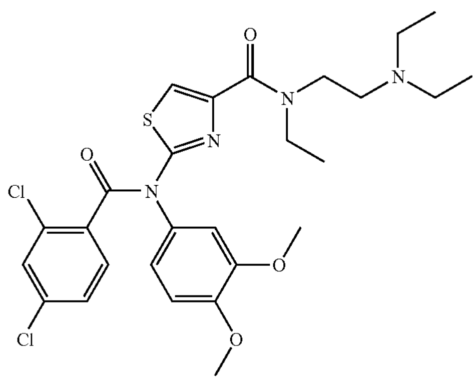 | 2-[(2,4-Dichloro-benzoyl)-(3,4-dimethoxy-phenyl)-amino]-thiazole-4-carboxylic accid (2-diethylamino-ethyl)-ethyl-amide | 2-[(3,4-Methoxy-phenyl)-(2,4-dichloro-benzoyl)-amino]-thiazole-4-carboxylic acid and N,N,N'-Triethyl-ethane-1,2-diamine | 579.3 |
| 73 | 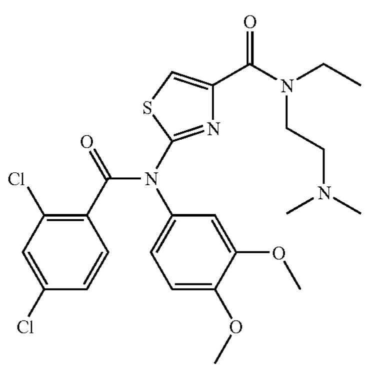 | 2-[(2,4-Dichloro-benzoyl)-(3,4-dimethoxy-phenyl)-amino]-thiazole-4-carboxylic acid (2-dimethylamino-ethyl)-ethyl-amide | 2-[(3,4-Methoxy-phenyl)-(2,4-dichloro-benzoyl)-amino]-thiazole-4-carboxylic acid and N'-Ethyl-N,N-dimethyl-ethane-1,2-diamine | 551.3 |
| 74 | 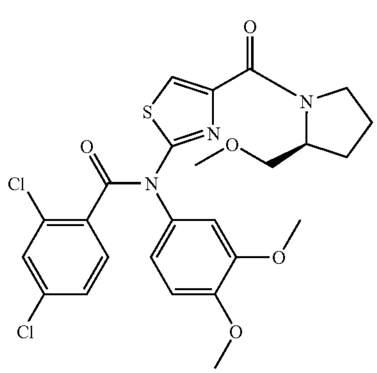 | 2,4-Dichloro-N-(3,4-dimethoxy-phenyl)-N-[4-(2-(S)-methoxymethyl-pyrrolidine-1-carbonyl)-thiazol-2-yl]-benzamide | 2-[(3,4-Methoxy-phenyl)-(2,4-dichloro-benzoyl)-amino]-thiazole-4-carboxylic acid and 2-(S)-methoxymethyl-pyrrolidine | 552.2 |

-continued

| Expl. No. | Structure | Systematic Name | Synthesised from: | MW found |
|---|---|---|---|---|
| 75 | 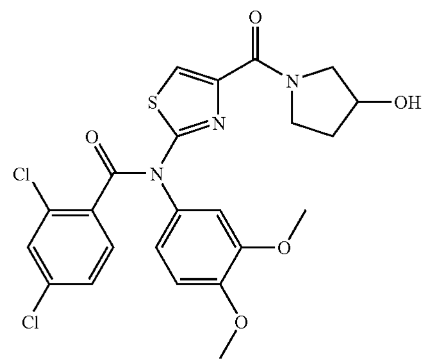 | 2,4-Dichloro-N-(3,4-dimethoxy-phenyl)-N-[4-(3-hydroxy-pyrrolidine-1-carbonyl)-thiazol-2-yl]-benzamide | 2-[(3,4-Methoxy-phenyl)-2,4-dichloro-benzoyl)-amino]-thiazole-4-carboxylic acid and 3-hydroxypyrrolidine | 522.1 |
| 76 | 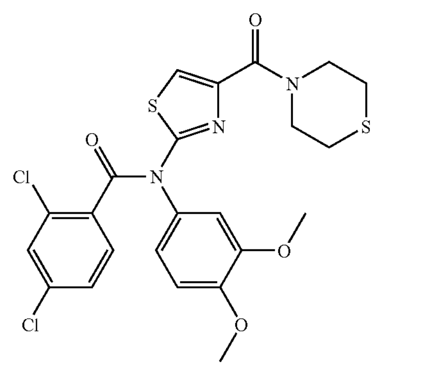 | 2,4-Dichloro-N-(3,4-dimethoxy-phenyl)-N-[4-(thiomorpholine-4-carbonyl)-thiazol-2-yl]-benzamide | 2-[(3,4-Methoxy-phenyl)-(2,4-dichloro-benzoyl)-amino]-thiazole-4-carboxylic acid and thiomorpholine | 538.2 |
| 77 | 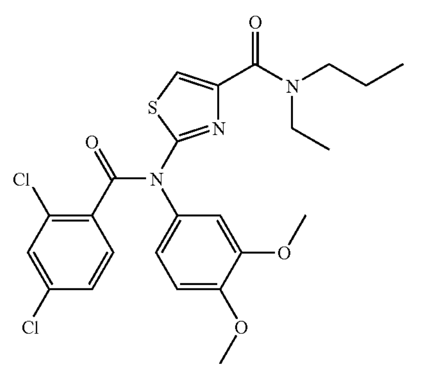 | 2-[(2,4-Dichloro-benzoyl)-(3,4-dimethoxy-phenyl)-amino]-thiazole-4-carboxylic acid ethyl-propyl-amide | 2-[(3,4-Methoxy-phenyl)-(2,4-dichloro-benzoyl)-amino]-thiazole-4-carboxylic acid and n-propylethylamine | 522.2 |
| 78 | 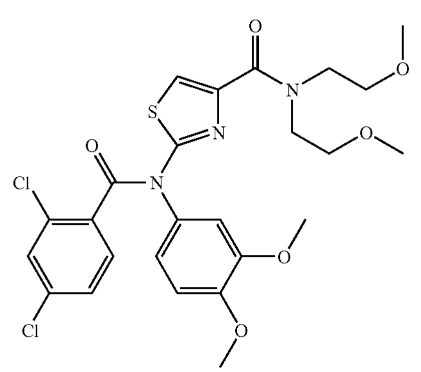 | 2-[(2,4-Dichloro-benzoyl)-(3,4-dimethoxy-phenyl)-amino]-thiazole-4-carboxylic acid bis-(2-methoxy-ethyl)-amide | 2-[(3,4-Methoxy-phenyl)-(2,4-dichloro-benzoyl)-amino]-thiazole-4-carboxylic acid and bis-(2-methoxy-ethyl)-amine | 568.2 |

-continued

| Expl. No. | Structure | Systematic Name | Synthesised from: | MW found |
|---|---|---|---|---|
| 79 | 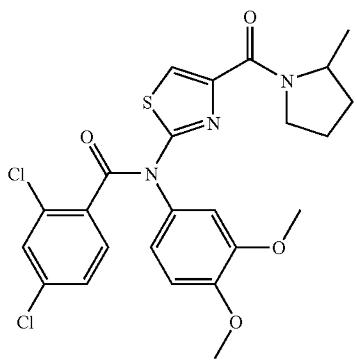 | 2,4-Dichloro-N-(3,4-dimethoxy-phenyl)-N-[4-(2-methyl-pyrrolidine-1-carbonyl)-thiazol-2-yl]-benzamide | 2-[(3,4-Methoxy-phenyl)-(2,4-dichloro-benzoyl)-amino]-thiazole-4-carboxylic acid and 2-methylpyrrolidine | 520.1 |
| 80 | 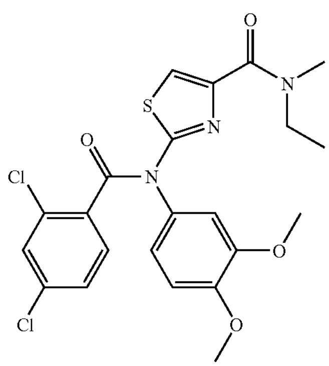 | 2-[(2,4-Dichloro-benzoyl)-(3,4-dimethoxy-phenyl)-amino]-thiazole-4-carboxylic acid ethyl-methyl-amide | 2-[(3,4-Methoxy-phenyl)-(2,4-dichloro-benzoyl)-amino]-thiazole-4-carboxylic acid and ethylmethylamine | 494.1 |
| 81 | 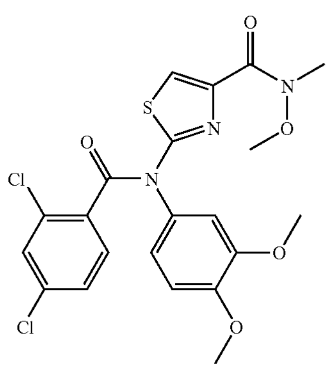 | 2-[(2,4-Dichloro-benzoyl)-(3,4-dimethoxy-phenyl)-amino]-thiazole-4-carboxylic acid methoxy-methyl-amide | 2-[(3,4-Methoxy-phenyl)-(2,4-dichloro-benzoyl)-amino]-thiazole-4-carboxylic acid and O,N-dimethyl-hydroxylamine | 496.1 |
| 82 | 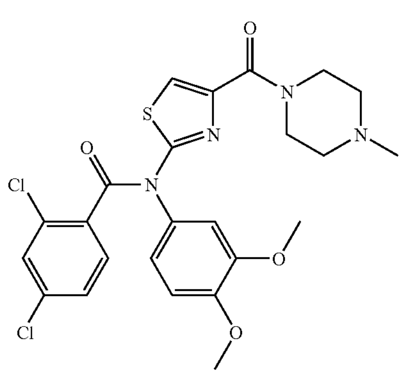 | 2,4-Dichloro-N-(3,4-dimethoxy-phenyl)-N-[4-(4-methyl-piperazine-1-carbonyl)-thiazol-2-yl]-benzamide | 2-[(3,4-Methoxy-phenyl)-(2,4-dichloro-benzoyl)-amino]-thiazole-4-carboxylic acid and N-methylpiperazine | 535.1 |

-continued

| Expl. No. | Structure | Systematic Name | Synthesised from: | MW found |
|---|---|---|---|---|
| 83 | 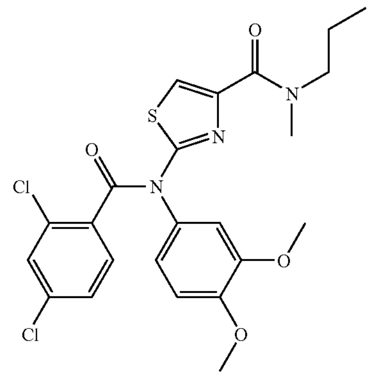 | 2-[(2,4-Dichloro-benzoyl)-(3,4-dimethoxy-phenyl)-amino]-thiazole-4-carboxylic acid methyl-propyl-amide | 2-[(3,4-Methoxy-phenyl)-(2,4-dichloro-benzoyl)-amino]-thiazole-4-carboxylic acid and n-propylmethylamine | 508.1 |
| 84 | 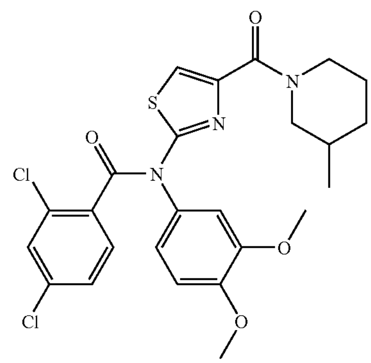 | 2,4-Dichloro-N-(3,4-dimethoxy-phenyl)-N-[4-(3-methyl-piperidine-1-carbonyl)-thiazol-2-yl]-benzamide | 2-[(3,4-Methoxy-phenyl)-(2,4-dichloro-benzoyl)-amino]-thiazole-4-carboxylic acid and 3-methylpiperidine | 534.1 |
| 85 | 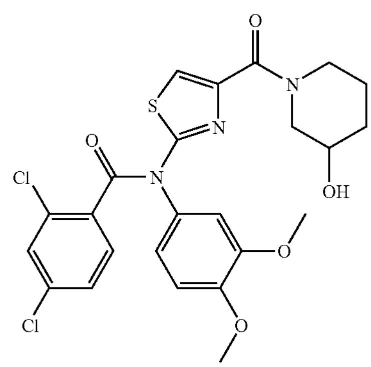 | 2,4-Dichloro-N-(3,4-dimethoxy-phenyl)-N-[4-(3-hydroxy-piperidine-1-carbonyl)-thiazol-2-yl]-benzamide | 2-[(3,4-Methoxy-phenyl)-(2,4-dichloro-benzoyl)-amino]-thiazole-4-carboxylic acid and 3-hydroxypiperidine | 536.1 |
| 86 | 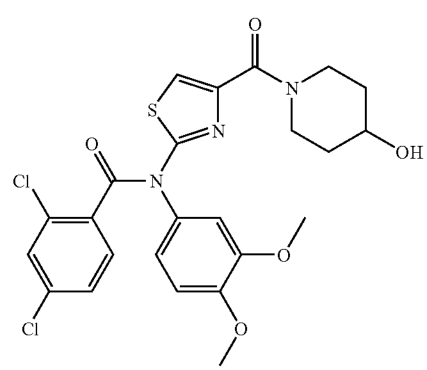 | 2,4-Dichloro-N-(3,4-dimethoxy-phenyl)-N-[4-(4-hydroxy-piperidine-1-carbonyl)-thiazol-2-yl]-benzamide | 2-[(3,4-Methoxy-phenyl)-(2,4-dichloro-benzoyl)-amino]-thiazole-4-carboxylic acid and 4-hydroxypiperidine | 536.1 |

-continued

| Expl. No. | Structure | Systematic Name | Synthesised from: | MW found |
|---|---|---|---|---|
| 87 | 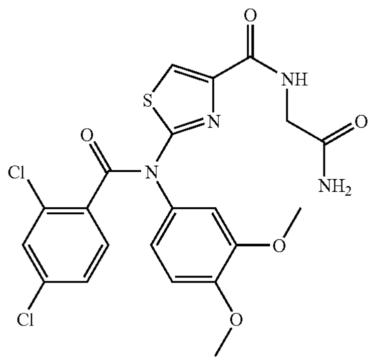 | 2-[(2,4-Dichloro-benzoyl)-(3,4-dimethoxy-phenyl)-amino]-thiazole-4-carboxylic acid carbamoylmethyl-amide | 2-[(3,4-Methoxy-phenyl)-(2,4-dichloro-benzoyl)-amino]-thiazole-4-carboxylic acid and 2-Amino-acetamide | 509.1 |
| 88 | 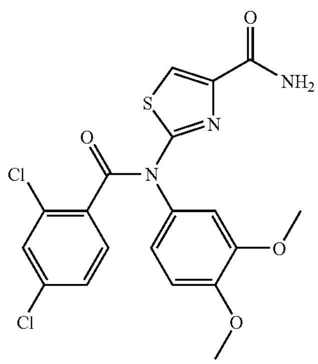 | 2-[(2,4-Dichloro-benzoyl)-(3,4-dimethoxy-phenyl)-amino]-thiazole-4-carboxylic acid amide | 2-[(3,4-Methoxy-phenyl)-(2,4-dichloro-benzoyl)-amino]-thiazole-4-carboxylic acid and ammonia | 452.0 |
| 89 | 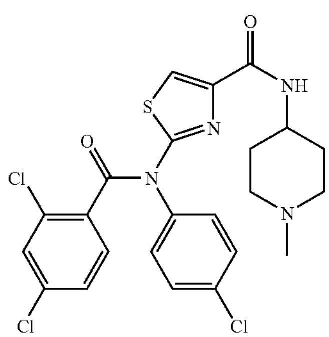 | 2-[(4-Chloro-phenyl)-(2,4-dichloro-benzoyl)-amino]-thiazole-4-carboxylic acid (1-methyl-piperidin-4-yl)-amide | 2-[(4-Chloro-phenyl)-(2,4-dichloro-benzoyl)-amino]-thiazole-4-carboxylic acid and 1-methyl-piperidin-4-ylamine | 525.1 |
| 90 | 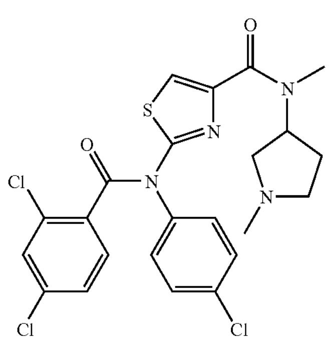 | 2-[(4-Chloro-phenyl)-(2,4-dichloro-benzoyl)-amino]-thiazole-4-carboxylic acid methyl-(1-methyl-pyrrolidin-3-yl)-amide | 2-[(4-Chloro-phenyl)-(2,4-dichloro-benzoyl)-amino]-thiazole-4-carboxylic acid and methyl-(1-methyl-pyrrolidin-3-yl)-amine | 525.1 |

-continued

| Expl. No. | Structure | Systematic Name | Synthesised from: | MW found |
|---|---|---|---|---|
| 91 | 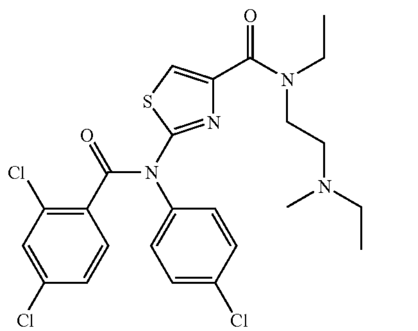 | 2-[(4-Chloro-phenyl)-(2,4-dichloro-benzoyl)-amino]-thiazole-4-carboxylic acid ethyl-[2-(ethyl-methyl-amino)-ethyl]-amide | 2-[(4-Chloro-phenyl)-(2,4-dichloro-benzoyl)-amino]-thiazole-4-carboxylic acid and N,N'-Diethyl-N-methyl-ethane-1,2-diamine | 539.1 |
| 92 | 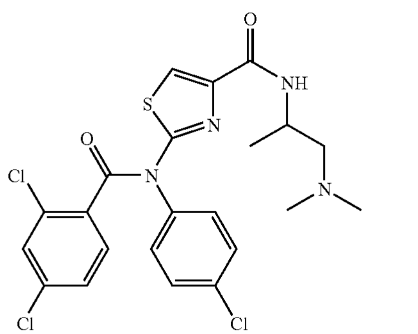 | 2-[(4-Chloro-phenyl)-(2,4-dichloro-benzoyl)-amino]-thiazole-4-carboxylic acid (2-dimethylamino-1-methyl-ethyl)-amide | 2-[(4-Chloro-phenyl)-(2,4-dichloro-benzoyl)-amino]-thiazole-4-carboxylic acid and N',N'-Dimethyl-propane-1,2-diamine | 511.1 |
| 93 | 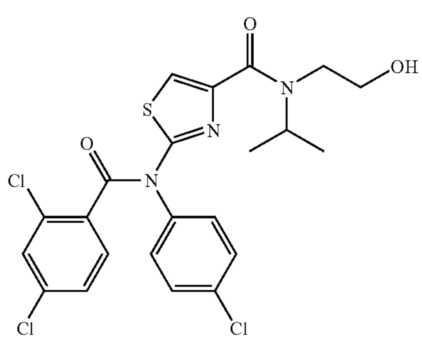 | 2-[(4-Chloro-phenyl)-(2,4-dichloro-benzoyl)-amino]-thiazole-4-carboxylic acid (2-hydroxy-ethyl)-isopropyl-amide | 2-[(4-Chloro-phenyl)-(2,4-dichloro-benzoyl)-amino]-thiazole-4-carboxylic acid and 2-isopropylamino-ethanol | 512.1 |
| 94 | 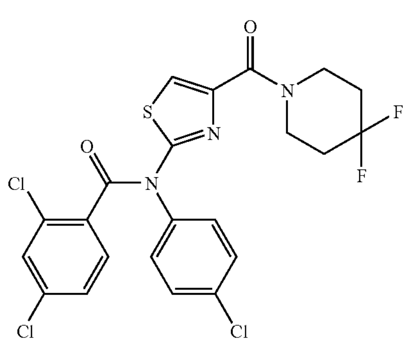 | 2,4-Dichloro-N-(4-chloro-phenyl)-N-[4-(4,4-difluoro-piperidine-1-carbonyl)-thiazol-2-yl]-benzamide | 2-[(4-Chloro-phenyl)-(2,4-dichloro-benzoyl)-amino]-thiazole-4-carboxylic acid and 4,4-difluoro-piperidine | 530.0 |

| Expl. No. | Structure | Systematic Name | Synthesised from: | MW found |
|---|---|---|---|---|
| 95 | 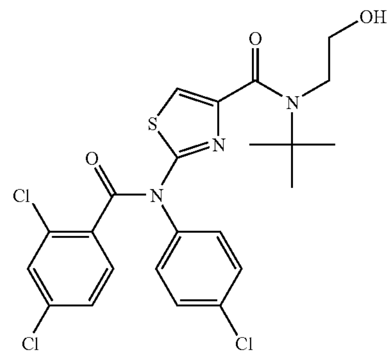 | 2-[(4-Chloro-phenyl)-(2,4-dichloro-benzoyl)-amino]-thiazole-4-carboxylic acid tert-butyl-(2-hydroxy-ethyl)-amide | 2-[(4-Chloro-phenyl)-(2,4-dichloro-benzoyl)amino]-thiazole-4-carboxylic acid and 2-isobutylamino-ethanol | 527.9 |

Example 96

2,4-Dichloro-N-(3,4-dimethoxy-phenyl)-N-[5-methyl-4-(pyrrolidine-1-carbonyl)-thiazol-2-yl]-benzamide

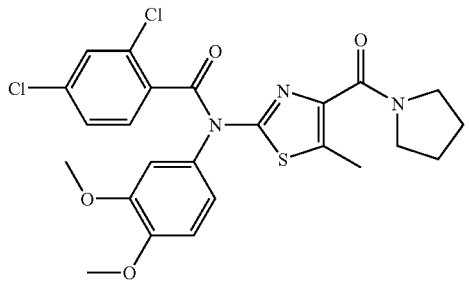

A mixture of 32 mg (0.07 mmol) 2-[(2,4-Dichloro-benzoyl)-(3,4-dimethoxy-phenyl)-amino]-5-methyl-thiazole-4-carboxylic acid, 14.8 mg (0.091 mmol) Carbonyldimimidazole and 12.4 mg (0.175 mmol) pyrrolidine in 1.2 ml DMF was stirred at room temperature for 16 h. The mixture was directly subjected to reversed phase HPLC purification eluting with an acetonitrile/water gradient to yield after evaporation of the product fractions 13.7 mg (38%) of the title compound. MS (m/e): 520.1 (MH$^+$, 100%)

According to the procedure described fort he synthesis of Example 96 further derivatives have been synthesised from 2-[(4-Chloro-phenyl)-(2,4-dichloro-benzoyl)-amino]-5-methyl-thiazole-4-carboxylic acid or 2-[(2,4-Dichloro-benzoyl)-(3,4-dimethoxy-phenyl)-amino]-5-methyl-thiazole-4-carboxylic acid and various commercially available amines and comprise Examples 97-Example 124 below. In cases of Example 102 and 118 additionally 2 eq. NEt$_3$ were added to the reaction mixture as amine hydrochlorides were used as starting materials.

Examples 97-124

The following compounds have been prepared in analogy to the process described in Example 96:

| Expl. No. | Structure | Systematic Name | Synthesised from: | MW found |
|---|---|---|---|---|
| 97 | 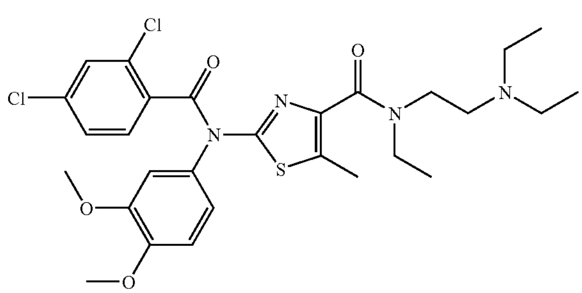 | 2-[(2,4-Dichloro-benzoyl)-(3,4-dimethoxy-phenyl)-amino]-5-methyl-thiazole-4-carboxylic acid (2-diethylamino-ethyl)-ethyl-amide | 2-[(2,4-Dichloro-benzoyl)-(3,4-dimethoxy-phenyl)-amino]-5-methyl-thiazole-4-carboxylic acid and N,N,N'-Triethyl-ethane-1,2-diamine | 593.3 |

| Expl. No. | Structure | Systematic Name | Synthesised from: | MW found |
|---|---|---|---|---|
| 98 | 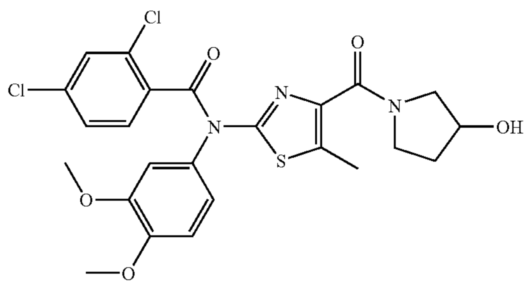 | 2,4-Dichloro-N-(3,4-dimethoxy-phenyl)-N-[4-(3-hydroxy-pyrrolidine-1-carbonyl)-5-methyl-thiazol-2-yl]-benzamide | 2-[(2,4-Dichloro-benzoyl)-(3,4-dimethoxy-phenyl)-amino]-5-methyl-thiazole-4-carboxylic acid and 3-hydroxy-pyrrolidine | 536.1 |
| 99 | 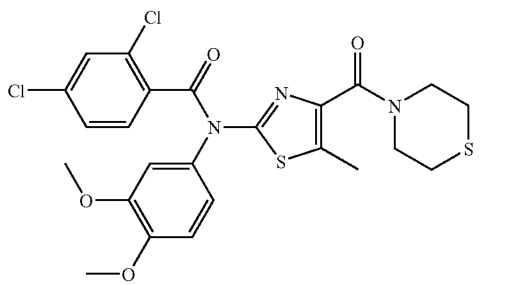 | 2,4-Dichloro-N-(3,4-dimethoxy-phenyl)-N-[5-methyl-4-(thiomorpholine-4-carbonyl)-thiazol-2-yl]-benzamide | 2-[(2,4-Dichloro-benzoyl)-(3,4-dimethoxy-phenyl)-amino]-5-methyl-thiazole-4-carboxylic acid and thiomorpholine | 552.2 |
| 100 | 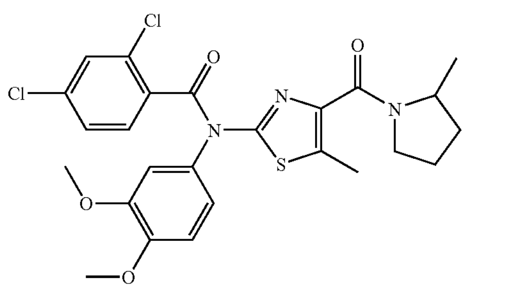 | 2,4-Dichloro-N-(3,4-dimethoxy-phenyl)-N-[5-methyl-4-(2-methyl-pyrrolidine-1-carbonyl)-thiazol-2-yl]-benzamide | 2-[(2,4-Dichloro-benzoyl)-(3,4-dimethoxy-phenyl)-amino]-5-methyl-thiazole-4-carboxylic acid and 2-methylpyrrolidine | 534.1 |
| 101 | 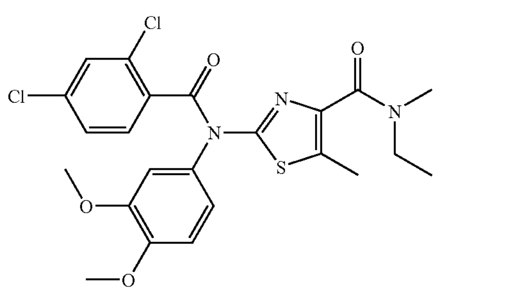 | 2-[(2,4-Dichloro-benzoyl)-(3,4-dimethoxy-phenyl)-amino]-5-methyl-thiazole-4-carboxylic acid ethyl-methyl-amide | 2-[(2,4-Dichloro-benzoyl)-(3,4-dimethoxy-phenyl)-amino]-5-methyl-thiazole-4-carboxylic acid and ethylmethylamine | 508.1 |
| 102 | 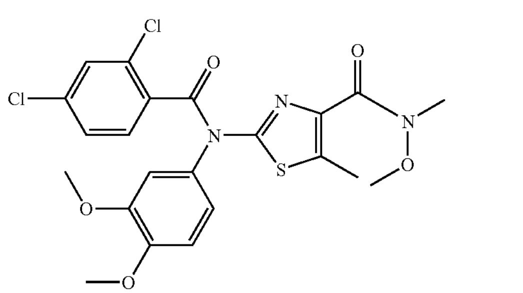 | 2-[(2,4-Dichloro-benzoyl)-(3,4-dimethoxy-phenyl)-amino]-5-methyl-thiazole-4-carboxylic acid methoxy-methyl-amide | 2-[(2,4-Dichloro-benzoyl)-(3,4-dimethoxy-phenyl)-amino]-5-methyl-thiazole-4-carboxylic acid and O,N-dimethyl-hydroxylamine hydrochloride | 510.1 |

| Expl. No. | Structure | Systematic Name | Synthesised from: | MW found |
|---|---|---|---|---|
| 103 | 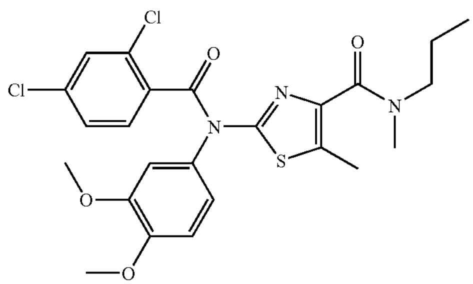 | 2-[(2,4-Dichloro-benzoyl)-(3,4-dimethoxy-phenyl)-amino]-5-methyl-thiazole-4-carboxylic acid methyl-propyl-amide | 2-[(2,4-Dichloro-benzoyl)-(3,4-dimethoxy-phenyl)-amino]-5-methyl-thiazole-4-carboxylic acid and n-propylmethylamine | 522.1 |
| 104 | 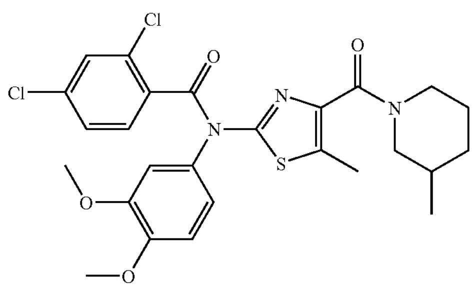 | 2,4-Dichloro-N-(3,4-dimethoxy-phenyl)-N-[5-methyl-4-(3-methyl-piperidine-1-carbonyl)-thiazol-2-yl]-benzamide | 2-[(2,4-Dichloro-benzoyl)-(3,4-dimethoxy-phenyl)-amino]-5-methyl-thiazole-4-carboxylic acid and 3-methylpiperidine | 548.1 |
| 105 | 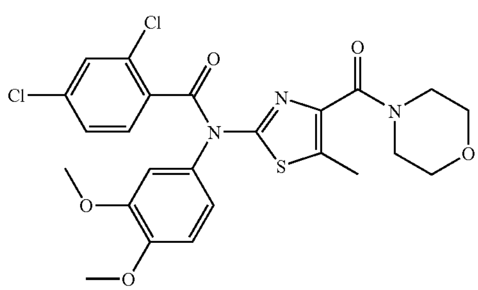 | 2,4-Dichloro-N-(3,4-dimethoxy-phenyl)-N-[5-methyl-4-(morpholine-4-carbonyl)-thiazol-2-yl]-benzamide | 2-[(2,4-Dichloro-benzoyl)-(3,4-dimethoxy-phenyl)-amino]-5-methyl-thiazole-4-carboxylic acid and morpholine | 536.1 |
| 106 | 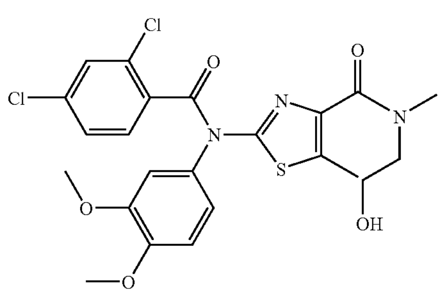 | 2-[(2,4-Dichloro-benzoyl)-(3,4-dimethoxy-phenyl)-amino]-5-methyl-thiazole-4-carboxylic acid (2-hydroxy-ethyl)-methyl-amide | 2-[(2,4-Dichloro-benzoyl)-(3,4-dimethoxy-phenyl)-amino]-5-methyl-thiazole-4-carboxylic acid and hydroxyethyl-methylamine | 524.2 |
| 107 | 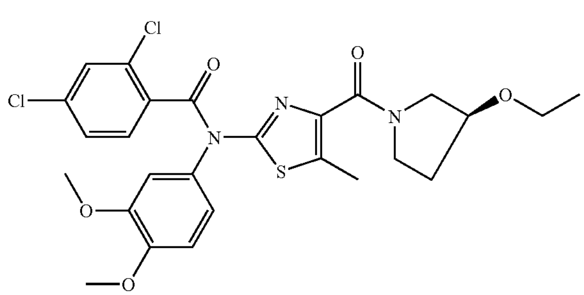 | 2,4-Dichloro-N-(3,4-dimethoxy-phenyl)-N-[4-(3-(S)-ethoxy-pyrrolidine-1-carbonyl)-5-methyl-thiazol-2-yl]-benzamide | 2-[(2,4-Dichloro-benzoyl)-(3,4-dimethoxy-phenyl)-amino]-5-methyl-thiazole-4-carboxylic acid and 3-(S)-ethoxy-pyrrolidine | 564.2 |

-continued

| Expl. No. | Structure | Systematic Name | Synthesised from: | MW found |
|---|---|---|---|---|
| 108 | 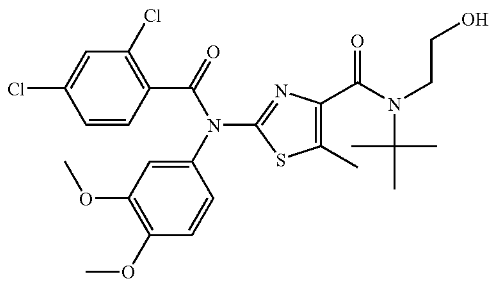 | 2-[(2,4-Dichlorro-benzoyl)-(3,4-dimethoxy-phenyl)-amino]-5-methyl-thiazole-4-carboxylic acid tert-butyl-(2-hydroxy-ethyl)-amide | 2-[(2,4-Dichloro-benzoyl)-(3,4-dimethoxy-phenyl)-amino]-5-methyl-thiazole-4-carboxylic acid and tert-butyl-(2-hydroxy-ethyl)-amine | 566.2 |
| 109 | 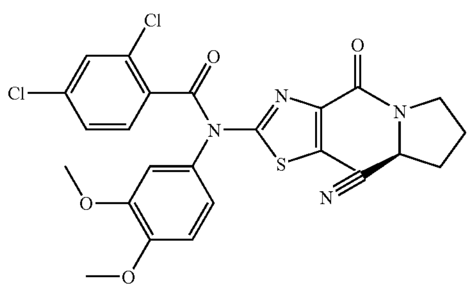 | 2,4-Dichloro-N-[4-(2-(R)-cyano-pyrrolidine-1-carbonyl)-5-methyl-thiazol-2-yl]-N-(3,4-dimethoxy-phenyl)-benzamide | 2-[(2,4-Dichloro-benzoyl)-(3,4-dimethoxy-phenyl)-amino]-5-methyl-thiazole-4-carboxylic acid and (2-(R)-cyano-pyrrolidine | 545.1 |
| 110 | 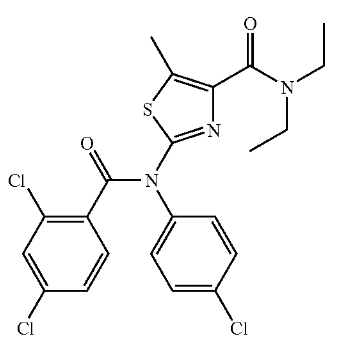 | 2-[(4-Chloro-phenyl)-(2,4-dichloro-benzoyl)-amino]-5-methyl-thiazole-4-carboxylic acid diethylamide | 2-[(4-Chloro-phenyl)-(2,4-dichloro-benzoyl)-amino]-5-methyl-thiazole-4-carboxylic acid and diethylamine | 496.0 |
| 111 | 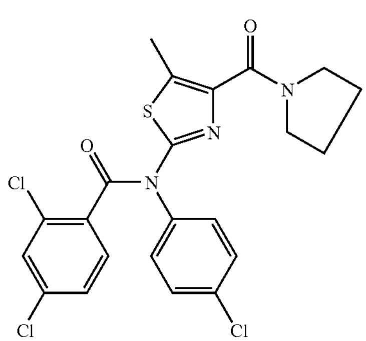 | 2,4-Dichloro-N-(4-chloro-phenyl)-N-[5-methyl-4-(pyrrolidine-1-carbonyl)-thiazol-2-yl]-benzamide | 2-[(4-Chloro-phenyl)-(2,4-dichloro-benzoyl)-amino]-5-methyl-thiazole-4-carboxylic acid and pyrrolidine | 496.1 |

-continued

| Expl. No. | Structure | Systematic Name | Synthesised from: | MW found |
|---|---|---|---|---|
| 112 | 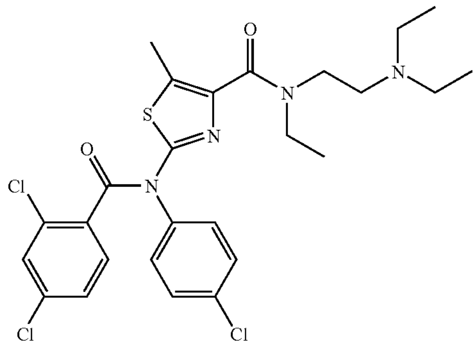 | 2-[(4-Chloro-phenyl)-(2,4-dichloro-benzoyl)-amino]-5-methyl-thiazole-4-carboxylic acid (2-diethylamino-ethyl)-ethyl-amide | 2-[(4-Chloro-phenyl)-(2,4-dichloro-benzoyl)-amino]-5-methyl-thiazole-4-carboxylic acid and N,N,N'-Triethyl-ethane-1,2-diamine | 569.1 |
| 113 | 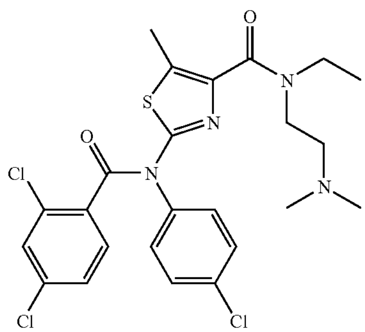 | 2-[(4-Chloro-phenyl)-(2,4-dichloro-benzoyl)-amino]-5-methyl-thiazole-4-carboxylic-acid (2-dimethylamino-ethyl)-ethyl-amide | 2-[(4-Chloro-phenyl)-(2,4-dichloro-benzoyl)-amino]-5-methyl-thiazole-4-carboxylic acid and N'-Ethyl-N,N-dimethyl-ethane-1,2-diamine | 539.1 |
| 114 | 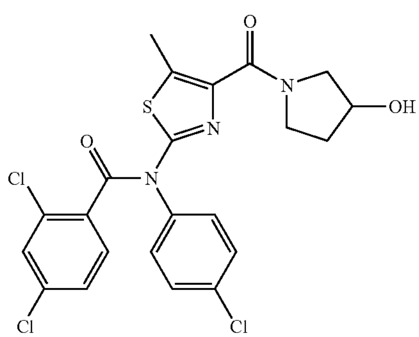 | 2,4-Dichloro-N-(4-chloro-phenyl)-N-[4-(3-hydroxy-pyrrolidine-1-carbonyl)-5-methyl-thiazol-2-yl]-benzamide | 2-[(4-Chloro-phenyl)-(2,4-dichloro-benzoyl)-amino]-5-methyl-thiazole-4-0carboxylic acid and 3-hydroxy-pyrrolidine | 511.9 |
| 115 | 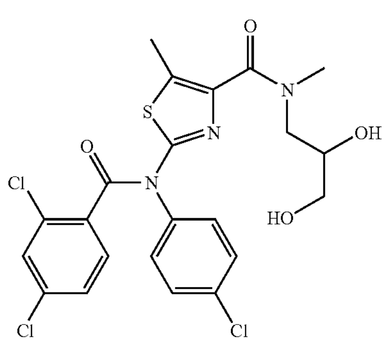 | 2-[(4-Chloro-phenyl)-(2,4-dichloro-benzoyl)-amino]-5-methyl-thiazole-4-carboxylic acid (2,3-dihydroxy-propyl)-methyl-amide | 2-[(4-Chloro-phenyl)-(2,4-dichloro-benzoyl)-amino]-5-methyl-thiazole-4-carboxylic acid and (2,3-dihydroxy-propyl)-methyl-amine | 530.0 |

-continued

| Expl. No. | Structure | Systematic Name | Synthesised from: | MW found |
|---|---|---|---|---|
| 116 | 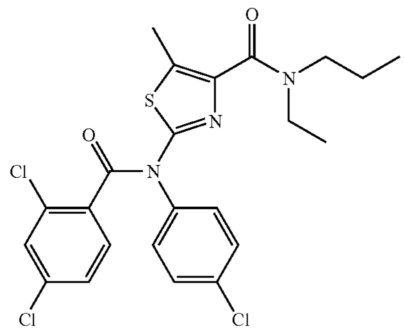 | 2-[(4-Chloro-phenyl)-(2,4-dichloro-benzoyl)-amino]-5-methyl-thiazole-4-carboxylic acid ethyl-propyl-amide | 2-[(4-Chloro-phenyl)-(2,4-dichloro-benzoyl)-amino]-5-methyl-thiazole-4-carboxylic acid and ethyl-n-propyl amine | 512.0 |
| 117 | 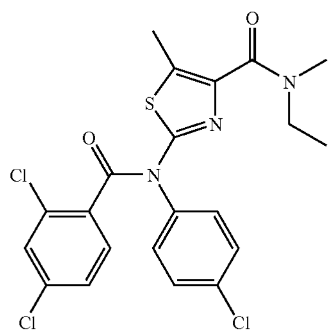 | 2-[(4-Chloro-phenyl)-(2,4-dichloro-benzoyl)-amino]-5-methyl-thiazole-4-carboxylic acid ethyl-methyl-amide | 2-[(4-Chloro-phenyl)-(2,4-dichloro-benzoyl)-amino]-5-methyl-thiazole-4-carboxylic acid and ethylmethyl amine | 483.9 |
| 118 | 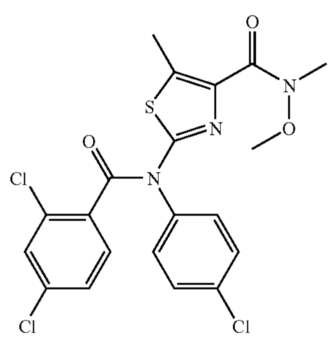 | 2-[(4-Chloro-phenyl)-(2,4-dichloro-benzoyl)-amino]-5-methyl-thiazole-4-carboxylic acid methoxy-methyl-amide | 2-[(4-Chloro-phenyl)-(2,4-dichloro-benzoyl)-amino]-5-methyl-thiazole-4-carboxylic acid and O,N-dimethyl-hydroxylamine hydrochloride | 486.0 |
| 119 | 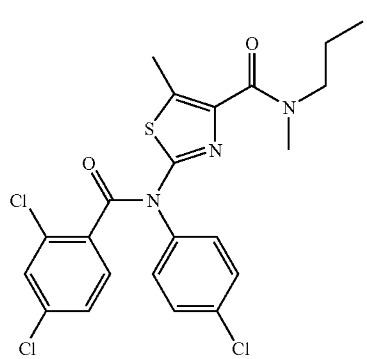 | 2-[(4-Chloro-phenyl)-(2,4-dichloro-benzoyl)-amino]-5-methyl-thiazole-4-carboxylic acid methyl-propyl-amide | 2-[(4-Chloro-phenyl)-(2,4-dichloro-benzoyl)-amino]-5-methyl-thiazole-4-carboxylic acid and methyl-n-propylamine | 497.9 |

| Expl. No. | Structure | Systematic Name | Synthesised from: | MW found |
|---|---|---|---|---|
| 120 | 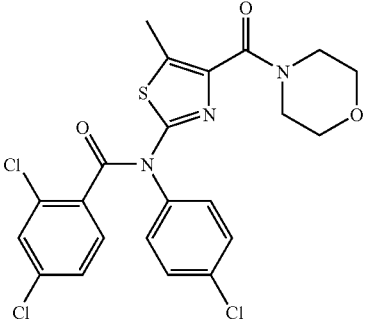 | 2,4-Dichloro-N-(4-chloro-phenyl)-N-[5-methyl-4-(morpholine-4-carbonyl)-thiazol-2-yl]-benzamide | 2-[(4-Chloro-phenyl)-(2,4-dichloro-benzoyl)-amino]-5-methyl-thiazole-4-carboxylic acid and morpholine | 511.9 |
| 121 | 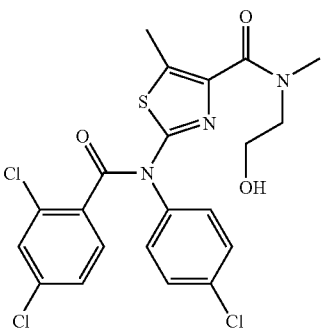 | 2-[(4-Chloro-phenyl)-(2,4-dichloro-benzoyl)-amino]-5-methyl-thiazole-4-carboxylic acid (2-hydroxy-ethyl)-methyl-amide | 2-[(4-Chloro-phenyl)-(2,4-dichloro-benzoyl)-amino]-5-methyl-thiazole-4-carboxylic acid and (2-hydroxy-ethyl)-methyl-amine | 498.0 |
| 122 | 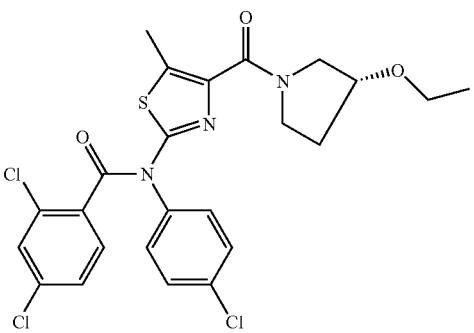 | 2,4-Dichloro-N-(4-chloro-phenyl)-N-[4-(3-(R)-ethoxy-pyrrolidine-1-carbonyl)-5-methyl-thiazzol-2-yl]-benzamide | 2-[(4-Chloro-phenyl)-(2,4-dichloro-benzyl)-amino]-5-methyl-thiazole-4-carboxylic acid and 3-(R)-ethoxy-pyrrolidine | 540.1 |
| 123 | 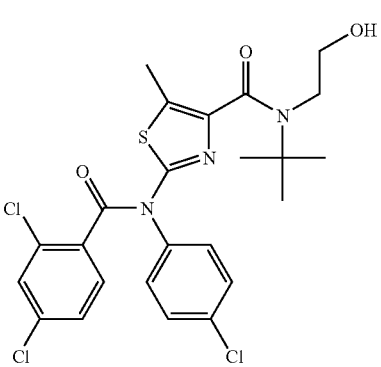 | 2-[(4-Chloro-phenyl)-(2,4-dichloro-benzoyl)-amino]-5-methyl-thiazole-4-carboxylic acid tert-butyl-(2-hydroxy-ethyl)-amide | 2-[(4-Chloro-phenyl)-(2,4-dichloro-benzoyl)-amino]-5-methyl-thiazole-4-carboxylic acid and tert-butyl-(2-hydroxy-ethyl)-amine | 541.9 |

| Expl. No. | Structure | Systematic Name | Synthesised from: | MW found |
|---|---|---|---|---|
| 124 | 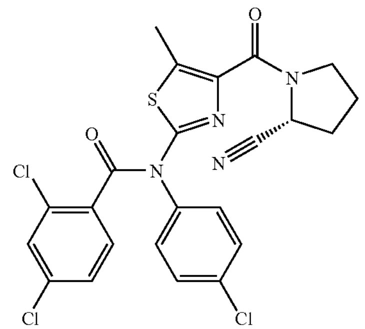 | 2,4-Dichloro-N-(4-chloro-phenyl)-N-[4-(2-(R)-cyano-pyrrolidine-1-carbonyl)-5-methyl-thiazol-2-yl]-benzamide | 2-[(4-Chloro-phenyl)-(2,4-dichloro-benzoyl)-amino]-5-methyl-thiazole-4-carboxylic acid and 2-(R)-cyano-pyrrolidine | 521.1 |

Example 125

2-[(2,4-Dichloro-benzoyl)-(3,4-dimethoxy-phenyl)-amino]-thiazole-5-carboxylic acid diethylamide

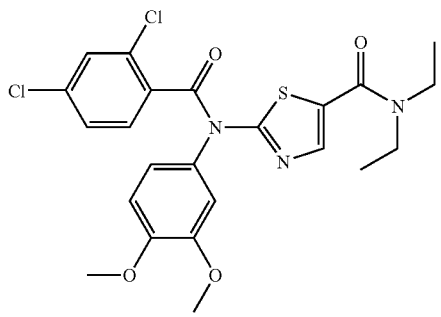

A mixture of 2.39 g (8.5 mmol) 2-(3,4-Dimethoxy-phenylamino)-thiazole-5-carboxylic acid, 2.38 ml (17 mmol) 2,4-Dichlorobenzoyl chloride and 3.35 ml (25.6 mmol) NEt$_3$ in 50 ml THF was stirred at room temperature for 16 h and evaporated to dryness. The intermediately built 2-[(2,4-Dichloro-benzoyl)-(3,4-dimethoxy-phenyl)-amino]-thiazole-5-carboxylic acid was identified by MS analysis (m/e): 452.9 (M+H$^+$, 100%) and used without further purification in the consecutive step. A mixture of 31.7 mg (0.07 mmol) 2-[(2,4-Dichloro-benzoyl)-(3,4-dimethoxy-phenyl)-amino]-thiazole-5-carboxylic acid, 14.8 mg (0.091 mmol) Carbonyldimidazole and 12.8 mg (0.175 mmol) diethylamine in 1.2 ml DMF was stirred at room temperature for 16 h. The mixture was directly subjected to reversed phase HPLC purification eluting with an acetonitrile/water gradient to yield after evaporation of the product fractions 6.8 mg (19%) of the title compound. MS (m/e): 508.1 (MH$^+$, 100%)

According to the procedure described for the synthesis of Example 125 further derivatives have been synthesised from 2-[(2,4-Dichloro-benzoyl)-(3,4-dimethoxy-phenyl)-amino]-thiazole-5-carboxylic acid and various commercially available amines and comprise Examples 126-Example 135 below. In cases of Example 135 additionally 2 eq. NEt$_3$ were added to the reaction mixture as the amine hydochloride was used as starting material.

Examples 126-135

The following compounds have been prepared in analogy to the process described in Example 125:

| Expl. No. | Structure | Systematic Name | Synthesised from: | MW found |
|---|---|---|---|---|
| 126 | 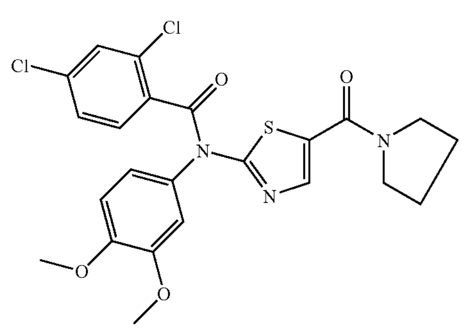 | 2,4-Dichloro-N-(3,4-dimethoxy-phenyl)-N-[5-(pyrrolidine-1-carbonyl)-thiazol-2-yl]-benzamide | 2-[(2,4-Dichloro-benzoyl)-(3,4-dimethoxy-phenyl)-amino]-thiazole-5-carboxylic acid and pyrrolidine | 506.1 |

-continued

| Expl. No. | Structure | Systematic Name | Synthesised from: | MW found |
|---|---|---|---|---|
| 127 | 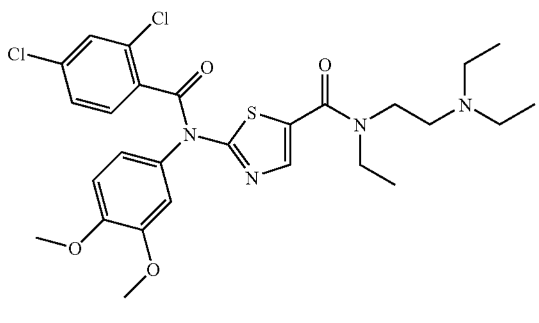 | 2-[(2,4-Dichloro-benzoyl)-(3,4-dimethoxy-phenyl)-amino]-thiazole-5-carboxylic acid(2-diethylamino-ethyl)-ethyl-amide | 2-[(2,4-Dichloro-benzoyl)-(3,4-dimethoxy-phenyl)-amino]-thiazole-5-carboxylic acid and(2-diethylamino-ethyl)-ethyl-amine | 579.2 |
| 128 | 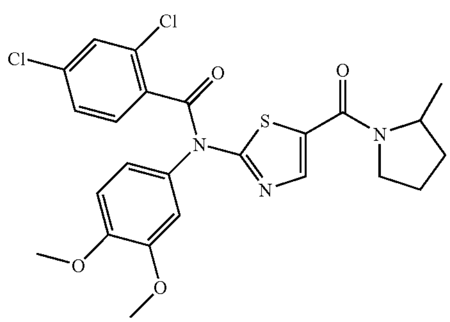 | 2,4-Dichloro-N-(3,4-dimethoxy-phenyl)-N-[5-(2-methyl-pyrrolidine-1-carbonyl)-thiazol-2-yl]-benzamide | 2-[(2,4-Dichloro-benzoyl)-(3,4-dimethoxy-phenyl)-amino]-thiazole-5-carboxylic acid and 2-methyl-pyrrolidine | 520.1 |
| 129 | 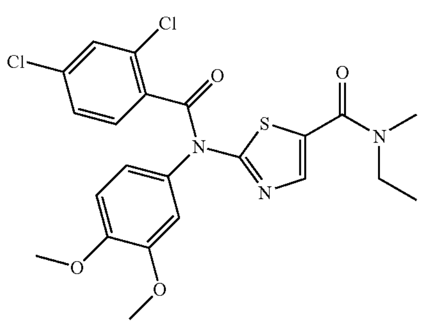 | 2-[(2,4-Dichloro-benzoyl)-(3,4-dimethoxy-phenyl)-amino]-thiazole-5-carboxylic acid ethyl-methyl-amide | 2-[(2,4-Dichloro-benzoyl)-(3,4-dimethoxy-phenyl)-amino]-thiazole-5-carboxylic acid and ethylmethylamine | 495.9 |
| 130 | 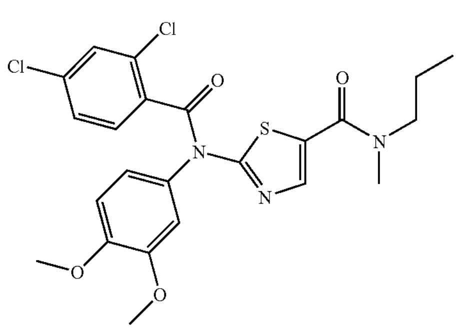 | 2-[(2,4-Dichloro-benzoyl)-(3,4-dimethoxy-phenyl)-amino]-thiazole-5-carboxylic acid methyl-propyl-amide | 2-[(2,4-Dichloro-benzoyl)-(3,4-dimethoxy-phenyl)-amino]-thiazole-5-carboxylic acid and methyl-n-propylamine | 508.1 |

-continued

| Expl. No. | Structure | Systematic Name | Synthesised from: | MW found |
|---|---|---|---|---|
| 131 | 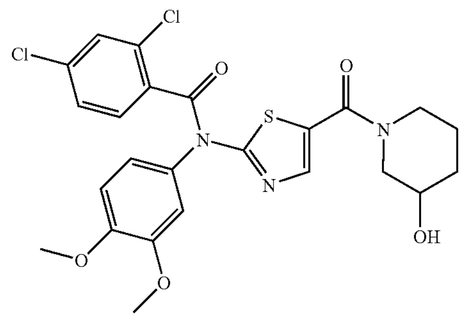 | 2,4-Dichloro-N-(3,4-di-methoxy-phenyl)-N-[5-(3-hydroxy-piperidine-1-carbonyl)-thiazol-2-yl]-benzamide | 2-[(2,4-Dichloro-benzoyl)-(3,4-dimethoxy-phenyl)-amino]-thiazole-5-carboxylic acid and 3-hydroxypiperidine | 536.1 |
| 132 | 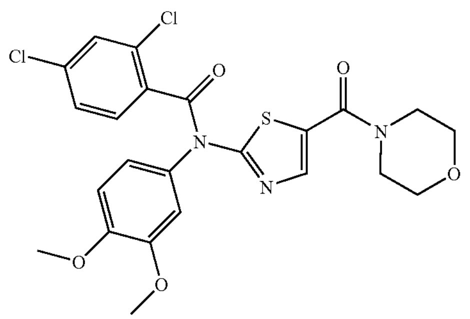 | 2,4-Dichloro-N-(3,4-dimethoxy-phenyl)-N-[5-(morpholine-4-carbonyl)-thiazol-2-yl]-benzamide | 2-[(2,4-Dichloro-benzoyl)-(3,4-dimethoxy-phenyl)-amino]-thiazole-5-carboxylic acid and morpholine | 522.1 |
| 133 | 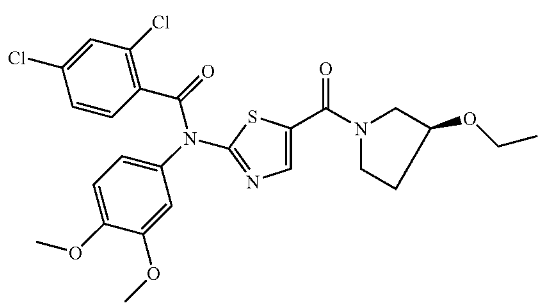 | 2,4-Dichloro-N-(3,4-dimethoxy-phenyl)-N-[5-(3-(R)-ethoxy-pyrrolidine-1-carbonyl)-thiazol-2-yl]-benzamide | 2-[(2,4-Dichloro-benzoyl)-(3,4-dimethoxy-phenyl)-amino]-thiazole-5-carboxylic acid and 3-(R)-ethoxy-pyrrolidine | 550.2 |
| 134 | 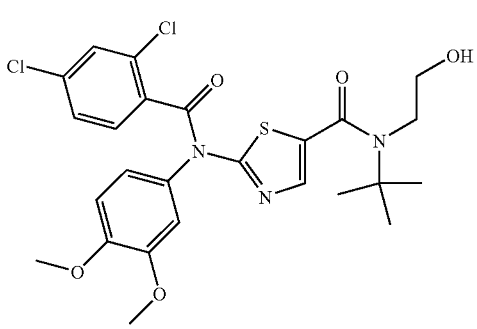 | 2-[(2,4-Dichloro-benzoyl)-(3,4-dimethoxy-phenyl)-amino]-thiazole-5-carboxylic acid tert-butyl-(2-hydroxy-ethyl)-amide | 2-[(2,4-Dichloro-benzoyl)-(3,4-dimethoxy-phenyl)-amino]-thiazole-5-carboxylic acid and tert-butyl-(2-hydroxy-ethyl)-amine | 552.2 |

-continued

| Expl. No. | Structure | Systematic Name | Synthesised from: | MW found |
|---|---|---|---|---|
| 135 | 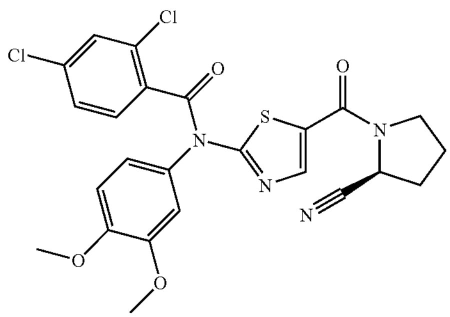 | 2,4-Dichloro-N-[5-(2-(R)-cyano-pyrrolidine-1-carbonyl)-thiazol-2-yl]-N-(3,4-dimethoxy-phenyl)-benzamide | 2-[(2,4-Dichloro-benzoyl)-(3,4-dimethoxy-phenyl)-amino]-thiazole-5-carboxylic acid and 2-(R)-cyano-pyrrolidine | 531.0 |

Example 136

2,4-Dichloro-N-(4-chloro-phenyl)-N-[5-(pyrrolidine-1-carbonyl)-thiazol-2-yl]-benzamide

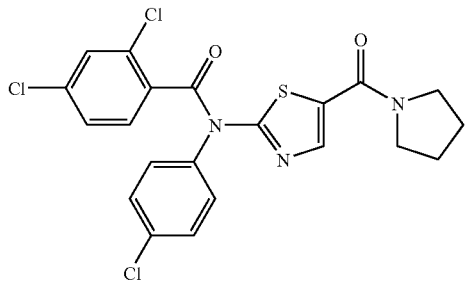

A mixture of 2.0 g (7.8 mmol) 2-(4-Chloro-phenylamino)-thiazole-5-carboxylic acid, 1.65 ml (11.8 mmol) 2,4-Dichlorobenzoyl chloride and 3.27 ml (23.5 mmol) NEt₃ in 30 ml DCM was stirred at toom temperature for 2 h and evaporated to dryness. The intermediately built 2-[(2,4-Dichloro-benzoyl)-(4-chloro-phenyl)-amino]-thiazole-5-carboxylic acid was identified by MS analysis (m/e): 429.0(M+H$^+$, 100%) and used without further purification in the consecutive step. A mixture of 30 mg (0.07 mmol) 2-[(2,4-Dichloro-benzoyl)-(4-chloro-phenyl)-amino]-thiazole-5-carboxylic acid, 14.8 mg (0.091 mmol) Carbonyldimimidazole and 12.5 mg (0.175 mmol) pyrrolidine in 1.2 ml DMF was stirred at room temperature for 16 h. The mixture was directly subjected to reversed phase HPLC purification eluting with an acetonitrile/water gradient to yield after evaporation of the product fractions 17.9 mg (53%) of the title compound. MS (m/e): 482.0 (MH$^+$, 100%)

According to the procedure described fort he synthesis of Example 136 further derivatives have been synthesised from 2-[(4-Chloro-phenyl)-(2,4-dichloro-benzoyl)-amino]-thiazole-5-carboxylic acid and various commercially available amines and comprise Examples 137-Example 146 below. In cases of Example 143 additionally 2 eq. NEt₃ were added to the reaction mixture as the amine hydochloride was used as starting material.

Examples 137-146

The following compounds have been prepared in analogy to the process described in Example 136:

| Expl. No. | Structure | Systematic Name | Synthesised from: | MW found |
|---|---|---|---|---|
| 137 | 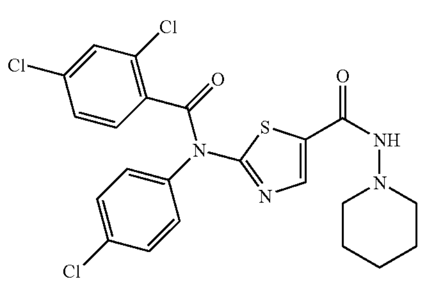 | 2-[(4-Chloro-phenyl)-(2,4-dichloro-benzoyl)-amino]-thiazole-5-carboxylic acid piperidin-1-ylamide | 2-[(4-Chloro-phenyl)-(2,4-dichloro-benzoyl)-amino]-thiazole-5-carboxylic acid and 1-amino-piperidine | 511.0 |

| Expl. No. | Structure | Systematic Name | Synthesised from: | MW found |
|---|---|---|---|---|
| 138 | 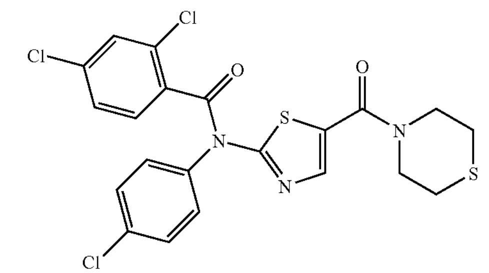 | 2,4-Dichloro-N-(4-chloro-phenyl)-N-[5-(thiomorpholine-4-carbonyl)-thiazol-2-yl]-benzamide | 2-[(4-Chloro-phenyl)-(2,4-dichloro-benzoyl)-amino]-thiazole-5-carboxylic acid and thiomorpholine | 513.9 |
| 139 | 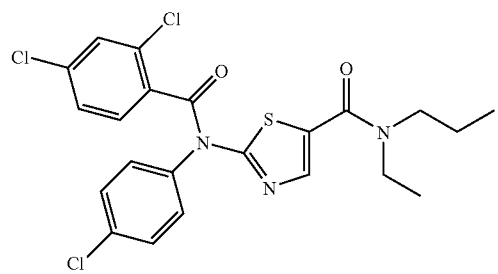 | 2-[(4-Chloro-phenyl)-(2,4-dichloro-benzoyl)-amino]-thiazole-5-carboxylic acid ethyl-propyl-amide | 2-[(4-Chloro-phenyl)-(2,4-dichloro-benzoyl)-amino]-thiazole-5-carboxylic acid and ethyl-n-propyl-amide | 497.9 |
| 140 | 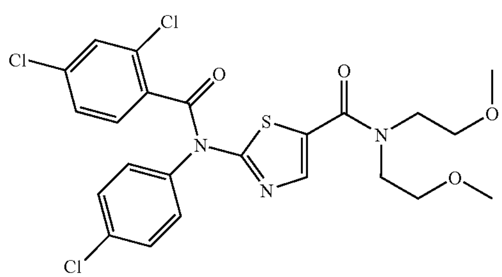 | 2-[(4-Chloro-phenyl)-(2,4-dichloro-benzoyl)-amino]-thiazole-5-carboxylic acid bis-(2-methoxy-ethyl)-amide | 2-[(4-Chloro-phenyl)-(2,4-dichloro-benzoyl)-amino]-thiazole-5-carboxylic acid and bis-(2-methoxy-ethyl)-amine | 543.9 |
| 141 | 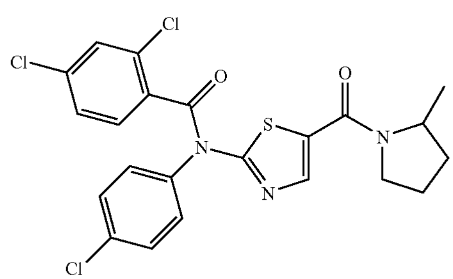 | 2,4-Dichloro-N-(4-chloro-phenyl)-N-[5-(2-methyl-pyrrolidine-1-carbonyl)-thiazol-2-yl]-benzamide | 2-[(4-Chloro-phenyl)-(2,4-dichloro-benzoyl)-amino]-thiazole-5-carboxylic acid and 2-methylpyrrolidine | 494.8 |
| 142 | 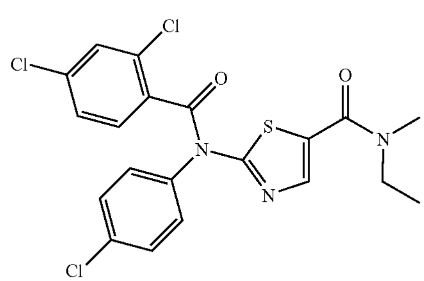 | 2-[(4-Chloro-phenyl)-(2,4-dichloro-benzoyl)-amino]-thiazole-5-carboxylic acid ethyl-methyl-amide | 2-[(4-Chloro-phenyl)-(2,4-dichloro-benzoyl)-amino]-thiazole-5-carboxylic acid and ethylmethylamine | 470.0 |

-continued

| Expl. No. | Structure | Systematic Name | Synthesised from: | MW found |
|---|---|---|---|---|
| 143 | 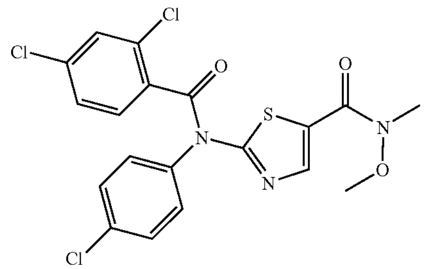 | 2-[(4-Chloro-phenyl)-(2,4-di-chloro-benzoyl)-a-mino]-thiazole-5-carboxylic acid methoxy-methyl-amide | 2-[(4-Chloro-phenyl)-(2,4-di-chloro-benzoyl)-a-mino]-thiazole-5-carboxylic acid and O,N-dimethyl-hydroxylamine hydrochloride | 472.0 |
| 144 | 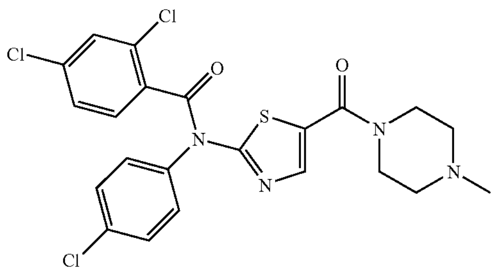 | 2,4-Dichloro-N-(4-chloro-phenyl)-N-[5-(4-methyl-piperazine-1-carbonyl)-thiazol-2-yl]-benzamide | 2-[(4-Chloro-phenyl)-(2,4-di-chloro-benzoyl)-a-mino]-thiazole-5-carboxylic acid and N-methylpiperazine | 511.0 |
| 145 | 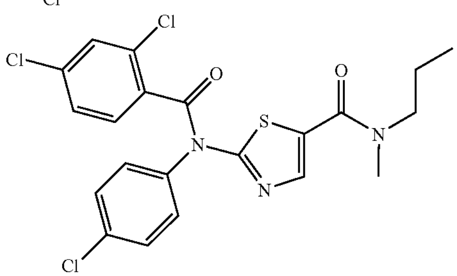 | 2-[(4-Chloro-phenyl)-(2,4-di-chloro-benzoyl)-a-mino]-thiazole-5-carboxylic acid methyl-propyl-amide | 2-[(4-Chloro-phenyl)-(2,4-di-chloro-benzoyl)-a-mino]-thiazole-5-carboxylic acid and methyl-n-propylamine | 484.0 |
| 146 | 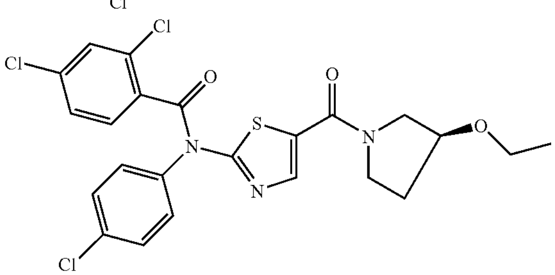 | 2,4-Dichloro-N-(4-chloro-phenyl)-N-[5-(3-(R)-ethoxy-pyrrolidine-1-carbonyl)-thiazol-2-yl]-benzamide | 2-[(4-Chloro-phenyl)-(2,4-di-chloro-benzoyl)-a-mino]-thiazole-5-carboxylic acid and 3-(R)-ethoxy-pyrrolidine | 526.0 |

Example 147

2,4-Dichloro-N-[4-(pyrrolidine-1-carbonyl)thiazole-2-yl]-N-(4-trifluoromethoxy-phenyl)-benzamide

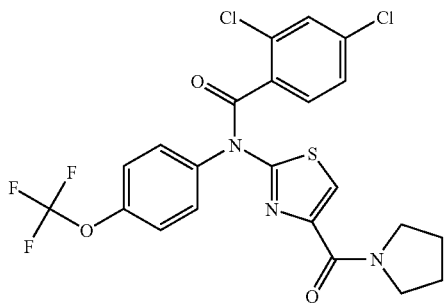

A mixture of 250 mg (0.52 mmol) 2-[(2,4-dichloro-benzoyl)-(4-trifluoromethoxy-phenyl)-amino]-thiazole-4-carboxylic acid, 57 μL (0.68 mmol) pyrrolidine and 110 mg (0.68 mmol) 1,1'-carbonyldiimidazole in 10 mL dichloromethane was stirred for 16 h at room temperature. The mixture was poured onto 0.5 N hydrochloric acid and extracted with dichloromethane. Organic phases were pooled, washed with water and brine and dried with $MgSO_4$. Volatiles were removed in vacuo and the residue was purified by silica gel chromatography (n-heptane/ethyl acetate 1:1) to yield 182 mg (65%) of the title compound as colorless solid. MS (m/e): 530.0 ($MH^+$)

According to the procedure described for the synthesis of Example 147 further derivatives have been synthesized from 2-[(2-chloro-benzoyl)-(4-trifluoromethoxyphenyl)-amino]-thiazole-4-carboxylic acid, 2-[(2-chloro-4-fluoro-benzoyl)-(4-trifluoromethoxyphenyl)-amino]-thiazole-4-carboxylic acid, 2-[(2,4-dichloro-benzoyl)-(4-trifluoromethoxyphenyl)-amino]-thiazole-4-carboxylic acid and 2-[(2,4-dichloro-benzoyl)-(4-chloro-3-methoxy-phenyl)-amino]-thiazole-4-carboxylic acid with various commercially available amines and comprise Examples 148-Example 160 below.

Examples 148-160

The following compounds have been prepared in analogy to the process described in Example 147:

| Expl. No. | Structure | Systematic Name | Synthesised from: | MW found |
|---|---|---|---|---|
| 148 | 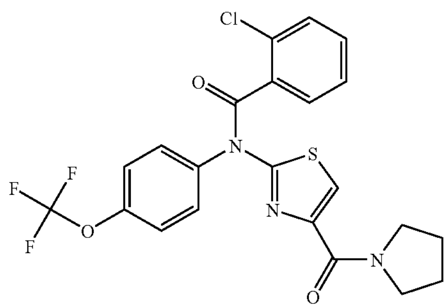 | 2-Chloro-N-[4-(pyrrolidine-1-carbonyl)-thiazol-2-yl]-N-(4-trifluoromethoxy-phenyl)-benzamide | 2-[(2-Chloro-benzoyl)-(4-trifluoromethoxyphenyl)-amino]-thiazole-4-carboxylic acid and pyrrolidine | 496.1 (MH$^+$) |
| 149 | 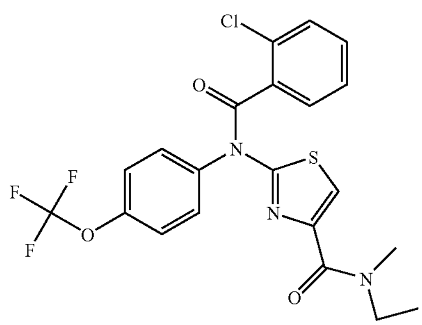 | 2-[(2-Chloro-benzoyl)-(4-trifluoromethoxy-phenyl)-amino]-thiazole-4-carboxylic acid ethyl-methyl-amide | 2-[(2-Chloro-benzoyl)-(4-trifluoromethoxyphenyl)-amino]-thiazole-4-carboxylic acid and N-ethyl-methylamine | 484.3 (MH$^+$) |
| 150 | 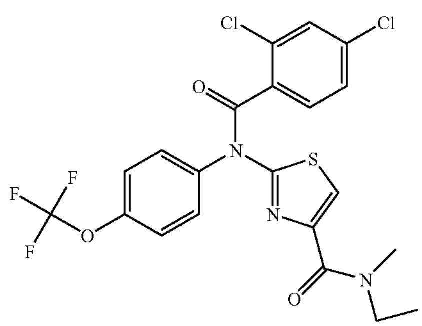 | 2-[(2,4-Dichloro-benzoyl)-(4-trifluoromethoxy-phenyl)-amino]-thiazole-4-carboxylic acid ethyl-methyl-amide | 2-[(2,4-Dichloro-benzoyl)-(4-trifluoromethoxyphenyl)-amino]-thiazole-4-carboxylic acid and N-ethyl-methylamine | 518.1 (MH$^+$) |
| 151 | 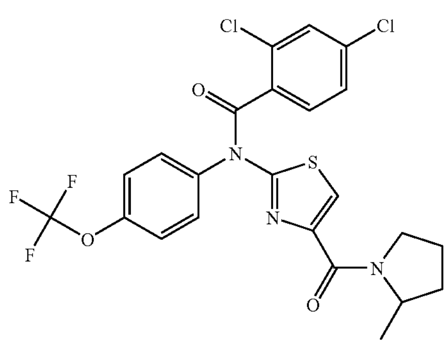 | rac-2,4-Dichloro-N-[4-(2-methyl-pyrrolidine-1-carbonyl)-thiazol-2-yl]-N-(4-trifluoromethoxy-phenyl)-benzamide | 2-[(2,4-Dichloro-benzoyl)-(4-trifluoromethoxyphenyl)-amino]-thiazole-4-carboxylic acid and rac-2-methyl-pyrrolidine | 544.2, 546.2 (MH$^+$) |

-continued

| Expl. No. | Structure | Systematic Name | Synthesised from: | MW found |
|---|---|---|---|---|
| 152 | 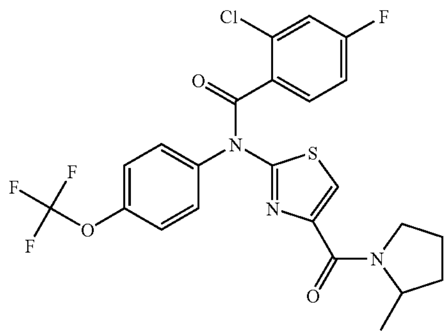 | rac-2-Chloro-4-fluoro-N-[4-(2-methyl-pyrrolidine-1-carbonyl)-thiazol-2-yl]-N-(4-trifluoromethoxy-phenyl)-benzamide | 2-[(2-Chloro-4-fluoro-benzoyl)-(4-trifluoromethoxyphenyl)-amino]-thiazole-4-carboxylic acid and rac-2-methylpyrrolidine | 528.2 (MH+) |
| 153 | 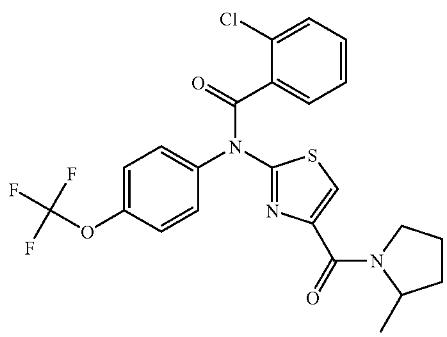 | rac-2-Chloro-N-[4-(2-methyl-pyrrolidine-1-carbonyl)-thiazol-2-yl]-N-(4-trifluoromethoxy-phenyl)-benzamide | 2-[(2-Chloro-benzoyl)-(4-trifluoromethoxyphenyl)-amino]-thiazole-4-carboxylic acid and rac-2-methyl-pyrrolidine | 510.3 (MH+) |
| 154 | 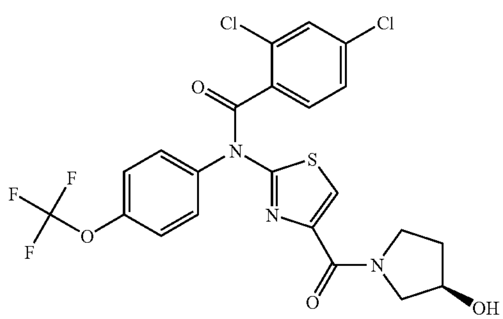 | 2,4-Dichloro-N-[4-(3(R)-hydroxy-pyrrolidine-1-carbonyl)-thiazol-2-yl]-N-(4-trifluoromethoxy-phenyl)-benzamide | 2-[(2,4-Dichloro-benzoyl)-(4-trifluoromethoxyphenyl)-amino]-thiazole-4-carboxylic acid and (R)-3-hydroxy-pyrrolidine | 546.1 (MH+) |
| 155 | 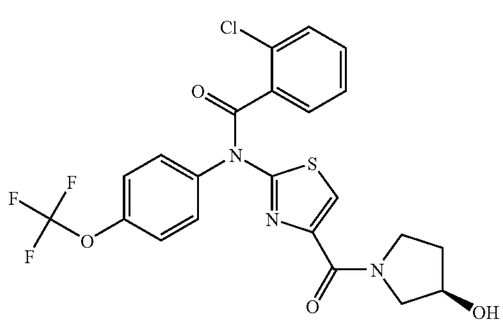 | 2-Chloro-N-[4-(3(R)-hydroxy-pyrrolidine-1-carbonyl)-thiazol-2-yl]-N-(4-trifluoromethoxy-phenyl)-benzamide | 2-[(2-Chloro-benzoyl)-(4-trifluoromethoxyphenyl)-amino]-thiazole-4-carboxylic acid and (R)-3-hydroxy-pyrrolidine | 512.2 (MH+) |

-continued

| Expl. No. | Structure | Systematic Name | Synthesised from: | MW found |
|---|---|---|---|---|
| 156 | 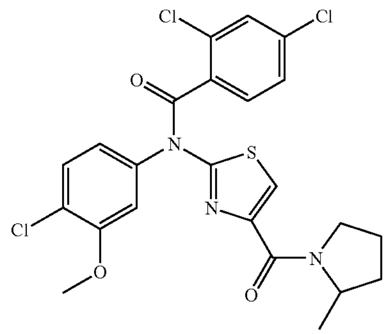 | rac-2,4-Dichloro-N-(4-chloro-3-methoxy-phenyl)-N-[4-(2-methyl-pyrrolidine-1-carbonyl)-thiazol-2-yl]-benzamide | 2-[(2,4-Dichloro-benzoyl)-(4-chloro-3-methoxy-phenyl)-amino]-thiazole-4-carboxylic acid and rac-2-methylpyrrolidine | 524.2 (MH$^+$) |
| 157 | 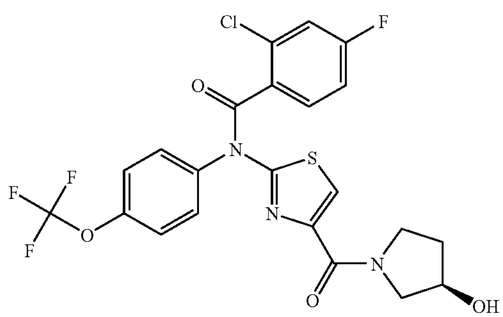 | 2-Chloro-4-fluoro-N-[4-((R)-3-hydroxy-pyrrolidine-1-carbonyl)-thiazol-2-yl]-N-(4-trifluoromethoxy-phenyl)-benzamide | 2-[(2-Chloro-4-fluoro-benzoyl)-(4-trifluoromethoxyphenyl)-amino]-thiazole-4-carboxylic acid and (R)-3-hydroxy-pyrrolidine | 530.0 (MH$^+$) |
| 158 | 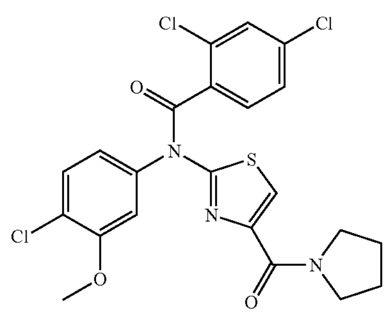 | 2,4-Dichloro-N-(4-chloro-3-methoxy-phenyl)-N-[4-(pyrrolidine-1-carbonyl)-thiazol-2-yl]-benzamide | 2-[(2,4-Dichloro-benzoyl)-(4-chloro-3-methoxy-phenyl)-amino]-thiazole-4-carboxylic acid and pyrrolidine | 510.2, 512.2 (MH$^+$) |
| 159 | 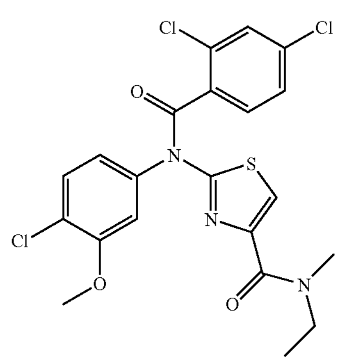 | 2-[(4-Chloro-3-methoxy-phenyl)-(2,4-dichloro-benzoyl)-amino]-thiazole-4-carboxylic acid ethyl-methyl-amide | 2-[(2,4-Dichloro-benzoyl)-(4-chloro-3-methoxy-phenyl)-amino]-thiazole-4-carboxylic acid and N-ethyl-methylamine | 498.1 (MH$^+$) |

| Expl. No. | Structure | Systematic Name | Synthesised from: | MW found |
|---|---|---|---|---|
| 160 | 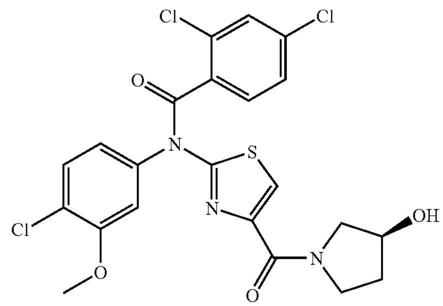 | 2,4-Dichloro-N-(4-chloro-3-methoxy-phenyl)-N-[4-((R)-3-hydroxy-pyrrolidine-1-carbonyl)-thiazol-2-yl]-benzamide | 2-[(2,4-Dichloro-benzoyl)-(4-chloro-3-methoxy-phenyl)-amino]-thiazole-4-carboxylic acid and (R)-3-hydroxypyrrolidine | 526.1 (MH⁺) |

Example 161

2,4-Dichloro-N-(4-chloro-3-methoxy-phenyl)-N-[4-(pyrrolidine-1-carbonyl)thiazole-2-yl]-benzamide

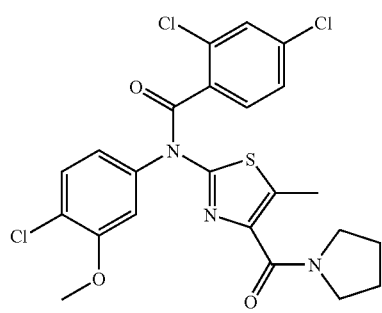

A mixture of 400 mg (0.85 mmol) 2-[(2,4-dichloro-benzoyl)-(4-chloro-3-methoxy-phenyl)-amino]-5-methyl-thiazole-4-carboxylic acid, 105 μL (1.27 mmol) pyrrolidine and 179 mg (1.10 mmol) 1,1'-carbonyldiimidazole in 12 mL dichloromethane was stirred for 16 h at room temperature. The mixture was poured onto 0.5 N hydrochloric acid and extracted with dichloromethane. Organic phases were pooled, washed with water and brine and dried with MgSO4. Volatiles were removed in vacuo and the residue was purified by silica gel chromatography (n-heptane/ethyl acetate 1:1) to yield 270 mg (60%) of the title compound as colorless solid. MS (m/e): 524.1, 526.1 (MH⁺)

According to the procedure described for the synthesis of Example 161 further derivatives have been synthesized from 2-[(2,4-dichloro-benzoyl)-(4-chloro-3-methoxy-phenyl)-amino]-5-methyl-thiazole-4-carboxylic acid with various commercially available amines and comprise Examples 162-Example 165 below.

Examples 162-165

The following compounds have been prepared in analogy to the process described in Example 161:

| Expl. No. | Structure | Systematic Name | Synthesised from: | MW found |
|---|---|---|---|---|
| 162 | 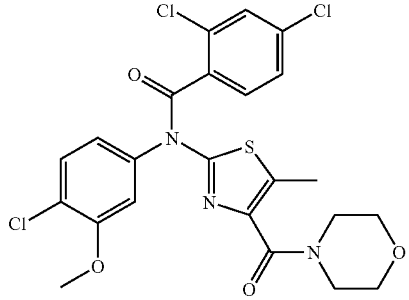 | 2,4-Dichloro-N-(4-chloro-3-methoxy-phenyl)-N-[5-methyl-4-(morpholine-4-carbonyl)-thiazol-2-yl]-benzamide | 2-(4-Chloro-3-methoxy-phenyl-amino)-5-methyl-thiazole-4-carboxylic acid and morpholine | 540.2 (MH⁺) |

-continued

| Expl. No. | Structure | Systematic Name | Synthesised from: | MW found |
|---|---|---|---|---|
| 163 | 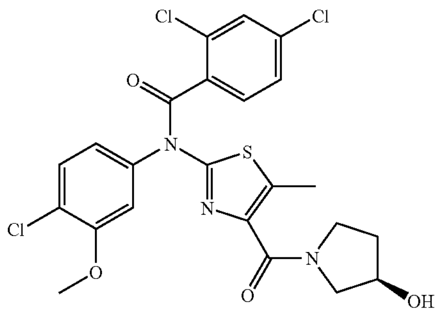 | 2,4-Dichloro-N-(4-chloro-3-methoxy-phenyl)-N-[4-((R)-3-hydroxy-pyrrolidine-1-carbonyl)-5-methyl-thiazol-2-yl]-benzamide | 2-(4-Chloro-3-methoxy-phenyl-amino)-5-methyl-thiazole-4-carboxylic acid and (R)-3-hydroxy-pyrrolidine | 540.2 (MH+) |
| 164 | 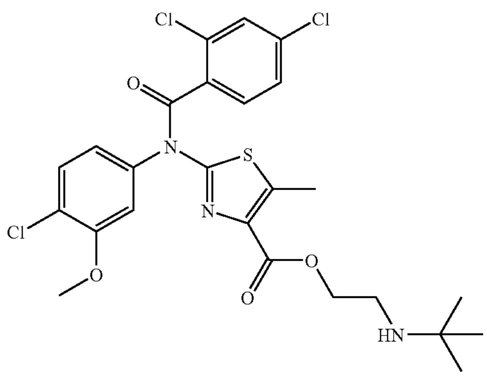 | 2-[(4-Chloro-3-methoxy-phenyl)-(2,4-dichloro-benzoyl)-amino]-5-methyl-thiazole-4-carboxylic acid 2-tert-butylamino-ethyl ester | 2-(4-Chloro-3-methoxy-phenyl-amino)-5-methyl-thiazole-4-carboxylic acid and 2-(tert-butyl-amino)ethanol | 570.2, 571.9 (MH+) |
| 165 | 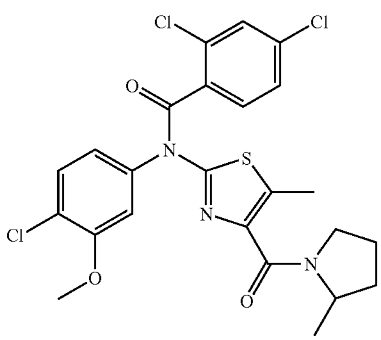 | rac-2,4-Dichloro-N-(4-chloro-3-methoxy-phenyl)-N-[5-methyl-4-(2-methyl-pyrrolidine-1-carbonyl)-thiazol-2-yl]-benzamide | 2-(4-Chloro-3-methoxy-phenyl-amino)-5-methyl-thiazole-4-carboxylic acid and rac-2-methyl-pyrrolidine | 538.2, 540.2 (MH+) |

Galenical Examples

Example A

Film coated tablets containing the following ingredients can be manufactured in a conventional manner:

| Ingredients | Per tablet | |
|---|---|---|
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titan dioxide | 0.8 mg | 1.6 mg |

The active ingredient is sieved and mixed with microcrystalline cellulose and the mixture is granulated with a solution of polyvinylpyrrolidone in water. The granulate is mixed with sodium starch glycolate and magnesium stearate and compressed to yield kernels of 120 or 350 mg respectively. The kernels are lacquered with an aq. solution/suspension of the above mentioned film coat.

Example B

Capsules containing the following ingredients can be manufactured in a conventional manner:

| Ingredients | Per capsule |
|---|---|
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example C

Injection solutions can have the following composition:

| Compound of formula (I) | 3.0 mg |
|---|---|
| Polyethylene glycol 400 | 150.0 mg |
| Acetic acid | q.s. ad pH 5.0 |
| Water for injection solutions | ad 1.0 ml |

The active ingredient is dissolved in a mixture of Polyethylene glycol 400 and water for injection (part). The pH is adjusted to 5.0 by addition of acetic acid. The volume is adjusted to 1.0 ml by addition of the residual amount of water. The solution is filtered, filled into vials using an appropriate overage and sterilized.

The invention claimed is:

1. A compound of the formula

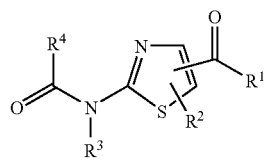

(I)

wherein $R^1$ is lower alkoxy, lower alkylamino-lower alkoxy, or —N($R^a$)$R^b$;

$R^a$ is hydrogen, lower alkyl, carbamoyl-lower alkyl, hydroxy-lower alkyl, di-hydroxy lower alkyl, lower alkinyl, lower alkoxy, lower alkoxy-lower alkyl, di-lower alkyl amino-lower alkyl, cycloalkyl; or $R^a$ is phenyl-lower alkyl residue, wherein the phenyl moiety may optionally be mono-, di- or tri-substituted, independently, by lower alkyl, lower alkoxy or halogen; or $R^a$ is a 5- or 6-membered heteroaromatic ring containing one or two nitrogen atoms in the ring, with the said heteroaromatic ring being attached to the remainder of the molecule by lower alkylene; or $R^a$ is a 5-, 6- or 7-membered saturated heterocyclic ring optionally containing one or two heteroatoms selected from nitrogen, oxygen and sulfur, said heterocyclic ring being optionally mono-, di-, or tri-substituted, independently, by lower alkyl;

$R^b$ is hydrogen, lower alkyl or lower alkoxy-lower alkyl; or $R^a$ and $R^b$ together with the nitrogen atom to which they are attached form a 4-, 5- or 6-membered saturated or unsaturated heterocyclic ring optionally containing a further heteroatom selected from nitrogen, oxygen and sulfur, said heterocyclic ring being optionally mono-, di-, or tri-substituted, independently, by lower alkyl, hydroxy, hydroxy-lower alkyl, lower alkoxy, lower alkoxy-lower alkyl, cyano, halogen, phenyl and/or benzyl;

$R^2$ is hydrogen or lower alkyl;

$R^3$ is phenyl mono-, di- or tri-substituted, independently, by lower alkoxy, halogen or perfluoro-lower alkoxy; and $R^4$ is a monocyclic aromatic ring optionally containing one or two nitrogen atoms in the ring, said ring being mono-, di- or tri-substituted, independently, by lower alkoxy, halogen or perfluoro-lower alkoxy;

or a pharmaceutically acceptable salt thereof.

2. The compound according to claim 1, wherein $R^1$ is —N($R^a$)$R^b$ and $R^a$ and $R^b$ are as defined above.

3. The compound according to claim 1, wherein $R^a$ is hydrogen, lower alkyl, carbamoyl-lower alkyl, hydroxy-lower alkyl, di-hydroxy lower alkyl, lower alkinyl, lower alkoxy, lower alkoxy-lower alkyl, di-lower alkyl amino-lower alkyl or cycloalkyl.

4. The compound according to claim 1, wherein $R^a$ is a phenyl-lower alkyl residue, wherein the phenyl moiety may optionally be mono-, di- or tri-substituted, independently, by lower alkyl, lower alkoxy or halogen.

5. The compound according to claim 1, wherein $R^a$ is a 5- or 6-membered heteroaromatic ring containing one or two nitrogen atoms in the ring, with the said heteroaromatic ring being attached to the remainder of the molecule by lower alkylene.

6. The compound according to claim 1, wherein $R^a$ is a 5-, 6- or 7-membered saturated heterocyclic ring optionally containing one or two heteroatoms selected from nitrogen, oxygen and sulfur, said heterocyclic ring being optionally mono-, di-, or tri-substituted, independently, by lower alkyl.

7. The compound according to claim 1, wherein $R^b$ is hydrogen or lower alkyl.

8. The compound according to claim 1, wherein $R^a$ and $R^b$ are independently lower alkoxy-lower alkyl.

9. The compound according to claim 1, wherein $R^a$ and $R^b$ together with the nitrogen atom to which they are attached form a 4-, 5- or 6-membered saturated or unsaturated heterocyclic ring optionally containing a further heteroatom selected from nitrogen, oxygen and sulfur, said heterocyclic ring being optionally mono-, di-, or tri-substituted, independently, by lower alkyl, hydroxy, hydroxy-lower alkyl, lower alkoxy, lower alkoxy-lower alkyl, cyano, halogen, phenyl or benzyl.

10. The compound according to claim 1, wherein $R^2$ is hydrogen attached to the carbon atom at the 4-position of the central thiazole ring.

11. The compound according to claim 1, wherein $R^2$ is hydrogen or lower alkyl attached to the carbon atom at the 5-position of the central thiazole ring.

12. The compound according to claim 1, wherein $R^3$ is a phenyl residue mono-substituted with halogen or with perfluoro-lower alkoxy.

13. The compound according to claim 1, wherein $R^3$ is a phenyl residue di-substituted, independently, by halogen or lower alkoxy.

14. The compound according to claim 1, wherein $R^4$ is pyridyl, pyrimidinyl or pyrazyl, mono- or di-substituted, independently, by lower alkoxy, halogen or by perfluoro-lower alkoxy.

15. The compound according to claim 1, wherein $R^4$ is phenyl which is mono-, di- or tri-substituted, independently, by lower alkoxy, halogen or perfluoro-lower alkoxy.

16. A pharmaceutical composition comprising an effective amount of a compound of claim 1 and a pharmaceutically acceptable carrier and/or adjuvant.

17. The compound according to claim 1 selected from the group consisting of:
- 2-[(2,4-dichloro-benzoyl)-(3,4-dimethoxy-phenyl)-amino]-thiazole-4-carboxylic acid ethyl ester,
- 2-[(2-chloro-benzoyl)-(3,4-dimethoxy-phenyl)-amino]-thiazole-4-carboxylic acid ethyl ester,
- 2,4-dichloro-N-(4-chloro-phenyl)-N-[4-(morpholine-4-carbonyl)-thiazol-2-yl]-benzamide,
- 2-[(4-chloro-phenyl)-(2,4-dichloro-benzoyl)-amino]-thiazole-4-carboxylic acid diethylamide,
- 2,4-dichloro-N-(4-chloro-phenyl)-N-[4-(pyrrolidine-1-carbonyl)-thiazol-2-yl]-benzamide,
- 2-[(4-chloro-phenyl)-(2,4-dichloro-benzoyl)-amino]-thiazole-4-carboxylic acid (2-dimethylamino-ethyl)-methyl-amide,
- 2-[(2-chloro-benzoyl)-(4-chloro-phenyl)-amino]-thiazole-4-carboxylic acid (2-dimethylamino-ethyl)-methyl-amide,
- 2,4-dichloro-N-(3,4-dimethoxy-phenyl)-N-[4-(morpholine-4-carbonyl)-thiazol-2-yl]-benzamide,
- 2-[(2,4-dichloro-benzoyl)-(3,4-dimethoxy-phenyl)-amino]-thiazole-4-carboxylic acid diethylamide,
- 2-[(2,4-dichloro-benzoyl)-(3,4-dimethoxy-phenyl)-amino]-thiazole-4-carboxylic acid benzylamide,
- 2,4-dichloro-N-(3,4-dimethoxy-phenyl)-N-[4-(pyrrolidine-1-carbonyl)-thiazol-2-yl]-benzamide,
- 2-[(2,4-dichloro-benzoyl)-(3,4-dimethoxy-phenyl)-amino]-thiazole-4-carboxylic acid cyclohexylamide,
- 2-[(2,4-dichloro-benzoyl)-(3,4-dimethoxy-phenyl)-amino]-thiazole-4-carboxylic acid (2-dimethylamino-ethyl)-methyl-amide,
- 2-[(2,4-dichloro-benzoyl)-(3,4-dimethoxy-phenyl)-amino]-thiazole-4-carboxylic acid 2-methyl-benzylamide,
- 2-[(2-chloro-benzoyl)-(3,4-dimethoxy-phenyl)-amino]-thiazole-4-carboxylic acid benzylamide,
- 2-chloro-N-(3,4-dimethoxy-phenyl)-N-[4-(pyrrolidine-1-carbonyl)-thiazol-2-yl]-benzamide,
- 2-[(2-chloro-benzoyl)-(3,4-dimethoxy-phenyl)-amino]-thiazole-4-carboxylic acid cyclohexylamide,
- 2-[(2-chloro-benzoyl)-(3,4-dimethoxy-phenyl)-amino]-thiazole-4-carboxylic acid 3-fluoro-benzylamide,
- 2-[(4-chloro-phenyl)-(2,4-dichloro-benzoyl)-amino]-thiazole-4-carboxylic acid ethyl-methyl-amide,
- 2-[(4-chloro-phenyl)-(2,4-dichloro-benzoyl)-amino]-thiazole-4-carboxylic acid methyl-phenethyl-amide,
- 2-[(4-chloro-phenyl)-(2,4-dichloro-benzoyl)-amino]-thiazole-4-carboxylic acid methyl-propyl-amide,
- 2-[(4-chloro-phenyl)-(2,4-dichloro-benzoyl)-amino]-thiazole-4-carboxylic acid ethyl-propyl-amide,
- 2,4-dichloro-N-(4-chloro-phenyl)-N-[4-(2-methyl-pyrrolidine-1-carbonyl)-thiazol-2-yl]-benzamide,
- 2,4-dichloro-N-(4-chloro-phenyl)-N-[4-(3-hydroxy-pyrrolidine-1-carbonyl)-thiazol-2-yl]-benzamide,
- 2-[(4-chloro-phenyl)-(2,4-dichloro-benzoyl)-amino]-thiazole-4-carboxylic acid azepan-1-ylamide,
- 2-[(4-chloro-phenyl)-(2,4-dichloro-benzoyl)-amino]-thiazole-4-carboxylic acid methyl-pentyl-amide,
- 2-[(4-chloro-phenyl)-(2,4-dichloro-benzoyl)-amino]-thiazole-4-carboxylic acid butyl-methyl-amide,
- N-[4-(azetidine-1-carbonyl)-thiazol-2-yl]-2,4-dichloro-N-(4-chloro-phenyl)-benzamide,
- 2-[(4-chloro-phenyl)-(2,4-dichloro-benzoyl)-amino]-thiazole-4-carboxylic acid dimethylamide,
- 2-[(4-chloro-phenyl)-(2,4-dichloro-benzoyl)-amino]-thiazole-4-carboxylic acid (2-diethylamino-ethyl)-ethyl-amide,
- 2,4-dichloro-N-(4-chloro-phenyl)-N-[4-(2-hydroxymethyl-pyrrolidine-1-carbonyl)-thiazol-2-yl]-benzamide,
- 2-[(4-chloro-phenyl)-(2,4-dichloro-benzoyl)-amino]-thiazole-4-carboxylic acid bis-(2-methoxy-ethyl)-amide,
- 2,4-dichloro-N-(4-chloro-phenyl)-N-[4-(2-(S)-methoxymethyl-pyrrolidine-1-carbonyl)-thiazol-2-yl]-benzamide,
- 2-[(4-chloro-phenyl)-(2,4-dichloro-benzoyl)-amino]-thiazole-4-carboxylic acid (1-methyl-3-phenyl-propyl)-amide,
- 2-[(4-chloro-phenyl)-(2,4-dichloro-benzoyl)-amino]-thiazole-4-carboxylic acid [2-(3,4-dimethoxy-phenyl)-ethyl]-methyl-amide,
- 2,4-dichloro-N-(4-chloro-phenyl)-N-[4-(4-methyl-piperazine-1-carbonyl)-thiazol-2-yl]-benzamide,
- 2,4-dichloro-N-(4-chloro-phenyl)-N-[4-(2-methyl-piperidine-1-carbonyl)-thiazol-2-yl]-benzamide,
- 2-[(4-chloro-phenyl)-(2,4-dichloro-benzoyl)-amino]-thiazole-4-carboxylic acid methyl-(2-pyndin-2-yl-ethyl)-amide,
- 2-[(4-chloro-phenyl)-(2,4-dichloro-benzoyl)-amino]-thiazole-4-carboxylic acid ethyl-(2-pyridin-2-yl-ethyl)-amide,
- 2,4-dichloro-N-(4-chloro-phenyl)-N-[4-(4-phenyl-piperazine-1-carbonyl)-thiazol-2-yl]-benzamide,
- 2-[(4-chloro-phenyl)-(2,4-dichloro-benzoyl)-amino]-thiazole-4-carboxylic acid amide,
- 2-[(4-chloro-phenyl)-(2,4-dichloro-benzoyl)-amino]-thiazole-4-carboxylic acid [2-(1H-imidazol-4-yl)-ethyl]-amide,
- 2-[(4-chloro-phenyl)-(2,4-dichloro-benzoyl)-amino]-thiazole-4-carboxylic acid (2,3-dihydroxy-propyl)-methyl-amide,
- 2,4-dichloro-N-(4-chloro-phenyl)-N-[4-(2,5-dihydro-pyrrole-1-carbonyl)-thiazol-2-yl]-benzamide,
- 2-[(4-chloro-phenyl)-(2,4-dichloro-benzoyl)-amino]-thiazole-4-carboxylic acid (4-methyl-piperazin-1-yl)-amide,
- 2-[(4-chloro-phenyl)-(2,4-dichloro-benzoyl)-amino]-thiazole-4-carboxylic acid (2-dimethylamino-ethyl)-ethyl-amide,
- 2-[(4-chloro-phenyl)-(2,4-dichloro-benzoyl)-amino]-thiazole-4-carboxylic acid (3-dimethylamino-propyl)-amide,
- 2-[(4-chloro-phenyl)-(2,4-dichloro-benzoyl)-amino]-thiazole-4-carboxylic acid methyl-prop-2-ynyl-amide,
- N-[4-(4-benzyl-piperidine-1-carbonyl)-thiazol-2-yl]-2,4-dichloro-N-(4-chloro-phenyl)-benzamide, 2,4-dichloro-N-(4-chloro-phenyl)-N-[4-(thiomorpholine-4-carbonyl)-thiazol-2-yl]-benzamide,
2-[(4-chloro-phenyl)-(2,4-dichloro-benzoyl)-amino]-thiazole-4-carboxylic acid (1-ethyl-piperidin-3-yl)-amide,
2-[(4-chloro-phenyl)-(2,4-dichloro-benzoyl)-amino]-thiazole-4-carboxylic acid carbamoylmethyl-amide,
2-[(4-chloro-phenyl)-(2,4-dichloro-benzoyl)-amino]-thiazole-4-carboxylic acid methoxy-methyl-amide,
2,4-dichloro-N-(4-chloro-phenyl)-N-[4-(3-(S)-hydroxy-pyrrolidine-1-carbonyl)-thiazol-2-yl]-benzamide,
2,4-dichloro-N-(4-chloro-phenyl)-N-[4-(3-(R)-hydroxy-pyrrolidine-1-carbonyl)-thiazol-2-yl]-benzamide,
2-chloro-N-(3,4-dimethoxy-phenyl)-N-[4-(2-methyl-pyrrolidine-1-carbonyl)-thiazol-2-yl]-benzamide,
2-[(2-chloro-benzoyl)-(3,4-dimethoxy-phenyl)-amino]-thiazole-4-carboxylic acid methoxy-methyl-amide,
2-[(2-chloro-benzoyl)-(4-chloro-phenyl)-amino]-thiazole-4-carboxylic acid (2-diethylamino-ethyl)-ethyl-amide,
2-[(2-chloro-benzoyl)-(4-chloro-phenyl)-amino]-thiazole-4-carboxylic acid (2-dimethylamino-ethyl)-ethyl-amide,
2-chloro-N-(4-chloro-phenyl)-N-[4-(2-(S)-methoxymethyl-pyrrolidine-1-carbonyl)-thiazol-2-yl]-benzamide,
2-chloro-N-(4-chloro-phenyl)-N-[4-(3-hydroxy-pyrrolidine-1-carbonyl)-thiazol-2-yl]-benzamide,
2-chloro-N-(4-chloro-phenyl)-N-[4-(thiomorpholine-4-carbonyl)-thiazol-2-yl]-benzamide,
2-[(2-chloro-benzoyl)-(4-chloro-phenyl)-amino]-thiazole-4-carboxylic acid ethyl-propyl-amide,
2-chloro-N-(4-chloro-phenyl)-N-[4-(2-methyl-pyrrolidine-1-carbonyl)-thiazol-2-yl]-benzamide,
2-[(2-chloro-benzoyl)-(4-chloro-phenyl)-amino]-thiazole-4-carboxylic acid ethyl-methyl-amide,
2-[(2-chloro-benzoyl)-(4-chloro-phenyl)-amino]-thiazole-4-carboxylic acid methoxy-methyl-amide,
2-chloro-N-(4-chloro-phenyl)-N-[4-(4-methyl-piperazine-1-carbonyl)-thiazol-2-yl]-benzamide,
2-[(2-chloro-benzoyl)-(4-chloro-phenyl)-amino]-thiazole-4-carboxylic acid methyl-propyl-amide,
2-[(2-chloro-benzoyl)-(4-chloro-phenyl)-amino]-thiazole-4-carboxylic acid carbamoylmethyl-amide,
2-[(2-chloro-benzoyl)-(4-chloro-phenyl)-amino]-thiazole-4-carboxylic acid amide,
2-[(2,4-dichloro-benzoyl)-(3,4-dimethoxy-phenyl)-amino]-thiazole-4-carboxylic acid (2-diethylamino-ethyl)-ethyl-amide,
2-[(2,4-dichloro-benzoyl)-(3,4-dimethoxy-phenyl)-amino]-thiazole-4-carboxylic acid (2-dimethylamino-ethyl)-ethyl-amide,
2,4-dichloro-N-(3,4-dimethoxy-phenyl)-N-[4-(2-(S)-methoxymethyl-pyrrolidine-1-carbonyl)-thiazol-2-yl]-benzamide,
2,4-dichloro-N-(3,4-dimethoxy-phenyl)-N-[4-(3-hydroxy-pyrrolidine-1-carbonyl)-thiazol-2-yl]-benzamide,
2,4-dichloro-N-(3,4-dimethoxy-phenyl)-N-[4-(thiomorpholine-4-carbonyl)-thiazol-2-yl]-benzamide,
2-[(2,4-dichloro-benzoyl)-(3,4-dimethoxy-phenyl)-amino]-thiazole-4-carboxylic acid ethyl-propyl-amide,
2-[(2,4-dichloro-benzoyl)-(3,4-dimethoxy-phenyl)-amino]-thiazole-4-carboxylic acid bis-(2-methoxy-ethyl)-amide,
2,4-dichloro-N-(3,4-dimethoxy-phenyl)-N-[4-(2-methyl-pyrrolidine-1-carbonyl)-thiazol-2-yl]-benzamide,
2-[(2,4-dichloro-benzoyl)-(3,4-dimethoxy-phenyl)-amino]-thiazole-4-carboxylic acid ethyl-methyl-amide,
2-[(2,4-dichloro-benzoyl)-(3,4-dimethoxy-phenyl)-amino]-thiazole-4-carboxylic acid methoxy-methyl-amide,
2,4-dichloro-N-(3,4-dimethoxy-phenyl)-N-[4-(4-methyl-piperazine-1-carbonyl)-thiazol-2-yl]-benzamide,
2-[(2,4-dichloro-benzoyl)-(3,4-dimethoxy-phenyl)-amino]-thiazole-4-carboxylic acid methyl-propyl-amide,
2,4-dichloro-N-(3,4-dimethoxy-phenyl)-N-[4-(3-methyl-piperidine-1-carbonyl)-thiazol-2-yl]-benzamide,
2,4-dichloro-N-(3,4-dimethoxy-phenyl)-N-[4-(3-hydroxy-piperidine-1-carbonyl)-thiazol-2-yl]-benzamide,
2,4-dichloro-N-(3,4-dimethoxy-phenyl)-N-[4-(4-hydroxy-piperidine-1-carbonyl)-thiazol-2-yl]-benzamide,
2-[(2,4-dichloro-benzoyl)-(3,4-dimethoxy-phenyl)-amino]-thiazole-4-carboxylic acid carbamoylmethyl-amide,
2-[(2,4-dichloro-benzoyl)-(3,4-dimethoxy-phenyl)-amino]-thiazole-4-carboxylic acid amide,
2-[(4-chloro-phenyl)-(2,4-dichloro-benzoyl)-amino]-thiazole-4-carboxylic acid (1-methyl-pipendin-4-yl)-amide,
2-[(4-chloro-phenyl)-(2,4-dichloro-benzoyl)-amino]-thiazole-4-carboxylic acid methyl-(1-methyl-pyrrolidin-3-yl)-amide,
2-[(4-chloro-phenyl)-(2,4-dichloro-benzoyl)-amino]-thiazole-4-carboxylic acid ethyl-[2-(ethyl-methyl-amino)-ethyl]-amide,
2-[(4-chloro-phenyl)-(2,4-dichloro-benzoyl)-amino]-thiazole-4-carboxylic acid (2-dimethylamino-1-methyl-ethyl)-amide,
2-[(4-chloro-phenyl)-(2,4-dichloro-benzoyl)-amino]-thiazole-4-carboxylic acid (2-hydroxy-ethyl)-isopropyl-amide,
2,4-dichloro-N-(4-chloro-phenyl)-N-[4-(4,4-difluoro-piperidine-1-carbonyl)-thiazol-2-yl]-benzamide,
2-[(4-chloro-phenyl)-(2,4-dichloro-benzoyl)-amino]-thiazole-4-carboxylic acid tert-butyl-(2-hydroxy-ethyl)-amide,
2,4-dichloro-N-(3,4-dimethoxy-phenyl)-N-[5-methyl-4-(pyrrolidine-1-carbonyl)-thiazol-2-yl]-benzamide,
2-[(2,4-dichloro-benzoyl)-(3,4-dimethoxy-phenyl)-amino]-5-methyl-thiazole-4-carboxylic acid (2-diethylamino-ethyl)-ethyl-amide,
2,4-dichloro-N-(3,4-dimethoxy-phenyl)-N-[4-(3-hydroxy-pyrrolidine-1-carbonyl)-5-methyl-thiazol-2-yl]-benzamide,
2,4-dichloro-N-(3,4-dimethoxy-phenyl)-N-[5-methyl-4-(thiomorpholine-4-carbonyl)-thiazol-2-yl]-benzamide,
2,4-dichloro-N-(3,4-dimethoxy-phenyl)-N-[5-methyl-4-(2-methyl-pyrrolidine-1-carbonyl)-thiazol-2-yl]-benzamide,
2-[(2,4-dichloro-benzoyl)-(3,4-dimethoxy-phenyl)-amino]-5-methyl-thiazole-4-carboxylic acid ethyl-methyl-amide,
2-[(2,4-dichloro-benzoyl)-(3,4-dimethoxy-phenyl)-amino]-5-methyl-thiazole-4-carboxylic acid methoxy-methyl-amide,
2-[(2,4-dichloro-benzoyl)-(3,4-dimethoxy-phenyl)-amino]-5-methyl-thiazole-4-carboxylic acid methyl-propyl-amide,
2,4-dichloro-N-(3,4-dimethoxy-phenyl)-N-[5-methyl-4-(3-methyl-pipendine-1-carbonyl)-thiazol-2-yl]-benzamide, 2,4-dichloro-N-(3,4-dimethoxy-phenyl)-N-[5-methyl-4-(morpholine-4-carbonyl)-thiazol-2-yl]-benzamide,
2-[(2,4-dichloro-benzoyl)-(3,4-dimethoxy-phenyl)-amino]-5-methyl-thiazole-4-carboxylic acid (2-hydroxy-ethyl)-methyl-amide,
2,4-dichloro-N-(3,4-dimethoxy-phenyl)-N-[4-(3-(S)-ethoxy-pyrrolidine-1-carbonyl)-5-methyl-thiazol-2-yl]-benzamide,
2-[(2,4-dichloro-benzoyl)-(3,4-dimethoxy-phenyl)-amino]-5-methyl-thiazole-4-carboxylic acid tert-butyl-(2-hydroxy-ethyl)-amide,
2,4-dichloro-N-[4-(2-(R)-cyano-pyrrolidine-1-carbonyl)-5-methyl-thiazol-2-yl]-N-(3,4-dimethoxy-phenyl)-benzamide,
2-[(4-chloro-phenyl)-(2,4-dichloro-benzoyl)-amino]-5-methyl-thiazole-4-carboxylic acid diethylamide,
2,4-dichloro-N-(4-chloro-phenyl)-N-[5-methyl-4-(pyrrolidine-1-carbonyl)-thiazol-2-yl]-benzamide,
2-[(4-chloro-phenyl)-(2,4-dichloro-benzoyl)-amino]-5-methyl-thiazole-4-carboxylic acid (2-diethylamino-ethyl)-ethyl-amide,
2-[(4-chloro-phenyl)-(2,4-dichloro-benzoyl)-amino]-5-methyl-thiazole-4-carboxylic acid (2-dimethylamino-ethyl)-ethyl-amide,
2,4-dichloro-N-(4-chloro-phenyl)-N-[4-(3-hydroxy-pyrrolidine-1-carbonyl)-5-methyl-thiazol-2-yl]-benzamide,
2-[(4-chloro-phenyl)-(2,4-dichloro-benzoyl)-amino]-5-methyl-thiazole-4-carboxylic acid (2,3-dihydroxy-propyl)-methyl-amide,
2-[(4-chloro-phenyl)-(2,4-dichloro-benzoyl)-amino]-5-methyl-thiazole-4-carboxylic acid ethyl-propyl-amide,
2-[(4-chloro-phenyl)-(2,4-dichloro-benzoyl)-amino]-5-methyl-thiazole-4-carboxylic acid ethyl-methyl-amide,
2-[(4-chloro-phenyl)-(2,4-dichloro-benzoyl)-amino]-5-methyl-thiazole-4-carboxylic acid methoxy-methyl-amide,
2-[(4-chloro-phenyl)-(2,4-dichloro-benzoyl)-amino]-5-methyl-thiazole-4-carboxylic acid methyl-propyl-amide,
2,4-dichloro-N-(4-chloro-phenyl)-N-[5-methyl-4-(morpholine-4-carbonyl)-thiazol-2-yl]-benzamide,
2-[(4-chloro-phenyl)-(2,4-dichloro-benzoyl)-amino]-5-methyl-thiazole-4-carboxylic acid (2-hydroxy-ethyl)-methyl-amide,
2,4-dichloro-N-(4-chloro-phenyl)-N-[4-(3-(R)-ethoxy-pyrrolidine-1-carbonyl)-5-methyl-thiazol-2-yl]-benzamide,
2-[(4-chloro-phenyl)-(2,4-dichloro-benzoyl)-amino]-5-methyl-thiazole-4-carboxylic acid tert-butyl-(2-hydroxy-ethyl)-amide,
2,4-dichloro-N-(4-chloro-phenyl)-N-[4-(2-(R)-cyano-pyrrolidine-1-carbonyl)-5-methyl-thiazot-2-yl]-benzamide,
2-[(2,4-dichloro-benzoyl)-(3,4-dimethoxy-phenyl)-amino]-thiazole-5-carboxylic acid diethylamide,
2,4-dichloro-N-(3,4-dimethoxy-phenyl)-N-[5-(pyrrolidine-1-carbonyl)-thiazol-2-yl]-benzamide,
2-[(2,4-dichloro-benzoyl)-(3,4-dimethoxy-phenyl)-amino]-thiazole-5-carboxylic acid (2-diethylamino-ethyl)-ethyl-amide,
2,4-dichloro-N-(3,4-dimethoxy-phenyl)-N-[5-(2-methyl-pyrrolidine-1-carbonyl)-thiazol-2-yl]-benzamide,
2-[(2,4-dichloro-benzoyl)-(3,4-dimethoxy-phenyl)-amino]-thiazole-5-carboxylic acid ethyl-methyl-amide,
2-[(2,4-dichloro-benzoyl)-(3,4-dimethoxy-phenyl)-amino]-thiazole-5-carboxylic acid methyl-propyl-amide,
2,4-dichloro-N-(3,4-dimethoxy-phenyl)-N-[5-(3-hydroxy-piperidine-1-carbonyl)-thiazol-2-yl]-benzamide,
2,4-dichloro-N-(3,4-dimethoxy-phenyl)-N-[5-(morpholine-4-carbonyl)-thiazol-2-yl]-benzamide,
2,4-dichloro-N-(3,4-dimethoxy-phenyl)-N-[5-(3-(R)-ethoxy-pyrrolidine-1-carbonyl)-thiazol-2-yl]-benzamide,
2-[(2,4-dichloro-benzoyl)-(3,4-dimethoxy-phenyl)-amino]-thiazole-5-carboxylic acid tert-butyl-(2-hydroxy-ethyl)-amide,
2,4-dichloro-N-[5-(2-(R)-cyano-pyrrolidine-1-carbonyl)-thiazol-2-yl]-N-(3,4-dimethoxy-phenyl)-benzamide,
2,4-dichloro-N-(4-chloro-phenyl)-N-[5-(pyrrolidine-1-carbonyl)-thiazol-2-yl]-benzamide,
2-[(4-chloro-phenyl)-(2,4-dichloro-benzoyl)-ammno]-thiazole-5-carboxylic acid piperidin-1-ylamide,
2,4-dichloro-N-(4-chloro-phenyl)-N-[5-(thiomorpholine-4-carbonyl)-thiazol-2-yl]-benzamide,
2-[(4-chloro-phenyl)-(2,4-dichloro-benzoyl)-amino]-thiazole-5-carboxylic acid ethyl-propyl-amide,
2-[(4-chloro-phenyl)-(2,4-dichloro-benzoyl)-amino]-thiazole-5-carboxylic acid bis-(2-methoxy-ethyl)-amide,
2,4-dichloro-N-(4-chloro-phenyl)-N-[5-(2-methyl-pyrrolidine-1-carbonyl)-thiazol-2-yl]-benzamide,
2-[(4-chloro-phenyl)-(2,4-dichloro-benzoyl)-amino]-thiazole-5-carboxylic acid ethyl-methyl-amide,
2-[(4-chloro-phenyl)-(2,4-dichloro-benzoyl)-amino]-thiazole-5-carboxylic acid methoxy-methyl-amide,
2,4-dichtoro-N-(4-chloro-phenyl)-N-[5-(4-methyl-piperazine-1-carbonyl)-thiazol-2-yl]-benzamide,
2-[(4-chloro-phenyl)-(2,4-dichloro-benzoyl)-amino]-thiazole-5-carboxylic acid methyl-propyl-amide,
2,4-dichloro-N-(4-chloro-phenyl)-N-[5-(3-(R)-ethoxy-pyrrolidine-1-carbonyl)-thiazol-2-yl]-benzamide,
2,4-dichloro-N-[4-(pyrrolidine-1-carbonyl)-thiazol-2-yl]-N-(4-trifluoromethoxy-phenyl)-benzamide,
2-chloro-N-[4-(pyrrolidine-1-carbonyl)-thiazol-2-yl]-N-(4-trifluoromethoxy-phenyl)-benzamide,
2-[(2-chloro-benzoyl)-(4-trifluoromethoxy-phenyl)-amino]-thiazole-4-carboxylic acid ethyl-methyl-amide,
2-[(2,4-dichloro-benzoyl)-(4-trifluoromethoxy-phenyl)-amino]-thiazole-4-carboxylic acid ethyl-methyl-amide,
rac-2,4-dichloro-N-[4-(2-methyl-pyrrolidine-1-carbonyl)-thiazol-2-yl]-N-(4-trifluoromethoxy-phenyl)-benzamide,
rac-2-chloro-4-fluoro-N-[4-(2-methyl-pyrrolidine-1-carbonyl)-thiazol-2-yl]-N-(4-trifluoromethoxy-phenyl)-benzamide,
rac-2-chloro-N-[4-(2-methyl-pyrrolidine-1-carbonyl)-thiazol-2-yl]-N-(4-trifluoromethoxy-phenyl)-benzamide,
2,4-dichloro-N-[4-(3(R)-hydroxy-pyrrolidine-1-carbonyl)-thiazol-2-yl]-N-(4-trifluoromethoxy-phenyl)-benzamide,
2-chtoro-N-[4-(3(R)-hydroxy-pyrrolidine-1-carbonyl)-thiazol-2-yl]-N-(4-trifluoromethoxy-phenyl)-benzamide,
rac-2,4-dichloro-N-(4-chloro-3-methoxy-phenyl)-N-[4-(2-methyl-pyrrolidine-1-carbonyl)-thiazol-2-yl]-benzamide,
2-chloro-4-fluoro-N-[4-((R)-3-hydroxy-pyrrolidine-1-carbonyl)-thiazol-2-yl]-N-(4-trifluoromethoxy-phenyl)-benzamide, 2,4-dichloro-N-(4-chloro-3-methoxy-phenyl)-N-[4-(pyrrolidine-1-carbonyl)-thiazol-2-yl]-benzamide, 2-[(4-chloro-3-methoxy-phenyl)-(2,4-dichloro-benzoyl)-amino]-thiazole-4-carboxylic acid ethyl-methyl-amide, 2,4-dichloro-N-(4-chloro-3-methoxy-phenyl)-N-[4-((R)-3-hydroxy-pyrrolidine-1-carbonyl)-thiazol-2-yl]-benzamide, 2,4-dichloro-N-(4-chloro-3-methoxy-phenyl)-N-[5-methyl-4-(pyrrolidine-1-carbonyl)-thiazol-2-yl]-benzamide, 2,4-dichloro-N-(4-chloro-3-methoxy-phenyl)-N-[5-methyl-4-(morpholine-4-carbonyl)-thiazol-2-yl]-benzamide, 2,4-dichloro-N-(4-chloro-3-methoxy-phenyl)-N-[4-((R)-3-hydroxy-pyrrolidine-1-carbonyl)-5-methyl-thiazol-2-yl]-benzamide, 2-[(4-chloro-3-methoxy-phenyl)-(2,4-dichloro-benzoyl)-amino]-5-methyl-thiazole-4-carboxylic acid 2-tert-butylamino-ethyl ester, and rac-2,4-dichloro-N-(4-chloro-3-methoxy-phenyl)-N-[5-methyl-4-(2-methyl-pyrrolidine-1-carbonyl)-thiazol-2-yl]-benzamide, and the pharmaceutically acceptable salts thereof.

18. The compound according to claim 1 selected from the group consisting of:

2-[(4-chloro-phenyl)-(2,4-dichloro-benzoyl)-amino]-thiazole-4-carboxylic acid (2-dimethylamino-ethyl)-ethyl-amide, 2,4-dichloro-N-(3,4-dimethoxy-phenyl)-N-[4-(2-methyl-pyrrolidine-1-carbonyl)-thiazol-2-yl]-benzamide, 2-[(2,4-dichloro-benzoyl)-(3,4-dimethoxy-phenyl)-amino]-thiazole-4-carboxylic acid methyl-propyl-amide, 2-[(4-chloro-phenyl)-(2,4-dichloro-benzoyl)-amino]-thiazole-4-carboxylic acid methyl-(1-methyl-pyrrolidin-3-yl)-amide, 2,4-dichloro-N-(3,4-dimethoxy-phenyl)-N-[5-methyl-4-(pyrrolidine-1-carbonyl)-thiazol-2-yl]-benzamide, 2-[(2,4-dichloro-benzoyl)-(3,4-dimethoxy-phenyl)-amino]-5-methyl-thiazole-4-carboxylic acid methoxy-methyl-amide, 2-[(2,4-dichloro-benzoyl)-(3,4-dimethoxy-phenyl)-amino]-5-methyl-thiazole-4-carboxylic acid methyl-propyl-amide, 2,4-dichloro-N-[4-(2-(R)-cyano-pyrrolidine-1-carbonyl)-5-methyl-thiazol-2-yl]-N-(3,4-dimethoxy-phenyl)-benzamide, 2-[(4-chloro-phenyl)-(2,4-dichloro-benzoyl)-amino]-5-methyl-thiazole-4-carboxylic acid (2-dimethylamino-ethyl)-ethyl-amide, 2-[(4-chloro-phenyl)-(2,4-dichloro-benzoyl)-amino]-5-methyl-thiazole-4-carboxylic acid tert-butyl-(2-hydroxy-ethyl)-amide, 2-[(2,4-dichloro-benzoyl)-(3,4-dimethoxy-phenyl)-amino]-thiazole-5-carboxylic acid methyl-propyl-amide, 2-[(2,4-dichloro-benzoyl)-(3,4-dimethoxy-phenyl)-amino]-thiazole-5-carboxylic acid tert-butyl-(2-hydroxy-ethyl)-amide, 2,4-dichloro-N-(4-chloro-phenyl)-N-[5-(4-methyl-piperazine-1-carbonyl)-thiazol-2-yl]-benzamide, 2-[(4-chloro-phenyl)-(2,4-dichloro-benzoyl)-amino]-thiazole-5-carboxylic acid methyl-propyl-amide, 2,4-dichloro-N-(4-chloro-3-methoxy-phenyl)-N-[4-(pyrrolidine-1-carbonyl)thiazole-2-yl]-benzamide, 2-[(4-chloro-3-methoxy-phenyl)-(2,4-dichloro-benzoyl)-amino]-5-methyl-thiazole-4-carboxylic acid 2-tert-butylamino-ethyl ester, 2,4-dichloro-N-(4-chloro-3-methoxy-phenyl)-N-[5-methyl-4-(2-methyl-pyrrolidine-1-carbonyl)-thiazol-2-yl]-benzamide, and the pharmaceutically acceptable salts thereof.

* * * * *